(12) United States Patent
Kitahata et al.

(10) Patent No.: US 8,034,740 B2
(45) Date of Patent: Oct. 11, 2011

(54) ADSORPTIVITY IMPARTING AGENT CONTAINING POROUS SILICA

(75) Inventors: Kouichi Kitahata, Yokkaichi (JP); Masaaki Yanagi, Yokkaichi (JP); Yuuki Kasama, Yokkaichi (JP); Noriko Nomura, Yokkaichi (JP); Kanae Teramoto, Yokkaichi (JP); Hironobu Nanbu, Yokkaichi (JP); Yoshiki Yamazaki, Yokkaichi (JP); Mitsumasa Horii, Aichi (JP); Yoshiaki Fukushima, Aichi (JP)

(73) Assignees: Taiyo Kagaku Co., Ltd., Yokkaichi-Shi (JP); Kabushiki Kaisha Toyota Chuo Kenkyusho, Aichi (JP)

(*) Notice: Subject to any disclaimer, the term of this patent is extended or adjusted under 35 U.S.C. 154(b) by 1211 days.

(21) Appl. No.: 10/588,453

(22) PCT Filed: Feb. 3, 2005

(86) PCT No.: PCT/JP2005/001619
§ 371 (c)(1),
(2), (4) Date: Sep. 26, 2006

(87) PCT Pub. No.: WO2005/075068
PCT Pub. Date: Aug. 18, 2005

(65) Prior Publication Data
US 2007/0166438 A1      Jul. 19, 2007

(30) Foreign Application Priority Data

| Feb. 5, 2004 | (JP) | 2004-029971 |
| Feb. 5, 2004 | (JP) | 2004-029973 |
| Feb. 5, 2004 | (JP) | 2004-029974 |
| Feb. 5, 2004 | (JP) | 2004-029980 |
| Feb. 5, 2004 | (JP) | 2004-029982 |
| Feb. 5, 2004 | (JP) | 2004-029989 |
| Jul. 28, 2004 | (JP) | 2004-220912 |

(51) Int. Cl.
| B01J 20/00 | (2006.01) |
| C01B 33/12 | (2006.01) |
| A61K 8/02 | (2006.01) |
| A61K 33/00 | (2006.01) |
| A61K 31/02 | (2006.01) |
| A01N 59/00 | (2006.01) |
| A01N 25/00 | (2006.01) |
| C09K 3/00 | (2006.01) |
| A01K 1/015 | (2006.01) |
| B65D 75/00 | (2006.01) |
| B32B 5/18 | (2006.01) |
| B32B 5/22 | (2006.01) |
| B32B 5/02 | (2006.01) |
| B32B 27/04 | (2006.01) |
| B32B 27/12 | (2006.01) |
| C04B 28/26 | (2006.01) |
| C09D 4/00 | (2006.01) |
| C09D 101/00 | (2006.01) |

(52) U.S. Cl. ........ 502/407; 423/335; 424/401; 424/724; 252/183.13; 428/221; 229/87.08; 442/76; 442/118; 442/121; 106/243; 106/287.34; 514/770

(58) Field of Classification Search .......... 423/335–340; 229/87.08; 442/76, 121, 122, 417, 118; 428/32, 428/37, 221; 502/407; 424/401, 724; 252/183.13; 106/243, 287.34; 514/770
See application file for complete search history.

(56) References Cited

U.S. PATENT DOCUMENTS

| 4,230,765 A * | 10/1980 | Takahashi et al. ........ 428/292.1 |
| 4,895,681 A * | 1/1990 | Herrmann et al. ........... 554/223 |
| 5,599,759 A * | 2/1997 | Inagaki et al. ................ 502/80 |
| 5,776,240 A * | 7/1998 | Deller et al. ................ 106/482 |
| 5,922,299 A * | 7/1999 | Bruinsma et al. ............ 423/335 |
| 2002/0051802 A1 | 5/2002 | Shio et al. |
| 2003/0072779 A1 | 4/2003 | Sato et al. |
| 2003/0072799 A1* | 4/2003 | Sowden et al. .............. 424/464 |
| 2003/0195220 A1* | 10/2003 | Murakami et al. ....... 514/255.05 |
| 2004/0062835 A1 | 4/2004 | Earl et al. |
| 2005/0031520 A1* | 2/2005 | Fortier et al. ................ 423/335 |

| | FOREIGN PATENT DOCUMENTS | |
|---|---|---|
| JP | 53-6611 | 1/1978 |
| JP | 56-148585 A | 11/1981 |
| JP | 59-95931 A | 6/1984 |
| JP | 61-163850 A | 7/1986 |
| JP | 62-26813 B2 | 6/1987 |
| JP | 62-289512 A | 12/1987 |
| JP | 63-38188 B2 | 7/1988 |
| JP | 3-27483 B2 | 4/1991 |
| JP | 3-93662 A | 4/1991 |
| JP | 3-109244 A | 5/1991 |
| JP | 5-177132 A | 7/1993 |
| JP | 5-279967 A | 10/1993 |
| JP | 5-302781 A | 11/1993 |
| JP | 6-9885 A | 1/1994 |
| JP | 7-132974 A | 5/1995 |
| JP | 7-136240 A | 5/1995 |
| JP | 7-155369 A | 6/1995 |
| JP | 8-67578 A | 3/1996 |
| JP | 10-152317 A | 6/1996 |
| JP | 8-173137 A | 7/1996 |
| JP | 9-25114 A | 1/1997 |
| JP | 9-132871 A | 5/1997 |
| JP | 9-208809 A | 8/1997 |
| JP | 11-106324 | 4/1999 |
| JP | 11-292152 A | 10/1999 |
| JP | 2000-168791 A | 6/2000 |
| JP | 2000-204230 A | 7/2000 |
| JP | 2001-179086 | 7/2001 |
| JP | 2001-219059 A | 8/2001 |
| JP | 2002-503979 A | 2/2002 |
| JP | 2002-145734 A | 5/2002 |
| JP | 2002-187712 | 7/2002 |
| JP | 2003-003013 | 1/2003 |
| JP | 2003-190781 A | 7/2003 |
| JP | 2005-089218 | 4/2005 |
| WO | WO-2002057403 A1 | 7/2002 |

* cited by examiner

*Primary Examiner* — Stanley Silverman

*Assistant Examiner* — Anthony J Zimmer

(74) *Attorney, Agent, or Firm* — Birch, Stewart, Kolasch & Birch, LLP

(57) ABSTRACT

A moisture- or protein-adsorbability imparting agent, comprising a porous silica having a hexagonal pore structure, an average pore size of from 0.8 to 20 nm, an average particle size of 50 nm to 100 μm, a specific surface area of from 400 to 2000 $m^2/g$, and a pore volume of from 0.1 to 3.0 $cm^3/g$; a material having an adsorbability of moisture or a protein, comprising the moisture- or protein-adsorbability imparting agent; and use of the moisture- or protein-adsorbability imparting agent for imparting absorbability of moisture or a protein to a material selected from the group consisting of food wrapping materials; filtration aid agents; sanitary articles; compositions containing a synthetic resin; moisture-controlled material; covering materials for wounds; insulation substrates; coating materials for semiconductor devices; cosmetics; inkjet recording media; and compositions containing synthetic fibers.

6 Claims, 1 Drawing Sheet

[Figure 1]
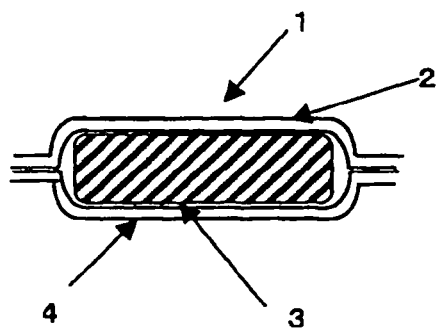
[Figure 2]
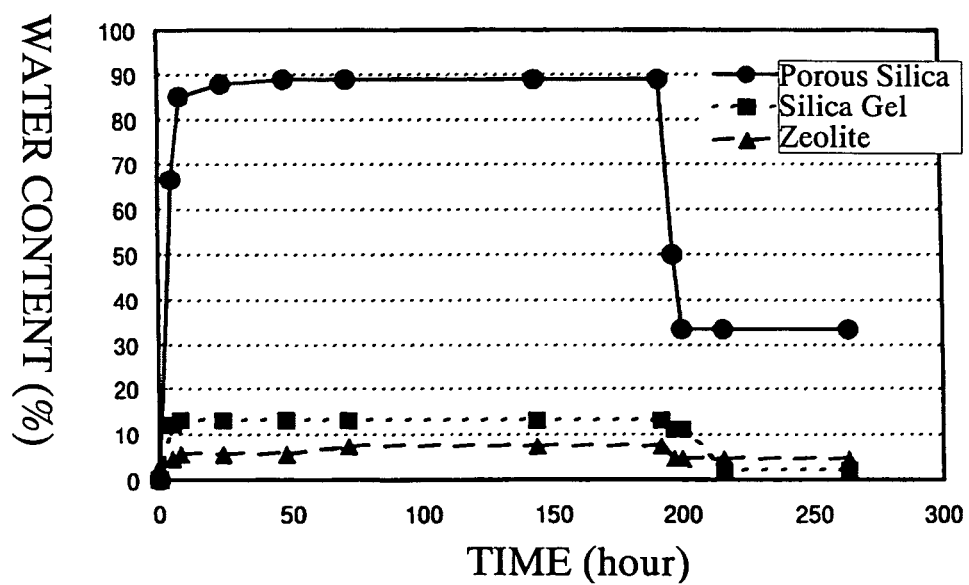

ADSORPTIVITY IMPARTING AGENT CONTAINING POROUS SILICA

TECHNICAL FIELD

The present invention relates to an agent capable of imparting moisture- or protein-adsorbability to various materials.

BACKGROUND ART

Conventionally, as microwave oven-cooking foods, those foods prepared by cooking deep fried goods such as croquettes, deep fries and deep fried chickens or rice, and freezing them, packaged in a bag or a container such as a tray are commercially available. When the microwave oven-cooking foods as mentioned above are cooked in a microwave oven, water or an oil in the foods is gathered in the wrapping bag or the container to be adhered to foods, so that there are some disadvantages that the tastes of the foods are spoiled, and that the water or the oil is adhered to hands, the oven, clothes, and the like. Especially, when deep fried goods such as croquettes, deep fries, deep fried chickens, deep fried potatoes, and egg rolls are cooked in a microwave oven, if water or an oil oozing from the foods is adhered to surfaces of the foods, there are some disadvantages that a crispy finish cannot be obtained, so that the tastes of the foods are drastically spoiled. In addition, there is a disadvantage in hamburgers, steam dumplings, broiled rice balls (yaki-onigiri), and the like that the stickiness of the foods is generated due to dew condensation on the surface of the wrapping material, thereby making the palatability poor.

In order to solve the above-mentioned problems, there have been proposed a laminated sheet comprising a hydrophobic fiber sheet that is water-permeable, serving as an inner layer contacting the food, an absorbent fiber sheet for absorbing and holding water serving as an intermediate layer, and a film made of a water-impermeable synthetic resin serving as an outer layer (see, for example, Patent Publication 1); an oil-absorbent, water-absorbent wrapping material constituted by a laminate comprising a gas-impermeable film layer serving as an outer layer, and a nonwoven fabric layer made of a thermoplastic resin, at least a part of the layers has a hydrophilicity, serving as an inner layer (see, for example, Patent Publication 2); a sheet for food wrapping constituted by an outer layer sheet, a water-absorbent sheet, and a liquid-permeable inner layer sheet (see, for example, Patent Publication 3); and the like. However, none of these were sufficiently satisfactory.

Next, a brewed good such as sake, sweet sake (mirin), or beer has been known to form a colloidal substance by association of a protein or an enzyme derived from rice or barley, the raw material in the process of the brewing process. This colloidal substance is causative of dregs which drastically spoil the quality as a manufactured article. Also, when this colloidal substance is tried to be separated by filtration, there arise some disadvantages that the filtration resistance drastically increases, thereby making it difficult to filter.

As processes for solving the disadvantages as described above, the processes as given below have so far been known:
(1) a process comprising adsorbing a causative substance of muddiness utilizing an adsorbent, and centrifuging the resulting mixture;
(2) a process comprising pre-coating a filtration material with an adsorbent or a filtration aid in advance, and separating away and removing the adsorbed-substance by filtration, while feeding a brewed good such as sake, sweet sake or beer; and
(3) a process comprising degrading a protein with an enzyme.

As the above-mentioned absorbent, there have been known an organic adsorbent such as tannin or polyvinyl polypyrrolidone (PVPP); and an inorganic adsorbent such as silica gel. As the filtration aid, diatomaceous earth, perlite, cellulose or the like has been known. Further, the protein-degradable enzyme includes papain or the like. Among them, the silica gel is widely used, because the silica gel has a smaller influence to the quality of the product to be filtered, and excellent adsorbability, and also excellent performance as a filtration aid.

In general, the silica gel can be prepared by a neutralization reaction between an aqueous alkali metal silicate solution and a mineral acid, and this preparation process is called a wet process. The wet process is classified into a precipitation method comprising reacting the components under neutral or basic conditions, to obtain a precipitated silicic acid which is more easily filtered; and a gel method comprising reacting the components under acidic conditions to give a gel-like silicic acid.

In the gel method, for example, a gel-like silicic acid (silica hydrogel) obtained by an acidic reaction is washed with water and dried, and thereafter the dried product is pulverized to give a silica gel. These silica gels generally have higher structural property as compared to those of the precipitation method, and their structural property can be kept even under high shearing force. Therefore, the silica gel has been used as a coating agent for synthetic leather and plastics, an anti-blocking agent for a resin film, an adsorbent, a separating agent, or a catalyst. Because of the properties as described above, the silica gel has been generally widely used in the field of filtration aid, as compared to the precipitated silicic acid.

The important feature as an absorbent is to adsorb a substance, and factors for limiting adsorption include 1) a high specific surface area, 2) selective adsorbability, and 3) ion exchanging capacity with a metal or the like. Similarly, there are two features, filterability and adsorbability (selective adsorbability), as the properties required for a filtration aid. Factors limiting the former (filterability) are filtration speed and the its own strength, and factors limiting the latter (adsorbability) are specific surface area, pore volume and pore size. In a case where a product to be filtered is a food, especially a luxury article such as a fermented drink such as beer, adjustment of very sensitive taste, flavor and a degree of coloration has been required. In silica gels for filtration aids, there has been strongly desired to even more highly precisely discern and select various components that give influences to taste, flavor and a degree of coloration, and adsorb only the unnecessary portions while passing the necessary portion. The realization of the high-precision adsorbability as described above relies on how precisely the pore size of the silica gel for a filtration aid can be controlled depending upon the size of the desired component to be removed from a product to be filtered.

Regarding silica gels for filtration aids, there are many patents published that define various properties in view of the above. For example, there have been disclosed baked silica xerogel (see, for example, Patent Publication 4); as a water-containing silica gel, a silica gel having given physical properties obtained by controlling a water content (see, for example, Patent Publication 5); a silica gel having a feature in its shape of thin slices, flakes or rods, the silica gel having specified physical properties (see, for example, Patent Publication 6); a silica gel for treatment of beer stabilization having the physical properties of a specific surface area of from 700 to 1000 $m^2/g$, a pore volume of from 1.1 to 1.6 mL/g, an average pore size of from 6 to 10 nm, the silica gel being prepared by baking at a temperature of from 400° to 800° C. for 10 seconds to 10 hours (see, for example, Patent Publication 7); a silica gel for a filtration agent, characterized in that one having a pore size of from 50 to 500 Å has a pore volume within the range from 0.7 to 2.5 mL/g, and one having a pore size exceeding 500 Å has a pore volume within the range from 0.2 to 0.8 mL/g (see, for example, Patent Publication 8); a silica gel for a filtration aid, characterized in that a pore volume is from 0.6 to 2.0 mL/g, a specific surface area is from 300 to 1000 m$^2$/g, a mode diameter (Dmax) of the pore of less than 20 nm, and a total volume of the pores of which diameters fall within the range of Dmax±20% is 50% or more of the entire pores, that the silica gel is amorphous, that a total content of metal impurity is 500 ppm or less, that when the chemical shift of $Q^4$ peak in a solid Si—NMR is defined as $\delta$ (ppm), $\delta$
satisfies $-0.0705\times(Dmax)-110.36>\delta$ (see, for example, Patent Publication 9); and the like.

A method of making a leakage-preventing layer of a water-absorbent article moisture-permeable, thereby reducing a wet feel or damp feel upon fitting the article, and at the same time controlling water-containing swelling of skin, thereby controlling skin troubles has been used in the fields of baby's diapers, adult diapers, incontinence pads, panty liners, and the like. According to this method, water vapor is exhausted to an external of the absorbent article, thereby reducing humidity inside the fitted article. However, odor is permeated through the absorbent article together with water vapor, thereby consequently undesirably increasing unpleasantness of odor as compared to the absorbent article comprising a leakage-preventing layer that is not moisture-permeable. In addition, active carbon is porous and has a very large adsorption volume, and excellent moisture absorbency and water absorbency. However, the active carbon does not have moisture-releasing property or water-releasing property, so that once moisture absorption or water absorption takes place, a very long period of time would be required until drying, so that there is intrinsically a disadvantage that propagation of bacteria or the like is enhanced.

In view of the above, an absorbent article using a leakage-preventing layer having air-permeability and a deodorant (see, for example, Patent Publication 10) has been proposed.

Next, a synthetic resin such as a polyvinyl chloride resin, a polyurethane resin, a polyacrylic resin, a polyamide resin, a polyester resin, poly(amino acid)-based resin, a polyolefin-based resin, or an epoxy resin has been used for a variety of applications as a film in a wrapping material, clothes, a covering material or the like.

However, these resins generally have strong hydrophobicity but their water breathability is not high. Here, the term water breathability refers to physical properties relating to moisture-absorbing property and moisture-releasing property, which is an ability of taking in a large amount of water quickly under high-humidity conditions, and releasing water quickly under low-humidity conditions.

In addition, these synthetic resins may be used as synthetic leather in many cases. Here, synthetic leather refers to those comprising a support made of a woven fabric, a braided fabric, paper, or a nonwoven fabric and a natural leather-like surface layer made of a polymeric substance, which is a material finished in a leather-like fashion, a majority of which comprises a microporous member made of polyvinyl chloride, polyamide or polyurethane and a finishing layer made of a modified polyamide, polyurethane, a polyacrylic acid derivative, or a polyamino acid blend, formed on the surface of the microporous member. In recent years, the properties of the synthetic leather have improved, and there are some that are comparable in appearance and properties to the natural leather. However, recently, the sensitiveness and the demands of the consumers are also increasing, so that improvement in moist texture even more closer to that of the natural leather has been desired.

In order to improve the texture distinctively owned by leather as described above, a method comprising mixing collagen into a resin (see, for example, Patent Publications 11 and 12), a method of using an esterified protein (see, for example, Patent Publication 13), and the like have been disclosed.

Next, houses constructed under temperate humid climate in Japan have various disadvantages especially in the aspect of moisture control. For example, dampness accumulated by high temperatures and high humidity in the summertime give rises to cause unpleasant odor in wall, wooden material or the like, or bacterial growth. In addition, although the humidity inside the house in the wintertime is low, owing to the high airtightness of housing and the widespread of heating equipments, dew condensation of the internal part of a wall material is induced accompanying lowering in the temperature during nighttime, thereby causing deterioration of the wall material. In order to prevent beforehand the damages caused by bacterial growth and deterioration of the wall material due to dampness as mentioned above, conventionally, as those usable in drying and moisture control, unslaked lime, calcium chloride, silica gel or the like has been generally used, or dehumidification of indoors by a dehumidifier, air-conditioning equipments such as an air conditioner has been generally utilized. In addition, as a means of solving the disadvantage as described above, developments have been made on a composition comprising, as main components, a saponified product of a copolymer having a specified composition as a hygroscopic material, and a deliquescent salt, the composition further comprising a fibrous substance (see, for example, Patent Publication 14); or as moisture adsorbing-releasing construction materials, xonotlite-based, allophane-based and zeolite-based construction materials (see, for example, Patent Publication 15); and the like.

In addition, in recent years, with the changes in the improvement of living standards and life styles of people, there is a growing concern in the technique of removing odor that is disadvantageous from the viewpoint of environmental sanitation in ordinary households and public space. In connection with the disadvantages as described above, there is a strong demand from the society as well as industrial circles on the development of the techniques of removing these odors, so that it has becoming more demanding to sufficiently meet the requirement. Conventionally, as means of solving these disadvantages, developments have been made on, for example, an adsorbing substance-containing paper containing sepiolite powder (see, for example, Patent Publication 16); an aluminum compound-containing sheet-like substance (see, for example, Patent Publication 17); and the like.

However, all of the above-mentioned humidity-preventing drying agents have strong dehumidifying power, thereby making it difficult to control the amount of dehumidification or the dehumidifying rate. In addition, there are some disadvantages such as an effective period for adsorbing moisture is short, and hygroscopic function is dramatically lowered once a saturation point is reached, thereby making it impossible to use the drying agents repeatedly. Since such a material is excellent only in hygroscopicity, the material is always in a water-retaining state, so that the generation of microorganisms is accelerated, which tends to accompany an unpleasant odor. Zeolite is excellent in hygroscopicity but poor in humidity-releasing property, so that zeolite cannot be said to be suitable for a water adsorbing-releasing material, making it more likely to provide a hotbed of microorganisms and generation of foul odors. The dehumidification by a dehumidifier has a disadvantage energetically, and at the same-time causes to lower the humidity of the environment in the required amount or more, so that there is a possibility of having a harmful influence to health. In addition, materials such as a zeolite/cement-based construction material (see, for example, Patent Publication 18), and a silica gel-based water adsorbing-releasing agent (see, for example, Patent Publication 19) have been developed, many of which do not take careful notes in pore size distribution, so that these materials do not have excellent humidity-controlling functions, and at the same time the materials have small solid acid points, so that they do not have deodorization function. In order to overcome this disadvantage, a material utilizing siliceous grit (see, for example, Patent Publication 20) has been proposed.

On the other hand, in recent year, there are some concerns in a sick house syndrome, multiple chemical sensitivity and the like. This is considered to be caused by an adhesive which is used upon pasting a wall paper, a gaseous chemical substance derived from a treatment agent used in a processing step of a construction material or the like. In addition, in a living environment, various odorous gases such as smokes from cigarettes and decomposed gases derived from microorganisms in a wet area have been generated. Therefore, a demand for a wall paper having a function of preparing a suitable living environment, such as deodorization function, has been very highly increased.

Next, conventionally, in the treatment of a burn, a cut, an abrasion, an ulcer or the like, as a wound covering material for covering or protecting an affected part, cotton, cotton gauze, a nonwoven fabric, an ointment or the like has been used. In addition, in burns, especially a nonwoven fabric made of pig skin or chitin fiber or the like has been used.

However, a cotton manufactured article such as cotton gauze cannot be said to have sufficient absorbability of a body fluid, so that there has been a disadvantage that the cotton manufactured article cannot quickly absorb a body fluid oozing from a wound. In addition, the cotton manufactured article shows a mild release of water, the cotton manufactured article is less likely to be dried, so that the wound tends to become damp. In order to prevent this, a cotton manufactured article for wound coverage has to be frequently exchanged, thereby giving rise to a disadvantage of requiring much labor. Also, ointment has some disadvantages such as the ointment has a low wound covering effect, and much labor is required for the treatment.

On the other hand, recently, alginic acid-based wound covering materials have been proposed (see, for example, Patent Publications 21 and 22). In both of these alginic acid-based wound covering materials, those in which a fibrous alginate is worked into a nonwoven fabric or a fabric have been used.

Next, conventionally, a pre-molding-type, or molding-type semiconductor device mounted to an information processing instrument such as a computer is manufactured as follows. For example, in the case of the pre-molding type semiconductor device, a package for housing semiconductor elements, comprising an insulation substrate made of an epoxy resin, the insulation substrate having dent portions formed on an upper side thereof for housing semiconductor elements, plural external lead terminals for leading out from the dent portion side to the outer side of the insulation substrate, and a lid member being mounted on the upper side of the insulation substrate via an encapsulation material, the lid serving to cover the dent portions of the insulation substrate is furnished. Next, each of the semiconductor elements is mounted to the bottom of the dent portions of the insulation substrate via a resin bonding material, and at the same time each electrode of the semiconductor elements is electrically connected to one end of the external lead terminal via a bonding wire, and thereafter, the lid member is bonded to an upper side of the insulation substrate via a resin encapsulation material, thereby air-tightly housing the semiconductor elements in the internal of the vessel comprising the insulation substrate and the lid member, to give a semiconductor device. Also, in the case of the molding-type semiconductor device, the semiconductor device comprises semiconductor elements, a substrate made of a metal material such as an Fe—Ni—Co alloy or an Fe—Ni alloy and plural external lead terminals, and a covering material made of an epoxy resin or the like, in which the semiconductor elements are fixed on the substrate via a waxy material such as a gold-silicon amorphous alloy, and at the same time each of the electrodes of the semiconductor elements are electrically connected to external lead terminals via a bonding wire, and thereafter, a part of the semiconductor elements, the substrate and the external lead terminals is covered with a covering material, to give a semiconductor device.

However, in this conventional semiconductor device, either the insulation substrate in the case of the pre-mold-type semiconductor device, or the covering material in the case where the mold-type semiconductor device is made of an epoxy resin or the like. The resin material such as the epoxy resin has poor moisture tolerance and more likely to absorb water, so that water contained in the atmosphere easily penetrates to the internal through the insulation substrate or the covering material. Therefore, consequently, there are some disadvantages such as oxidative corrosion is generated due to the water in the electrodes of the semiconductor elements or the bonding wire or the like, and at the same time the electrodes of the semiconductor elements and the bonding wire are likely to be snapped, thereby losing the function as a semiconductor device.

In order to overcome the above disadvantages, it has been considered to previously embed a filler made of particles of silica, alumina or the like into the insulation substrate or the covering material for the purpose of preventing penetration of water thereinto.

However, when the filler made of particles of silica, alumina or the like is embedded into the insulation substrate or the covering material, the embedded amount of the filler is at most 97% by weight, in consideration of moldability of the insulation substrate or the covering material, so that the resin material such as an epoxy resin is still contained in an amount of 3% by weight or so. Therefore, the penetration of water into the insulation substrate or the covering material cannot be completely blocked, and consequently, there is a disadvantage such as oxidative corrosion is still generated in the electrodes of the semiconductor elements, and the like.

In order to overcome the disadvantage as mentioned above, there has been proposed embedment of amorphous silica-based regular particles having specified particle size, specific surface area, amount of equilibrium moisture absorption (RH 50%) and bulk density in a resin for forming a package for housing semiconductor elements, thereby improving hygroscopicity of the package for housing semiconductor elements (see, for example, Patent Publication 23).

Next, as one embodiment of cosmetics, deodorant cosmetics for suppressing unpleasant feel due to excessive sweating by its antiperspirant function that controls perspiration, and at the same time suppressing unpleasant body odor generated of which main causation is sweat. As deodorant cosmetics, various types such as powder-sprays, roll-ons, sticks, gel, and cream have been conventionally used. These deodorant cosmetics usually comprise an antiperspirant component, an antibacterial component, and a deodorant component in the form of powder, an oil component, a surfactant or a wax, or the like. In order to prevent an odor from being generated from a human body, deodorant cosmetics containing a silver salt and/or a zinc salt (see, for example, Patent Publication 24), and the like have been proposed.

In addition, there has been a disadvantage in the conventional deodorant cosmetics that sticky feel is generated upon perspiration or after drying the perspiration. In the above-mentioned cosmetics, various improvements in feels of use such as silicic acid anhydride having perspiration-absorbing, sebum-absorbing effect is formulated, and a component having volatility mainly comprising ethanol or the like is formulated, for the purpose of giving a refreshing feel have been tried.

Next, inkjet printing process has some features of having smaller noises during printing and excellent high-speed printability, thereby facilitating multi-coloration. However, a fine quality paper or the like which has been used in ordinary printing is disadvantageous in ink absorbability, drying property and image quality such as resolution, so that specialized paper having improvement in these physical properties has been developed. A recording paper prepared by adding a porous inorganic pigment such as an amorphous silica for the purpose of increasing color development of an ink has been disclosed (see, for example, Patent Publication 25).

Finally, synthetic fibers have many of excellent physical properties such as mechanical properties, and have been used in multi-purposes such as applications of clothes. However, since the synthetic fibers are hydrophobic, their water absorbability or hygroscopicity is markedly low. Therefore, when the synthetic fibers are utilized for the applications of clothes, there are some disadvantages such as unpleasant damp feel is generated upon high humidity, or electrostatics are likely to be generated upon low humidity.

Therefore, there has been proposed a method of subjecting a polyester constituting the fibers to graft polymerization with a hydrophilic compound; a method of blending a hydrophilic compound in the polyester; a method of applying a hydrophilic compound to a fiber surface; or the like. However, in the case of the method of subjecting the hydrophobic compound to graft polymerization, if the hydrophilic compound is introduced in a large amount to impart sufficient hydrophilicity to the fibers, there is a disadvantage that inherent physical properties owned by the polyester fiber are lost. Also, in the case of a method of blending a hydrophilic compound into the polyester, there is a disadvantage that a feel of the fibers, especially skin feel, is more likely to be poor. Further, in the case of a method of applying a hydrophilic compound, there is a disadvantage that a hydrophilic compound is detached from the fiber surface by friction, washing or the like, so that the fibers do not have durability.

In addition, as an alternative method, there has been proposed the formation of a composite fiber composed of a hydrophobic polymer and a hydrophilic polymer. As one example thereof, a flat composite fiber in which a hydrophobic polyester and a hygroscopic polyamide are pasted together to form a composite has been known. However, in the case of this flat composite fiber, there are some disadvantages such as fiber cross section is deformed upon an after-process step such as extension processing, temporary twisting processing, or weaving step, or pasted portions are peeled away, thereby making it unpractical.

In addition, Patent Publication 26 proposes a core-sheath composite fiber comprising a hygroscopic polymer as a core component and a polyester as a sheath component, the polyester covering the hygroscopic polymer. However, the hygroscopic polymer, which is the core component has some disadvantages such as the hydroscopic polymer is swollen upon a hot water treatment such as scouring or dyeing, undesirably causing cracks on the fiber surface, whereby an oozing of the hygroscopic polymer or dye fastness is worsened.

In order to solve these disadvantages, a polyester fiber to which porous inorganic particles having hygroscopicity, so-called a wet silica, are added, has been proposed in Patent Publication 27. When this polyester fiber containing the wet silica is used, cracks of the fiber surface as those in Patent Publication 26 were certainly not generated.

| Patent Publication 1 | Japanese Patent Laid-Open No. Hei 7-132974 |
|---|---|
| Patent Publication 2 | Japanese Patent Laid-Open No. Hei 11-292152 |
| Patent Publication 3 | Japanese Patent Laid-Open No. 2000-168791 |
| Patent Publication 4 | Japanese Examined Patent Publication No. Sho 63-38188 |
| Patent Publication 5 | Japanese Examined Patent Publication No. Hei 3-27483 |
| Patent Publication 6 | Japanese Patent Laid-Open No. Hei 5-177132 |
| Patent Publication 7 | Japanese Patent Laid-Open No. Hei 8-173137 |
| Patent Publication 8 | Japanese Patent Laid-Open No. Hei 9-25114 |
| Patent Publication 9 | Japanese Patent Laid-Open No. 2003-190781 |
| Patent Publication 10 | Japanese Unexamined Patent Publication No. 2002-503979 |
| Patent Publication 11 | Japanese Patent Laid-Open No. Sho 61-163850 |
| Patent Publication 12 | Japanese Patent Laid-Open No. Hei 5-279967 |
| Patent Publication 13 | Japanese Patent Laid-Open No. Hei 6-9885 |
| Patent Publication 14 | Japanese Examined Patent Publication No. Sho 62-26813 |
| Patent Publication 15 | Japanese Patent Laid-Open No. Hei 3-93662 |
| Patent Publication 16 | Japanese Patent Laid-Open No. Sho 53-6611 |
| Patent Publication 17 | Japanese Patent Laid-Open No. Sho 59-95931 |
| Patent Publication 18 | Japanese Patent Laid-Open No. Hei 3-109244 |
| Patent Publication 19 | Japanese Patent Laid-Open No. Hei 5-302781 |
| Patent Publication 20 | Japanese Patent Laid-Open No. 2001-219059 |
| Patent Publication 21 | Japanese Patent Laid-Open No. Hei 7-136240 |
| Patent Publication 22 | Japanese Patent Laid-Open No. Hei 7-155369 |
| Patent Publication 23 | Japanese Patent Laid-Open No. Hei 9-208809 |
| Patent Publication 24 | Japanese Patent Laid-Open No. Sho 62-289512 |
| Patent Publication 25 | Japanese Patent Laid-Open No. Sho 56-148585 |
| Patent Publication 26 | Japanese Patent Laid-Open No. Hei 9-132871 |
| Patent Publication 27 | Japanese Patent Laid-Open No. Sho 2000-204230 |

DISCLOSURE OF THE INVENTION

Problems to be Solved by the Invention

An object of the present invention is to provide a moisture- or protein-adsorbability imparting agent, which has both high adsorbability and desorbability.

Disadvantages of Conventional Food Wrapping Materials

All of the conventional food wrapping materials have not arrived at sufficiently solving the above-mentioned disadvantages. Therefore, the present invention is to provide a food wrapping material which is capable of finishing a steaming warm food such as a soft, steam bun with meat fillings, or bread hot from the oven in a state that does not lose the taste of the food by absorbing excessive water or oil coming out from the food upon the use of the wrapping material for a food of the present invention, when heating the food with a microwave oven or wrapping the warm food, and at the same time capable of preventing hands, ovens, clothes and the like from being soiled.

Disadvantages of Conventional Filtration Aid

Conventional filtration aids still have disadvantages such as poor filtration efficiency, brittle particles and taste of the filtered manufactured article is dropped, so that the effects have not been necessarily satisfactory. When a silica gel composed of brittle particles is used as a filtration aid, and contacted with Japanese wine (sake), a sweet sake, or beer, there are some disadvantages such as the particles are broken down with the passage of time, thereby lowering a filtration speed, and by the breakdown of the particles, pore volume and average pore diameter are reduced, and whereby consequently also lowering adsorbability. In addition, the adsorbed substances are baked and removed to regenerate and use the filtration aid is usually conducted for the sake of reduction in costs and environmental burdens. However, in a case where the particles are brittle, there is a disadvantage such as the number of time that can be regenerated and used is also lowered.

Accordingly, another object of the present invention is to provide a filtration aid having more excellent adsorbability than that of the conventional products, that only removes a protein or the like unnecessary in a manufactured article, but not the necessary protein, and further having even more improved filtration properties such as filtration speed and strength as a filter than those of conventional silica gels. A still another object of the present invention is to provide a filtration aid having excellent performance, such as excellent filtration properties and improved adsorption speed by improving a filtration speed.

Disadvantages of Conventional Sanitary Articles

In a conventional absorbent article, since a deodorant is contained in an absorbent body, a foul odor generated from the absorbed liquid cannot be completely deodorized by a deodorant contained in the absorbent body. Therefore, there is a disadvantage that the foul odor passes through a leakage-preventing layer and is released from the fitted article.

Accordingly, another object of the present invention is to provide a sanitary article capable of satisfying both an odor-controlling function and a moisture-permeable function, capable of quickly discharging water vapor, while preventing the release of a foul odor generated from an absorbed liquid.

Disadvantages of Conventional Compositions Containing Synthetic Resins

Conventional synthetic resins cannot follow humidity changes of the external because of its low water breathability, which in turn leads to cause disadvantage such as generation of water dew condensation on a resin surface. Since these resins are used in wrapping materials in the form of a film, clothes materials, covering materials and the like in many cases, a disadvantage that dew condensation is likely to be generated is fatal, so that its improvement has been earnestly desired. In addition, in order to enhance the texture distinctively owned by leather, synthetic leather prepared using a conventionally employed method has insufficient water breathability, so that one that is satisfactory in the aspect of moist texture cannot be currently produced.

Accordingly, another object of the present invention is to provide a composition containing a synthetic resin having excellent water breathability, which is suitable for obtaining a film that is less likely to generate dew condensation and a synthetic leather having a moist texture.

Disadvantages of Conventional Moisture-Controlled Materials

Conventional moisture-controlled materials have been only capable of deodorizing a basic gas, and have a small amount of water absorption per unit weight because of their small specific surface areas, thereby making them unsatisfactory.

In addition, conventional deodorizing materials are prepared by mixing an adsorbent such as an aluminum compound or sepiolite and a fibrous substance to impart adsorbability. However, the conventional deodorizing materials have a very low ability of removing odors that are disadvantageous in the aspect of environmental sanitation, so that it cannot be said to be practical. As described above, in the conventional techniques, the materials that can achieve humidity control and deodorization at the same time have not been developed, and their properties have not been sufficient.

Accordingly, another object of the present invention is to provide a moisture-controlled material having a moisture-controlled function of wide applications, in which moisture in the living space is autonomously adsorbed and desorbed, thereby controlling humidity in the living environment in an optimal state in an energy conservation manner, and at the same time having a deodorizing function.

Disadvantages of Conventional Covering Materials for Wounds

Conventionally, in order to fix to an opening of a wound, a nonwoven fabric have had to be separately fastened with a film or an adhesive bandage with an adhesive, thereby hindering quick treatment. Also, since a film is used in order to fix alginate fibers, the opening of the wound would result in being dampened when moisture permeability of the film is low. In addition, a covering material for a wound made of an alginate fiber absorbs body fluids to be gelated, thereby showing a view that the covering material has an effect of arresting of bleeding, and an effect of mitigating pain, thereby keeping a wet state appropriate for promoting the treatment. The nonwoven fabric using these fibrous alginates absorbs body fluids oozing from an opening of a wound. Therefore, while the nonwoven fabric is certainly swollen to keep the opening of the wound in a wet state, the effect of arresting of bleeding or the effect of mitigating pain to promote the treatment can hardly said to be sufficient. Rather, the alginate fibers retain the body fluids and are less likely to be released, so that the opening of the wound is dampened in many cases. As described above, many of the covering materials that have been presently used have a disadvantage that an opening of a wound is likely to be dampened.

Accordingly, another object of the present invention is to provide a covering material for a wound, having the functions of quickly drying an opening of a wound, and mitigating pain, thereby promoting cure.

Disadvantages of Conventional Insulation Substrates or Conventional Coating Materials for Semiconductor Devices In above-mentioned semiconductor device formed by using a resin into which amorphous silica-based even-sized particles are embedded, the adhesion between the amorphous silica-based even-sized particles and the resin is worsened while the hygroscopicity is improved. For example, in the case of a premolding-type semiconductor device, an insulation substrate made of a resin is bent upon mounting semiconductor elements on the insulation substrate made of a resin, so that a positioning slippage of the semiconductor elements is caused. Consequently, the semiconductor device has a disadvantage that a connection failure of bonding wire is undesirably generated upon wire bonding with a bonding machine. In addition, in the mold-type semiconductor device, since a semiconductor is bent, there are some disadvantages that the bonding wire fixed with the coating material is undesirably snapped to be disconnected, thereby undesirably generating connection failure.

Accordingly, another object of the present invention is to provide an insulation substrate or a coating material, having excellent moisture tolerance and little bent, and to provide a semiconductor device having fewer snapping of the electrode of the semiconductor element and the bonding wire due to moisture and bent, thereby making it possible to work a semiconductor element normally and stably for a long period of time.

Disadvantages of Conventional Cosmetics

In the above-mentioned cosmetics, while sticky feel immediately after use can be suppressed to a certain extent, sufficient effects cannot be obtained for sticky feel upon sweating, or sticky feel after sweating and drying. Therefore, the development of an antiperspirant having excellent feel of use that does not give sticky feel upon sweating and sticky feel after sweating and drying has been desired.

Accordingly, another object of the present invention is to provide cosmetics having excellent water breathability, i.e. high hygroscopicity and quick moisture-releasing property.

Disadvantages of Conventional Inkjet Recording Media

In conventional recording sheets, disadvantages such as increase in ink absorbability, generation of bleeding, and light fastness and water resistance comparable to those of a film photo have not yet been eliminated.

In addition, a recording sheet comprising an ink receptor layer formed on a coating paper also has a disadvantage that curling due to a humidity change is remarkable, and there has not been a means of effectively eliminating this disadvantage.

Accordingly, another object of the present invention is to provide an inkjet recording medium having excellent curling controlling property even under conditions of low humidity to high humidity, and having excellent ink absorbability, light fastness and water resistance.

Disadvantages of Conventional Synthetic Fibers

Even if ΔMR, which is a moisture-absorption parameter after controlling moisture for a very long period of time of 24 hours, approximates that of cotton, the above-mentioned synthetic fiber has a far slower moisture-absorbing rate than a natural fiber cotton, so that the synthetic fiber is substantially the same as if the synthetic fibers are allowed to stand for a long period of time in a state of high humidity. Therefore, hygroscopicity could not be realized, so that unpleasant "damp feel" could not be eliminated.

Accordingly, another object of the present invention is to provide a composition containing a synthetic fiber having excellent water breathability, namely both high hygroscopicity and quick moisture-releasing property.

Means to Solve the Problems

Specifically, the gist of the present invention relates to:
[1] a moisture- or protein-adsorbability imparting agent, comprising a porous silica having a hexagonal pore structure, an average pore size of from 0.8 to 20 nm, an average particle size of 50 nm to 100 μm, a specific surface area of from 400 to 2000 m$^2$/g, and a pore volume of from 0.1 to 3.0 cm$^3$/g;
[2] a material having adsorbability of moisture or a protein, comprising the moisture- or protein-adsorbability imparting agent of the above [1]; and
[3] use of the moisture- or protein-adsorbability imparting agent of the above [1] for imparting a moisture- or protein-adsorbability to a material selected from the group consisting of food wrapping materials; filtration aid agents; sanitary articles; compositions containing a synthetic resin; moisture-controlled material; covering materials for wounds; insulation substrates; coating materials for semiconductor devices; cosmetics; inkjet recording media; and compositions containing synthetic fibers.

Effects of the Invention

According to the present invention, a moisture- or protein-adsorbability imparting agent, which has both high adsorbability and desorbability can be provided.

According to the present invention, a food wrapping material which is capable of finishing a steaming warm food such as a soft, steam bun with meat fillings, or bread hot from the oven in a state that does not lose the taste of the food by absorbing excessive moisture or oil coming out from the food when heating the food with a microwave oven or wrapping the food, and at the same time capable of preventing hands, ovens, clothes and the like from being soiled can be provided.

According to the present invention, a filtration aid having more excellent adsorbability than that of the conventional products, that only removes a protein or the like unnecessary in a manufactured article, but not the necessary protein, further having even more improved filtration properties such as filtration speed and strength as a filter than those of the conventional silica gels can be provided. Furthermore, according to the present invention, a filtration aid having excellent filtration performance, such as excellent filtration properties and improved adsorption speed by improving a filtration speed can be provided.

According to the present invention, a sanitary article capable of satisfying both an odor-controlling function and a moisture-permeable function, capable of quickly discharging water vapor, while preventing the release of a foul odor generated from an absorbed liquid can be provided.

According to the present invention, a composition containing a synthetic resin, the composition having excellent water breathability, which is suitable for obtaining a film that is less likely to generate dew condensation and a synthetic leather having a moist texture can be provided. The manufactured article obtained from the composition containing a synthetic resin of the present invention has a high hygroscopicity under high-humidity conditions, and an excellent moisture-releasing property under low-humidity conditions, thereby having an excellent water breathability. Therefore, when the manufactured article is in the form of a film such as a wrapping material, dew condensation is less likely to be formed, and the manufactured article shows excellent dimensional stability against change in humidity. In addition, since a moist feel of quality distinctively owned by leather is obtained when the manufactured article is formed into synthetic leather, the manufactured article is useful as a material for synthetic leather.

According to the present invention, a moisture-controlled material that has a moisture-controlled function for wide applications, in which moisture in the living space is autonomously absorbed and desorbed, thereby controlling humidity in the living environment in an optimal state in an energy conservation manner, and at the same time having a deodorizing function can be provided.

According to the present invention, a covering material for a wound, having the functions of quickly drying an opening of a wound, and mitigating pain, thereby promoting cure can be provided.

According to the present invention, a composition capable of providing an insulation substrate or a coating material, having excellent moisture tolerance and little bent can be provided, and a semiconductor device having fewer snapping of the electrode of the semiconductor element and the bonding wire due to moisture and bent, thereby making it possible to work a semiconductor element normally and stably for a long period of time can be provided.

According to the present invention, cosmetics having excellent moisture breathability, i.e. high hygroscopicity and quick moisture-releasing property, and excellent feel of use can be provided.

According to the present invention, an inkjet recording medium having excellent curling controlling property even under conditions of low humidity to high humidity, and having excellent ink absorbability, light fastness and water resistance can be provided.

According to the present invention, a composition containing a synthetic fiber having excellent moisture breathability, namely both high hygroscopicity and quick moisture-releasing property can be provided.

BRIEF DESCRIPTION OF THE DRAWINGS

FIG. 1 is a cross-sectional view showing one example of a sanitary napkin.

FIG. 2 is a graph showing water breathability of various materials.

EXPLANATION OF NUMERALS

| | |
|---|---|
| 1 | sanitary napkin |
| 2 | top sheet |
| 3 | absorbent |
| 4 | back sheet |

BEST MODE FOR CARRYING OUT THE INVENTION

One of the features of the moisture- or protein-adsorbability imparting agent of the present invention (hereinafter simply referred to "imparting agent") resides in that the agent comprising a porous silica having a specified-pore structure, a specified pore size, a specified average particle size, a specified specific surface area, and a specified pore volume. Since the agent has the features, the imparting agent of the present invention exhibits surprising effects that the agent more easily adsorbs moisture or a protein, and that moisture is desorbed.

The porous silica used in the present invention refers to a substance containing silicon oxide having a porous structure as a main component.

The porous silica used in the present invention has a pore forming a hexagonal structure. Specifically, the porous silica has an X-ray diffraction pattern in a hexagonal form, or a hexagonal structure can be observed when pores of the porous silica is directly observed with a transmission electron microscope (for example, JEM-200CX, manufactured by JEOL). Here, the X-ray diffraction pattern can be determined with a fully automatic X-ray diffractometer (RINT ULTIMA II, manufactured by Rigaku Denki K.K.).

The porous silica used in the present invention has pores having an average pore size of from 0.8 to 20 nm, and its preferred range is properly set depending upon the material used in the imparting agent of the present invention. The pore size distribution is not particularly limited, and it is preferable that 60% or more of pores falls within the range of ±40% of the pore showing a maximum peak in the pore size distribution curve.

The porous silica used in the present invention has a specific surface area of from 400 to 2000 $m^2/g$, and its preferred range is properly set depending upon the material used in the imparting agent of the present invention.

The porous silica used in the present invention has a pore volume of from 0.1 to 3.0 $cm^3/g$, and its preferred range is properly set depending upon the material used in the imparting agent of the present invention.

The average pore size, the specific surface area and the pore volume of the porous silica in the present invention can be obtained by known methods. Specifically, the average pore size, the specific surface area and the pore volume can be calculated from a nitrogen adsorption isotherm. More specifically, the average pore size can calculated from known BJH method, BET method, t method, DFT method, or the like; the specific surface area can be calculated from known BET method, t method, α method, or the like; and the pore volume can be calculated from known BJH method, BET method, t method, or the like.

The porous silica used in the present invention has an average particle size of from 50 nm to 100 μm, and its preferred range is properly set depending upon the material used in the imparting agent of the present invention. Here, the average particle size can be determined by a laser method or a dynamic light scattering method. Here, in the present specification, a case of those simply described as "average particle size" refers to an average particle size of secondary particles, while a case of those described as "average particle size of primary particles" refers to an average particle size of the primary particles of the porous silica.

The porous silica used in the present invention contains primary particles having an average particle size of preferably from 30 to 500 nm, more preferably from 30 to 200 nm, even more preferably from 30 to 100 nm, and even still more preferably from 30 to 50 nm, from the viewpoint of adsorbing water or a protein. Here, the average particle size of the primary particles can be determined by observing with a transmission electron microscope.

The porous silica used in the present invention shows an X-ray diffraction pattern having one or more peaks at a diffraction angle corresponding to a d value of preferably greater than 2.0 nm, a d value of more preferably 2.0 to 20.0 nm, a d value of even more preferably from 2.0 to 5.0 nm, and a d value of even still more preferably from 3.0 to 5.0 nm, from the viewpoint of amount of moisture or protein adsorption and adsorption sustainability. Further, it is desired that the porous silica used in the present invention shows an X-ray diffraction pattern having one or more peaks at a diffraction angle corresponding to a d value of greater than 2.0 nm, and wherein there exist no peaks at a diffraction angle corresponding to a d value smaller than 1.0 nm that have a relative intensity of greater than 200%, preferably greater than 100%, more preferably greater than 50%, even more preferably greater than 30%, and even still more preferably greater than 10%, of the most intensive peak among the peaks, from the viewpoint of amount of water or protein adsorption and adsorption sustainability. Here, the X-ray diffraction pattern and the d value can be determined with a fully automatic X-ray diffractometer (RINT ULTIMA II, manufactured by Rigaku Denki K.K.).

In the test of chlorophyll adsorption shown in Examples set forth below, the porous silica used in the present invention has an amount of chlorophyll adsorption of preferably 5 mg or more, more preferably 10 mg or more, even more preferably 15 mg or more, and even still more preferably 20 mg or more, per 100 mg of the porous silica, from the viewpoint of adsorbing moisture or a protein. Also, it is preferable that the porous silica has an amount of chlorophyll adsorption of 100 mg or less, per 100 mg of the porous silica. Therefore, the porous silica used in the present invention has an amount of chlorophyll adsorption of preferably from 5 to 100 mg, more preferably from 10 to 100 mg, even more preferably from 15 to 100 mg, and even still more preferably from 20 to 100 mg, per 100 mg of the porous silica.

The method for preparing a porous silica used in this embodiment is not particularly limited, and includes, for example, a process comprising mixing an inorganic raw material with an organic raw material to react the mixture, thereby forming a complex of the organic substance and the inorganic substance in which the organic substance is used as a template, and the backbone of the inorganic substance is formed in the surrounding of the organic substance, and removing the organic substance from the resulting complex.

The inorganic raw material is not particularly limited as long as the substance contains silicon. The silicon-containing substance includes, for example, substances containing a silicate such as a layered silicate or a non-layered silicate, and substances containing silicon other than the silicate. The layered silicate includes kanemite ($NaHSi_2O_5.3H_2O$), sodium disilicate crystals ($Na_2Si_2O_5$), makatite ($NaHSi_4O_9.5H_2O$), ilerite ($NaHSi_8O_{17}.XH_2O$), magadiite ($Na_2HSi_{14}O_{29}.XH_2O$), kenyaite ($Na_2HSi_{20}O_{41}.XH_2O$) and the like. The non-layered silicate includes water glass (sodium silicate), glass, amorphous sodium silicate, and silicon alkoxides such as tetraethoxysilane (TEOS), tetramethylammonium (TMA) silicate and tetraethyl orthosilicate, and the like. In addition, the substance containing silicon other than the silicate includes silica, oxide of silica, silica-metal composite oxides and the like. These inorganic raw materials may be used alone or in admixture of two or more kinds.

The organic raw material includes cationic, anionic, amphoteric, and nonionic surfactants, and the like. The organic raw material can be used alone or in admixture of two or more kinds.

The cationic surfactant includes primary amine salts, secondary amine salts, tertiary amine salts, quaternary amine salts and the like. Among them, the quaternary amine salts are preferable. Since an amine salt has poor dispersibility in an alkaline region, the amine salt is used only where the preparation condition is acidic. However, the quaternary amine salt can be used in both cases where the preparation condition is alkaline and acidic.

The quaternary amine salt includes an alkyl(8 to 22 carbon atoms)trimethylammonium salt such as octyltrimethylammonium chloride, octyltrimethylammonium bromide, octyltrimethylammonium hydroxide, decyltrimethylammonium chloride, decyltrimethylammonium bromide, decyltrimethylammonium hydroxide, dodecyltrimethylammonium chloride, dodecyltrimethylammonium bromide, dodecyltrimethylammonium hydroxide, hexadecyltrimethylammonium chloride, hexadecyltrimethylammonium bromide, hexadecyltrimethylammonium hydroxide, octadecyltrimethylammonium chloride, octadecyltrimethylammonium bromide, octadecyltrimethylammonium hydroxide, behenyltrimethylammonium chloride, behenyltrimethylammonium bromide, behenyltrimethylammonium hydroxide, tetradecyltrimethylammonium chloride, tetradecyltrimethylammonium bromide, tetradecyltrimethylammonium hydroxide, benzyltrimethylammonium chloride, benzyltrimethylammonium bromide, benzyltrimethylammonium hydroxide, and the like. These quaternary amine salts can be used alone or in admixture of two or more kinds.

The anionic surfactant includes carboxylates, sulfuric ester salts, sulfonates, phosphoric ester salts and the like. Among them, soaps, higher alcohol sulfuric ester salts, higher alkyl ether sulfuric ester salts, sulfated oils, sulfated fatty acid esters, sulfated olefins, alkylbenzenesulfonates, alkylnaphthalenesulfonates, paraffinic sulfonates and higher alcohol phosphoric ester salts are preferable. These anionic surfactants can be used alone or in admixture of two or more kinds.

The amphoteric surfactant includes sodium laurylaminopropionate, stearyldimethylbetaine, lauryldihydroxyethylbetaine and the like are preferable. These amphoteric surfactants can be used alone or in admixture of two or more kinds.

The nonionic surfactant includes those in the form of ethers such as polyoxyethylene alkyl ethers, polyoxyethylene secondary alcohol ethers, polyoxyethylene alkyl phenyl ethers, polyoxyethylene sterol ethers, polyoxyethylene lanolin acid derivatives, polyoxyethylene polyoxypropylene alkyl ethers, polypropylene glycol and polyethylene glycol; and those in the form of containing nitrogen such as polyoxyethylene alkylamine. These nonionic surfactants can be used alone or in admixture of two or more kinds.

When silicon oxides such as silica ($SiO_2$), are used as the inorganic raw material, the pores can be formed by firstly forming a layered silicate such as kanemite, inserting a template made of an organic raw material between the layers, connecting the interlayers where the template does not exist with silicate molecules, and thereafter removing the template therefrom. In addition, when water glass is used, pores can be formed by gathering silicate monomers in the surrounding of the template, polymerizing the monomers to form silica, and thereafter removing the template therefrom.

When a surfactant is used as an organic raw material and pores are formed by using the surfactant as a template, micelles thereof can be utilized as the template. In addition, by controlling the alkyl chain length of the surfactant, the diameter of the template changes, whereby the size of the pores formed can also be controlled. Furthermore, a relatively hydrophobic molecule such as trimethylbenzene or tripropylbenzene is added together with the surfactant, so that the micelles expand, whereby pores having even larger sizes can be formed. Pores having an optimal size can be formed by utilizing these methods.

When mixing the inorganic raw material with the organic raw material, a proper solvent may be used. The solvent is not particularly limited, and includes water, alcohols and the like.

The process for mixing the inorganic raw material with the organic raw material is not particularly limited. A process comprising adding ion-exchanged water in a weight ratio of 2-folds amount or more to the inorganic raw material, thereafter stirring at 40° to 80° C. for 1 hour or more, and thereafter adding an organic raw material thereto is preferable.

A mixing ratio of the inorganic raw material to the organic raw material is not particularly limited. A ratio of the inorganic raw material:organic raw material (weight ratio) is preferably from 0.1:1 to 5:1 and more preferably from 0.1:1 to 3:1.

The reaction of the inorganic raw material and the organic raw material is not particularly limited. It is preferable that the reaction is carried out by stirring the mixture preferably at a pH of 11 or more for 1 hour or more, adjusting its pH to 8.0 to 9.0, and thereafter reacting the components for 1 hour or more.

The method of removing the organic substance from the complex of the organic substance and the inorganic substance includes a method comprising collecting the complex by filtration, washing the complex with water or the like, drying the complex, and thereafter baking the dried complex at a temperature from 400° to 600° C.; and a method comprising extracting the organic substance with an organic solvent or the like.

It is preferable that the porous silica is further subjected to cross-linking with a metal, from the viewpoint of working stability. The metal to be cross-linked is not particularly limited, and includes, for example, Mn, Co, Ni, Fe, Mg, Al, Cr, Ga, Ge, Ti, and the like, and Al is preferable, from the viewpoint of working stability.

The cross-linking with a metal can be carried out by, for example, dissolving a metal salt in water or the like, thereafter mixing the solution with the porous silica, and further drying the mixture as occasion demands.

The porous silica obtained in the manner described above is, for example, represented by the general formula (1):

$$M_xAl_ySi_zO_2 \quad (1)$$

wherein M is a metal element other than Al, x is 0 or more and 1 or less, y is 0 or more and 1 or less, and z is greater than 0 and 1 or less. M is one or more kinds of metal elements used in cross-linking with a metal other than Al, and includes, for example, Mn, Co, Ni, Fe, Mg, Al, Cr, Ga, Ge, Ti and the like. When M is composed of two or more kinds of cations, the sum of the two or more kinds of the metal elements may be x.

It is preferable that the porous silica is further bound and supported to an organic substance-containing silicon compound, from the viewpoint of adsorbing water or a protein. The organic substance-containing silicon compound includes amino group-containing silicon compounds, mercapto group-containing silicon compounds, and the like. The amino group-containing silicon compound is not particularly limited, and there may be used those compounds having one or more amino groups and one binding functional group subjected to binding with a hydroxyl group on the surface of the porous substance, including, for example, in addition to (3-aminopropyl)methylethoxysilane, those having two or more amino groups such as bis(3-aminopropyl)methyl ethoxysilane and tris(3-aminopropyl)ethoxysilane, and the like. The method of binding and supporting the amino group-containing silicon compound to the porous silica is not particularly limited. For example, the amino group-containing silicon compound is dispersed in water or the like while mixing, to be supported to the porous silica, and the product may be further dried as occasion demands. The mercapto group-containing silicon compound includes 3-mercaptopropylmethyl dimethoxysilane, 3-mercaptopropyl trimethoxysilane, and the like.

The content of the porous silica in the imparting agent is properly selected depending upon the materials used. The content is preferably from 0.001 to 100% by weight, more preferably from 0.1 to 100% by weight, even more preferably from 0.5 to 100% by weight, and even still more preferably from 1 to 100% by weight, from the viewpoint of adsorbing moisture or a protein.

It is preferable that the imparting agent of the present invention further contains an emulsifying agent, from the viewpoint of adsorbing moisture or a protein, and it is more preferable that the imparting agent contains an emulsifying agent and lecithin. In this case, it is more preferable that the emulsifying agent and lecithin are selectively adsorbed to the external of the porous silica, without having them getting into the pores.

The emulsifying agent is a fatty acid ester having preferably 12 or more carbon atoms, more preferably 14 or more carbon atoms, even more preferably 16 or more carbon atoms, and even still more preferably 18 or more carbon atoms, from the viewpoint of selectively adsorbing an emulsifying agent to the external of the porous silica. The emulsifying agent includes, for example, glycerol fatty acid esters, polyglycerol fatty acid esters, sucrose fatty acid esters, sorbitan fatty acid esters, propylene glycol fatty acid esters, and the like. Among them, a polyglycerol fatty acid ester formed by esterification between a polyglycerol and a fatty acid is preferable. In addition, the polyglycerol constituting the polyglycerol fatty acid ester has an average degree of polymerization of preferably 2 or more, more preferably 3 or more, and even more preferably 4 or more, from the viewpoint of selectively adsorbing an emulsifying agent to the external of the porous silica.

In addition, among the above-mentioned polyglycerol fatty acid esters, a polyglycerol fatty acid formed by esterification between 2 to 10 molecules of a fatty acid and a polyglycerol is preferable, and a polyglycerol fatty acid ester formed by esterification between a condensate formed by esterification of 2 to 10 molecules of fatty acids, and a polyglycerol is even more preferable, from the viewpoint of selectively adsorbing an emulsifying agent to the external of the porous silica.

The emulsifying agent can be selected depending upon a subject to be adsorbed to the porous silica, such as moisture or a protein, and two or more kinds of the emulsifying agents can be used in admixture as occasion demands.

It is preferable that the imparting agent contains a polyglycerol fatty acid formed by esterification between a polyglycerol having an average degree of polymerization of 3 or more and a fatty acid, and it is even more preferable that the imparting agent contains the polyglycerol fatty acid and lecithin, from the viewpoint of adsorbing water or a protein. Here, the average degree of polymerization of the polyglycerol of the polyglycerol fatty acid ester can be obtained by determining a hydroxyl value.

As the above-mentioned polyglycerol fatty acid ester, there can be utilized, for example, SUNSOFT A-141E, SUNFAT PS-66, SUNFAT PS-68, SUNSOFT Q-185S, SUNSOFT Q-1810S, SUNSOFT Q-175S, SUNSOFT Q-1710S, SUNSOFT A-173E, SUNSOFT A-183E, SUNSOFT A-186E, SUNSOFT No. 818DG, SUNSOFT No. 818H, SUNSOFT No. 818SK, SUNSOFT No. 818TY, each manufactured by Taiyo Kagaku Co., Ltd. or the like.

The above-mentioned lecithin is a general name of a commercial product, and is a generic name for phospholipids. In addition, an enzymatically decomposed lecithin obtained by enzymatically decomposing lecithin is preferable. The enzymatically decomposed lecithin as used herein is a monoacyl glycerolipid typically including lysophatidylcholine, lysophatidylethanolamine, lysophatidylinositol, and lysophatidylserine, each being obtained by hydrolyzing a fatty acid ester moiety of a vegetable lecithin or egg yolk lecithin with a phospholipase A in a limiting manner; and one or more members selected from the group consisting of phosphatidic acid, lysophosphatidic acid, phosphatidylglycerol and lysophosphatidylglycerol, each being formed using a phospholipase D. Lysophatidylcholine, lysophatidylethanolamine, and lysophatidylserine are preferable, and lysophatidylcholine is more preferable. The phospholipase used in the enzymatic decomposition may be any of those having phospholipase A and/or D activity, regardless of the derivations, including animal origins such as porcine pancreas, plant origins such as cabbage, microbial origins such as molds, and the like As the above-mentioned lecithin, there can be utilized, for example, SUNLECITHIN A, SUNLECITHIN W-1, SUNLECITHIN L-6, SUNLECITHIN L-8, SUNLECITHIN A-1, SUNLECITHIN A-2, SUNLECITHIN L-3C, SUNLECI- THIN L-61, SUNLECITHIN L-3E, each manufactured by Taiyo Kagaku Co., Ltd., or the like.

The content of the above-mentioned emulsifying agent in the imparting agent of the present invention is preferably from 0.01 to 50% by weight, and more preferably from 0.1 to 30% by weight, in a case where the emulsifying agent is used alone; and the content is preferably 0.01 to 50% by weight in total, and more preferably from 0.01 to 30% by weight in total, in a case where the emulsifying agent is used together with lecithin. The weight ratio of the emulsifying agent to lecithin (emulsifying agent:lecithin) is preferably from 1:0.1 to 1:1, and more preferably from 1:0.5 to 1:1.

The imparting agent of the present invention can be prepared by, for example, mixing the above components.

The imparting agent prepared in the manner described above can be added to various materials, and the materials to which the imparting agent is added even more improves in adsorbability of moisture or a protein. Therefore, the present invention also provides a material having adsorbability of moisture or a protein, containing the above-mentioned imparting agent.

The materials include food wrapping materials; filtration aids; sanitary articles; compositions each containing a synthetic resin; moisture-controlled material; covering materials for wounds; insulation substrates; coating materials for semiconductor devices; cosmetics; inkjet recording media; and compositions containing synthetic fibers.

Each of the embodiments will be explained hereinbelow.

Embodiment 1

Food Wrapping Materials

The food wrapping material of this embodiment contains the above-mentioned imparting agent.

The porous silica used in this embodiment has pores having an average pore size of preferably from 1 to 10 nm, and more preferably from 2 to 5 nm, from the viewpoint of miscibility with other raw materials.

The porous silica used in this embodiment has a pore volume of preferably from 0.2 to 2.0 $cm^3/g$, from the viewpoint of adsorption efficiency of moisture or oil.

The porous silica used in this embodiment has a specific surface area of preferably from 400 to 1500 $m^2/g$, and more preferably from 600 to 1200 $m^2/g$, from the viewpoint of adsorption efficiency of moisture or oil.

The porous silica used in this embodiment has an average particle size of preferably from 50 nm to 10 μm, more preferably from 50 to 500 nm, and even more preferably from 50 to 300 nm, from the viewpoint of adsorption efficiency of moisture or oil.

The food wrapping materials of this embodiment include, for example, various wrapping bags such as flat bag, pillow bag, gazette bag, and standing pouch; container body such as boxes; lid materials; sheets for wrapping; and the like.

The constitution of the food wrapping material in this embodiment is not particularly limited. The constitution includes, for example, those in which a resin or a paper film, such as a liquid-permeable sheet, an absorbent sheet, a water-impermeable sheet, an air-impermeable sheet, an air-permeable (moisture-permeable) sheet, is used alone; and laminate sheets composed of a laminates of one or more kinds of these resins or paper films. Those which are composed of a laminate comprising an air-permeable sheet in an outer layer, an absorbent sheet in an inside thereof, and a liquid-permeable sheet in a further inside thereof is preferable.

The outermost layer of the food wrapping material in this embodiment is not particularly limited, as long as the outermost layer serves to prevent leakage of excess oil or moisture that is generated in the internal to the external when wrapping a food and cooking with a microwave oven or the like, and to prevent burns or the like when taking out the food from a microwave oven or the like after cooking, or eating the food. The outermost layer as described above includes, for example, papers; sheets produced by thinly coating polyethylene or polypropylene resin to paper; sheets made of resins such as polypropylene, polyethylene, polyesters, polyamides, and polyvinyl alcohols; resin foam sheets of these resins or polystyrene; nonwoven fabric sheets obtained by flash spinning method; sheets having moisture-permeable, waterproof property, such as microporous films; and the like. Among them, the sheets produced by thinly coating a polyolefin resin such as polyethylene or polypropylene resin to paper are preferable, from the viewpoint that heat is less likely to be conducted, and leakage of oil or water to the external is prevented. Further, it is preferable to have air permeability (moisture permeability), and those which are subjected to punching working to a part of a sheet may be used. It is preferable that the extent of the moisture permeability is properly selected depending upon the amount of water generated from the food, for the purpose of expelling from a sheet or sac excess water vapor generated upon cooking with a microwave oven or the like.

The absorbent sheet in this embodiment is not particularly limited, as long as the absorbent sheet is a sheet-like product having water absorbency or oil absorbency. For example, there can be used, paper; a nonwoven fabric made of natural fibers and synthetic fibers; a sponge; or the like. Among these absorbent sheets, papers made of pulp, and nonwoven fabrics made of cellulose fibers such as rayon are preferable, from the viewpoint of water absorbency, handling ability and costs.

An innermost layer of the wrapping material for foods in this embodiment is not particularly limited, as long as the innermost layer has a liquid permeability having the functions of contacting with the food and quickly permeating water vapor or dripping water generated from the food to be allowed to migrate to an absorbent sheet, and suppressing re-wetting the food side with moisture or the like absorbed in the absorbent sheet to a minimum level. The material having excellent liquid permeability for water vapor or dripping water includes, for example, nonwoven fabrics made of synthetic fibers such as polyethylene, polypropylene or polyester; nonwoven fabrics made of composite fibers of these synthetic fibers, mesh-type knitted articles or textile; and the like. Use of a nonwoven fabric made of a thermoplastic resin would be advantageous during the production of a sheet or upon working into the production of bags.

The food wrapping material of this embodiment can be produced by mixing the raw material and the above-mentioned imparting agent upon the production of these sheets, or coating the produced sheets with or immersing the sheets in the above-mentioned imparting agent. The content of the above-mentioned imparting agent in the food wrapping material of this embodiment is preferably from 0.1 to 70% by weight, and more preferably from 1 to 60% by weight, from the viewpoint of adsorption efficiency of water or oil.

The sheet containing the above-mentioned imparting agent can be used in one or more kinds of the sheets constituting the food wrapping material. For example, when the imparting agent is used in an outer layer, which is an air-permeable (moisture-permeable) sheet, since the porous silica has moisture-controlling property, permeation of the water vapor to an extent that is more than needed is prevented, so that the content can be prevented from being dried. When the imparting agent is used in an absorbent sheet, water absorbency and oil absorbency of the absorbent sheet can be improved. When the imparting agent is used in an inner layer, which is a liquid-permeable sheet, the adhered water vapor and oil can be quickly absorbed, and at the same time the moisture or the like absorbed to the absorbent sheet is adsorbed to the porous silica when the moisture re-wets to the food side, whereby the food can be prevented from being wetted.

In addition, the absorbent sheet containing the above-mentioned imparting agent can be used as a cookie sheet in the form of a sheet as it is.

Embodiment 2

Filtration Aid

The filtration aid of this embodiment contains the above-mentioned imparting agent.

The porous silica used in this embodiment has pores having an average pore size of more preferably from 1 to 10 nm, and more preferably from 2 to 5 nm, from the viewpoint of adsorbing a specified protein which is causative of grout.

The porous silica used in this embodiment has a pore volume of preferably from 0.2 to 2.0 $cm^3/g$, more preferably from 0.5 to 2.0 $cm^3/g$, and even more preferably from 0.8 to 2.0 $cm^3/g$, from the viewpoint of adsorption volume.

The porous silica used in this embodiment has a specific surface area of preferably from 400 to 1500 $m^2/g$, more preferably from 600 to 1200 $m^2/g$, and even more preferably from 800 to 1200 $m^2/g$, from the viewpoint of adsorption volume.

The porous silica used in this embodiment has an average particle size of preferably from 50 nm to 10 μm, more preferably from 50 to 500 nm, and even more preferably from 50 to 300 nm.

In the filtration aid of this embodiment, the imparting agent may be used as it is.

The filtration aid of this embodiment can be applied to either one or both of the method in which a filtration aid is used by pre-coating the filtration aid to a filtration material, and method in which a filtration aid is used in the form of a body feed to a substance to be filtered.

The applications for the filtration aid of this embodiment are not particularly limited. The filtration aid is useful as a selective adsorbent of a protein which is causative of sediment to a brewed article such as a brewed alcohol beverage, such as sake, a sweet sake, or beer.

Embodiment 3

Sanitary Article

The sanitary article of this embodiment contains the above-mentioned imparting agent.

The porous silica used in this embodiment has pores having an average pore size of preferably from 1 to 10 nm, and more preferably from 2 to 5 nm.

The porous silica used in this embodiment has a pore volume of preferably from 0.2 to 2.0 $cm^3/g$, from the viewpoint of adsorption volume.

The porous silica used in this embodiment has a specific surface area of preferably from 400 to 1500 $m^2/g$, and more preferably from 600 to 1200 $m^2/g$, from the viewpoint of adsorption volume.

The porous silica used in this embodiment has a specific surface area of preferably from 50 nm to 10 μm, more preferably from 50 to 500 nm, and even more preferably from 50 to 300 nm.

The sanitary article in this embodiment is not particularly limited. The sanitary article includes, for example, sanitary napkins, disposable diapers, incontinence pads, panty liners, sheet for pets, and the like.

The structure of the sanitary article in this embodiment is not particularly limited. The sanitary article has a conventionally well known structure, in which the sanitary article comprises a surface sheet capable of permeating a body fluid, a body fluid-impermeable back sheet for blocking permeation of the body fluid, and an absorbent body included between both the sheets. In the surface sheet, the back sheet and the absorbent body, various materials, shapes, and structures that are conventionally used in these kinds of articles can be used, and are not particularly limited. The absorbent body is generally made of crushed pulp, and may be a mixture of body fluid-absorbable polymer particles.

The method of using the above-mentioned imparting agent in the sanitary article of this embodiment is not particularly limited. The method includes a method of including the imparting agent in the sheet or absorbent body constituting the sanitary article, preferably a method of including the imparting agent in the sheet constituting the sanitary article, and even more preferably a back sheet, or a sheet layer comprising a laminate of back sheets.

The content of the above-mentioned imparting agent used in this embodiment in the sanitary article is preferably from 0.001 to 30% by weight, more preferably from 0.001 to 20% by weight, even more preferably from 0.001 to 10% by weight, and even still more preferably from 0.001 to 5% by weight, from the viewpoint of water breathability.

The method for producing a sheet constituting the sanitary article in this embodiment is not particularly limited, and conventionally well known methods may be employed. For example, in the case of a resin film, a desired film can be obtained by not adding or adding one or more kinds of various additives such as a hydrophilic agent, a skincare material, a moisturizer, a colorant, an inorganic raw material, an antioxidant (anti-aging agent), a thermal stabilizer, a photostabilizer, or an ultraviolet absorbent; further adding the above-mentioned imparting agent thereto; kneading the obtained mixture; forming a film by a conventional film forming method, such as T die method or inflation method to give a film; and thereafter stretching the resulting film in a single-screw direction or a double-screw direction according to a conventional stretching method. In the case of a nonwoven fabric, the nonwoven fabric is made of polyethylene, polypropylene, or polyethylene/polypropylene composite, and a desired film can be obtained by coating an additive on the surface of the fibers.

The hydrophilic agent includes glycerol, glycerol fatty acid esters, lipophilic glycerol monooleate, lipophilic glycerol monostearate, polyethylene glycols, polyoxyethylene lauryl ethers, sorbitan monooleate, sorbitan monostearate, polyethylene glycol monolaurate, and the like. As the skincare material, a formulation agent that is formulated in cosmetics is preferable. The formulation agent includes, for example, moisturizers such as macadamia nut oil cholesteryl derivatives, macadamia nut oil phytostearyl fatty acids, and di(cholesteryl, octyldodecyl)N-lauroyl-L-glutamic acid ester; powders of calcium carbonate, zinc oxide, and the like; aloe extract; *Artemisia princeps* pampan extract; chitosan; silk powders; and the like.

Especially, since the surface sheet directly contacts with the skin of the user, it is preferable to form the surface sheet with a surface material made of a resin film or a nonwoven fabric, that is comfortable on skin, but not limited thereto, and all the surface materials that have been conventional used in this kind of an article for absorbing body fluid can be used. As the resin film that is comfortable on skin, those having a single layered or double layered structure in which an additive selected from the raw materials for cosmetic is formulated, and those having a structure of a perforated film on which a large number of small pores for excellently allowing the body fluid to migrate from the surface side to the absorbent body side are formed are preferable. A single layered film resin is preferably made of a polyethylene, from the viewpoint of moldability into a film, mechanical strength, flexibility and the like. In the case of a double layered film resin, a mixed material in which a film layer on the side of skin is made of a polyethylene, and a film layer on the side of the absorbent body is made of a copolymer of a polyethylene and an ethylene-vinyl acetate copolymer is most suitable. In the film having a double layered structure, the film layer positioned on the side of skin is formulated with an additive. The formulation of the ethylene-vinyl acetate copolymer imparts flexibility to the film, and at the same time heat sealing property is improved so that heat sealing can be carried out at a low temperature, whereby influence to other materials due to heat upon the production into the absorbent article can be prevented.

The formulation of the additive to the resin film is applied by means of kneading. When the perforated film has a small pore size, smooth migration of the fluid would be difficult, so that it is preferable to aim for improvement in migrating property by formulating a hydrophilic agent. A film that is preferable for a back sheet is one obtained by mixing and formulating to a polyolefin-based resin such as a polyethylene with calcium carbonate, ferrous sulfate, zinc oxide, or the like; forming the mixture into a film; stretching the film, thereby forming gaps in the interface of the polyolefin and the powder, because the film has the functions of passing water vapor but not water, and is also provided with air permeability for preventing damp feel that is required in sanitary articles.

Embodiment 4

Composition Containing Synthetic Resin

The composition containing a synthetic resin of this embodiment contains the above-mentioned imparting agent.

The porous silica used in this embodiment has pores having an average pore size of preferably from 1 to 10 nm, and more preferably from 2 to 5 nm.

The porous silica used in this embodiment has a pore volume of preferably from 0.2 to 2.0 cm$^3$/g, from the viewpoint of adsorption volume.

The porous silica used in this embodiment has a specific surface area of preferably from 400 to 1500 m$^2$/g, and more preferably from 600 to 1200 m$^2$/g, from the viewpoint of adsorption volume.

The porous silica used in this embodiment has an average particle size of preferably from 50 nm to 10 μm, more preferably from 50 to 500 nm, and even more preferably from 50 to 300 nm.

Since the porous silica used in this embodiment has the above features, the porous silica has excellent water breathability that moisture is quickly adsorbed under high humidity conditions, and moisture is quickly desorbed under low humidity conditions.

The composition containing a synthetic resin of this embodiment refers to a composition further containing the above-mentioned imparting agent in addition to the conventional synthetic resin. Since the composition may contain a solvent, a surfactant or the like as occasion demands, for the purpose of improving dispersibility.

The synthetic resin usable in this embodiment is not particularly limited, and the synthetic resin may be any of thermoplastic resins and thermosetting resins. Preferably, the synthetic resin includes at least one resin selected from the group consisting of polyvinyl chloride resins, polyurethane resins, polyacrylic resins, polyamide resins, polyester resins, polyamino acid-based resins, polyolefin-based resins, and epoxy resins.

The polyvinyl chloride resin also includes, besides the homopolymer of vinyl chloride, for example, vinyl chloride copolymers, such as vinyl chloride-vinyl acetate copolymers, vinyl chloride-vinylidene chloride copolymers, vinyl chloride-ethylene copolymers, and copolymers prepared by graft-polymerizing vinyl chloride to ethylene-vinyl acetate copolymers.

The polyurethane resin is a resin prepared from a polyisocyanate (a compound having two or more isocyanate groups (—NCO) in one molecule) and a polyol (a compound having two or more active hydrogen groups (—OH or —NH$_2$) in one molecule). The polyisocyanate includes tolylene diisocyanate, diphenylmethane diisocyanate, polymethylene polyphenyl polyisocyanates, tolidine diisocyanate, naphthalene diisocyanate, hexamethylene diisocyanate, isophorone diisocyanate, xylylene diisocyanate, hydrogenated xylylene diisocyanate, dicyclohexylmethane diisocyanate, and the like. In addition, the polyol includes polypropylene glycol and modified products thereof, polytetramethylene glycol and modified products thereof, polymer-polyols (those prepared by subjecting acrylonitrile/styrene to radical polymerization in polypropylene glycol), polyether-polyamines, condensed polyester-polyols, lactone-based polyester-polyols, polycarbonate-polyols, polybutadiene-polyols, acryl-polyols, partially saponified ethylene-vinyl acetate copolymers, phenolic polyols, phosphorus-containing polyols, halogen-containing polyols, and the like.

The polyamide resin is a resin prepared by polycondensation of a dicarboxylic acid and a diamine, polycondensation of ω-aminocarboxylic acids, ring-opening polymerization of lactam composed of ω-aminocarboxylic acids, or the like. The polyamide resin includes a polycondensate of tetramethylene diamine and a salt of adipic acid (nylon 46), a ring-opening polymer of ε-caprolactam or ε-aminocaproic acid (nylon 6), a polycondensate of hexamethylenediamine and a salt of adipic acid (nylon 66), a polycondensate of hexamethylenediamine and a salt of sebacic acid (nylon 610), a polycondensate of hexamethylenediamine and a salt of dodecanediacid (nylon 612), a ring-opening polymer of ω-aminoundecanoic acid (nylon 11), a ring-opening polymer of ω-laurolactam or ω-aminododecanoic acid (nylon 12), and the like.

The polyester resin is a resin obtained by a polycondensation reaction of a dibasic acid or dibasic acid ester, with a dihydric alcohol, in which the resin has an ester bond in its main chain. The dibasic acid includes phthalic acid anhydride, isophthalic acid, terephthalic acid, succinic acid, succinic anhydride, adipic acid, azelaic acid, sebacic acid, tetrahydrophthalic acid anhydride, hexahydrophthalic acid anhydride, tetrabromophthalic acid anhydride, tetrachlorophthalic acid anhydride, HET acid anhydride (chlorendic anhydride), endomethylene tetrohydrophthalic acid anhydride, maleic anhydride, fumaric acid, itaconic acid, and the like; and the dibasic acid ester includes dimethyl terephthalate, dimethyl naphthalenedicarboxylate, and the like. The dihydric alcohol includes ethylene glycol, propylene glycol, 1,3-butylene glycol, 1,6-hexanediol, diethylene glycol, dipropylene glycol, neopentyl glycol, triethylene glycol, hydrogenated bisphenol A, bisphenol dihydroxypropyl ether, 1,4-butanediol, cyclohexanedimethanol, and the like.

The polyacrylic acid resin is a resin composed of a polymer mainly of acrylic acid, methacrylic acid, and a derivative thereof. The polyacrylic acid resin includes a polymer of methyl acrylate, ethyl acrylate, methyl methacrylate, or acrylonitrile, and the polyacrylic acid resin also includes copolymer with vinyl acetate, vinyl chloride, styrene, or the like.

The polyamino acid resin refers to a polymer prepared by polycondensation of α-amino acids with a peptide bond. The polyolefin-based resin includes homopolymers of olefins such as ethylene, propylene or butene, diolefins such as butadiene, isoprene, or pentadiene, or copolymers composed of given combinations of these olefins and diolefins. Specifically, the polyolefin-based resin includes low-density polyethylenes, high-density polyethylenes, polypropylene, ethylene-propylene copolymers, polybutadienes, polyisoprenes, and the like.

The epoxy resin refers to a resin obtained by a polymerization reaction of a polyfunctional epoxy compound, with a polyamine-based curing agent, such as diethylenetriamine or diaminodiphenylmethane, or a polyphenol compound, such as bisphenol A, or a polyhydric alcohol compound. The epoxy resin includes, for example, a bisphenol A-type epoxy resin obtained from epichlorohydrin and bisphenol A; a cycloaliphatic epoxy resin obtained from epichlorohydrin and a cycloaliphatic derivative such as cyclopentadiene; a glycidylamine-type epoxy resin obtained from epichlorohydrin and hydantoin; an epoxy resin obtained from a polyepoxy compound and a polyamine compound; an epoxy resin obtained from a polyepoxy compound and a polyhydric alcohol compound; and the like.

The synthetic resins in this embodiment can be used in admixture of a given combination of two or more kinds.

The above-mentioned imparting agent not only has excellent moisture-controlling ability in which a large amount of moisture is quickly absorbed and at the same time moisture is quickly released, but also has excellent dimensional stability upon absorption of the moisture. Therefore, since the composition contains this imparting agent, a film that is less likely to generate dew condensation and useful for clothes that is less likely to cause dampness, whereby a composition containing a synthetic resin suitable for synthetic leather having moist texture and feel can be obtained.

The amount of the above-mentioned imparting agent used in this embodiment is preferably from 0.01 to 100 parts by weight, more preferably from 0.1 to 50 parts by weight, and even more preferably from 2 to 10 parts by weight, based on 100 parts by weight of the composition. When the amount of the above-mentioned imparting agent is within this range, it is preferable because an effect of adding the imparting agent is sufficiently exhibited, and there is a low risk of losing the physical properties inherently owned by the synthetic resin.

In this embodiment, micropores may be formed on the surface layer, for the purpose of improving texture of the surface of the manufactured article made of the synthetic resin. In this case, it is preferable that an appropriate bubble forming agent is formulated in the above-mentioned composition.

As a method of forming micropores on the surface layer, a generally employed method includes a wet method using a poor solvent, or a dry method by means of heating, and is not particularly limited as long as the method is capable of forming micropores on the surface layer. The main bubble forming materials that are used in the method of forming micropores are listed hereinbelow.

In the dry method by means of heating, a foaming agent is used as a bubble forming material. As the foaming agent, sodium bicarbonate, ammonium bicarbonate, ammonium carbonate, ammonium nitrite, sodium borohydride, azodicarbonamide, azobisformamide, azobisisobutyronitrile, barium azaodicarboxylate, N,N'-dinitrosopentamethylenetetramine, N,N'-dinitroso-N,N'-dimethylterephthalamide, benzenesulfonyl hydrazide, p-toluenesulfonyl hydrazide, p,p'-oxybisbenzenesulfonyl hydrazide, p-toluenesulfonyl semicarbazide, 5-phenyl-1H-tetrazole, and the like. Among them, sodium bicarbonate, azodicarbonamide, azobisformamide, and N,N'-dinitrosopentamethylenetetramine are preferable.

In the wet method using a poor solvent, the solvent in the solution used also serves as a bubble forming material. The solvent to be used includes water, fluorocarbons, chlorine-containing compounds, petroleum-based hydrocarbons, esters, ketones, ethers, alcohols, and the like.

The chlorine-containing compound includes chloroform, carbon tetrachloride, and dichlorobenzene; the petroleum-based hydrocarbon includes benzene, toluene, xylene, pyridine, hexane, and petroleum ether; the ester includes ethyl acetate and methyl acetate; the ketone includes acetone; the ether includes diethyl ether; the alcohol includes methanol, ethanol, propanol, and butanol; and the like. Among them, water, chloroform or dichlorobenzene is preferable.

In addition, a substance having deliquescence can be also used as a bubble forming material. In other words, if a substance having deliquescence is added to a composition and thereafter rinsed with water, the substance having deliquescence is eluted to water and the surface layer becomes microporous. The substance having deliquescence includes calcium chloride, sodium hydroxide, ferric chloride, potassium hydroxide, lithium hydroxide, and the like, and calcium chloride is preferable.

Usually, the bubble forming material is used within the range of preferably from 0.001 to 50 parts by weight, based on 100 parts by weight of the above-mentioned composition, without being particularly limited thereto. When the bubble forming material is 0.001 parts by weight or more, it is preferable because an effect of addition is exhibited, and when the bubble forming material is used in an amount of 50 parts by weight or less, it is preferable because resin strength is not exceedingly lowered.

The composition of this embodiment can further be formulated with a known substance generally added to a synthetic resin, specifically, an antioxidant, a stabilizer such as a thermal stabilizer or an ultraviolet absorbent, an antistatic agent, a fire retardant, a lubricant, a plasticizer, and a crystallization accelerator, a crystalline nucleating agent, an antibacterial agent, and other inorganic fillers and organic filers for the purpose of reinforcement or the like. In addition, a synthetic resin other than the above-mentioned synthetic resin exemplified as the synthetic resin used in this embodiment can be as a matter of course formulated.

The composition in this embodiment is obtained by mixing the above-mentioned imparting agent with a synthetic resin in a dissolution state or a molten state under heating conditions. In other words, in the mixing method in the dissolution state, a method comprising adding a given amount of the above-mentioned imparting agent to a synthetic resin, or a monomer or a prepolymer thereof, dissolved in a given solvent, and kneading the mixture with a rotary kneader such as a mixer, a roll-mill, a ball-mill, an attritor, or a sand grinder is generally employed.

In addition, the method of melt-mixing under heating conditions generally comprises formulating a given amount of the above-mentioned imparting agent together with each of other components; pre-mixing the mixture with a generally known mixer such as a Henschel mixer, a V blender, a tumbler mixer, or the like, and thereafter melt-kneading the resulting mixture with a single-screw kneader, or a twin-screw kneader such as an intermeshing co-rotating kneader, a non-intermeshing co-rotating kneader, an intermeshing counter-rotating kneader, or a non-intermeshing counter-rotating kneader, or melt-kneading according to a continuous melt-kneading method by means of calendar, paste coating, or the like, or according to a batch-type melt-kneading method with a roller, a Banbury or the like. The heating conditions during the melt-kneading are not particularly limited, and the heating conditions are usually within the range of from 80° to 350° C., and preferably from 100° to 250° C.

Here, the timing of addition of the above-mentioned imparting agent is not particularly limited, and the imparting agent may be added at any point of the process for preparing the composition. For example, the imparting agent may be added at the stage of a monomer or a prepolymer, which is directly subjected to polymerization.

The composition of this embodiment can be produced into various molded articles in accordance with an ordinary method of molding a synthetic resin. Preferably, there may be used as a film-like molded article such as a wrapping material, a coating material, a material for clothes, or a material for a nonwoven fabric; fibrous articles for a woven fabric, a knitted article, or the like; a part of a laminate obtained by coating or laminating the composition on a surface of paper, a nonwoven fabric or the like; or the like. The molded working article of the resin composition of this embodiment has excellent water breathability, smaller risk of generating dew condensation or the like, and also has a smaller dimensional change to change in surrounding humidity, thereby having a high dimensional stability.

The molding method of the composition of this embodiment as described above is not particularly limited, and the composition can be worked according to each purpose. The molding method includes, for example, injection molding, extrusion molding, compression molding, sheet molding, lamination molding, hollow molding, vacuum molding, transfer molding, blow molding, calendar molding, injection molding, paste coating method, powder molding and the like.

In addition, the composition of this embodiment can be suitably used as a material for synthetic leather. In the case of a synthetic leather, a layer made from a composition of this embodiment of which surface is made microporous with the above-mentioned bubble forming material or the like, is coated or laminated on a support made of a woven fabric, a knitted fabric, paper, or a nonwoven fabric, to form a natural leather-like surface layer. As the synthetic resin used in the surface layer of the synthetic leather as described above, a polyvinyl chloride, a polyamide, or a polyurethane is preferable. Furthermore, it is preferable that a finishing layer made of a modified polyamide, a polyurethane, a polyacrylic acid derivative, a polyamino acid blend, or the like is provided on the surface of the microporous layer to finish the surface in a leather-like pattern. The synthetic leather obtained in the manner as described above has excellent water breathability, and moist texture distinctively owned by leather.

Embodiment 5

Moisture-Controlled Material

The moisture-controlled material of this embodiment contains the above-mentioned imparting agent.

The porous silica used in this embodiment has pores having an average pore size of preferably from 1 to 10 nm, and more preferably from 2 to 5nm.

The porous silica used in this embodiment has a pore volume of preferably from 0.2 to 2.0 $cm^3/g$, from the viewpoint of adsorption volume.

The porous silica used in this embodiment has a specific surface area of preferably from 400 to 1500 $m^2/g$, and more preferably from 600 to 1200 $m^2/g$, from the viewpoint of adsorption volume.

The porous silica used in this embodiment has an average particle size of preferably from 50 nm to 10 μm, more preferably from 50 to 500 nm, and even more preferably from 50 to 300 nm.

Since the porous silica used in this embodiment has the above-mentioned feature, the porous silica has excellent water breathability wherein the moisture is quickly adsorbed under high humidity conditions, and the moisture is quickly desorbed under low humidity conditions.

The above-mentioned imparting agent, even when used as it is, functions as a moisture-controlled material, or those prepared by adding the above-mentioned imparting agent to an interior furnishing material, or a paint, a coating material or the like for an interior furnishing material, may be used as a moisture-controlled material. The interior furnishing material includes parts that can constitute a surface of the interior of a room, such as ceiling, inner wall or floor, including wallpaper, tiles, bricks, wooden plates, resin plates, and tatami mats; parts that are provided along a surface of the interior of a room or those that are provided for partitioning the space of the interior of a room, such as curtains, blind shades, rolling screens, carpets, post-set tiles, and partitions with a screen; parts that are set in the interior of a room, such as decorative objects or furniture, each made of ceramics, a resin or a wooden material; and the like, and wallpaper is preferable.

When the above-mentioned imparting agent is added to various materials to give a moisture-controlled material, the content of the above-mentioned imparting agent in the moisture-controlled material is preferably from 0.01 to 60% by weight, more preferably from 0.5 to 50% by weight, even more preferably from 1 to 50% by weight, and even still more preferably from 5 to 50% by weight, from the viewpoint of water breathability.

In this embodiment, the moisture-controlled material may contain, besides the above-mentioned imparting agent, a moisture-controlled composite formed by composites of other ceramics raw materials and/or fillers, and the like. The ceramics raw materials include, for example, kaolinite, alumina sludge, bentonite, sepiolite, zeolite, allophane (Kanuma soil), cristobalite rock, and the like. In addition, the filler includes, for example, talc, pyrophyllite, aluminum hydroxide, calcium carbonate, palygorskite, glass fibers, carbon fibers, wood pulp, and the like. Furthermore, the moisture-controlled material of this embodiment can be formulated with an appropriate material such as an aromatic, a stabilizer, a surfactant, a lubricant, a colorant, an ultraviolet absorbent, an anti-bacterial agent, a mildewproof agent, or a photocatalyst.

The moisture-controlled material of this embodiment may be prepared by previously preparing a slurry containing the above-mentioned imparting agent and other components, and applying the slurry to a substrate, including, for example, a nonwoven fabric or a woven fabric, a glass fiber sheet, a metal fiber-glass fiber composite sheet, paper such as fire-resistant backing or nonflammable paper, a porous sheet, a synthetic resin sheet, a gypsum plasterboard, a particle board, a ceramic panel, a siding panel, a calcium silicate board, a concrete board, a urethane foam, an inorganic undercoat material for interior of a room, or the like, and drying the coated substrate; or immersing the substrate into the slurry, thereafter drawing up the substrate, and drying the substrate. Further, the slurry containing the above-mentioned imparting agent and the other components is subjected to papermaking together with pulp or the like to incorporate the slurry into the internal of the pulp upon. papermaking. In the case of adding a resin, for example, the resin is added in the stage of a monomer or a prepolymer, and the mixture can also be directly polymerized.

Embodiment 6

Covering Material for Wound

The covering material for a wound of this embodiment contains the above-mentioned imparting agent.

The porous silica used in this embodiment has pores having an average pore size of preferably from 1 to 10 nm, and more preferably from 2 to 5 nm.

The porous silica used in this embodiment has a pore volume of preferably from 0.2 to 2.0 $cm^3/g$, from the viewpoint of the amount of the moisture supported.

The porous silica used in this embodiment has a specific surface area of preferably from 400 to 1500 $m^2/g$, and more preferably from 600 to 1200 $m^2/g$.

The porous silica used in this embodiment has an average particle size of preferably from 50 nm to 10 μm, more preferably from 50 to 500 nm, and even more preferably from 50 to 300 nm.

Since the porous silica used in this embodiment has the above-mentioned feature, the porous silica has excellent water breathability wherein the moisture is quickly adsorbed under high humidity conditions, and the moisture is quickly desorbed under low humidity conditions.

The covering material for a wound of this embodiment contains the above-mentioned imparting agent, and a film forming material. The substance that can be used as a film forming material includes a polymeric compound that is not harmful to a human body. It is preferable to use a polymeric compound published in the Japanese Pharmacopoeia of which safety has been established as a pharmaceutical material; a polymeric compound published in Japanese Standards of Cosmetic Ingredients (Sho-gen-ki) that has been acknowledged as an aromatic or cosmetic material; a polymeric compound of which safety has been acknowledged as a quasi-drug; or a polymeric compound of which safety has been confirmed as a food additive. However, any sort of polymeric compounds can be also used, as long as the polymeric compound is one of which safety has been established against a human body. As a matter of course, it is necessary to conduct a safety test sufficiently before use to determine the amount of formulation.

Preferably, as the film forming material, a polymeric compound selected from the group consisting of naturally occurring polysaccharides, polyamino acid-based compounds such as proteins, polysaccharide derivatives obtained by chemically modifying the polysaccharides, and synthetic polymeric substances.

The naturally occurring polysaccharides includes, for example, cellulose, gum arabic, tragacanth gum, guar gum, galactan, carob gum, locust bean gum, karaya gum, irismos, quinceseed, gelatin, shellac, rosin, pectin, agar, starch, glycyrrhizic acid, algae colloid, dextran, succinoglucan, pullulan, curdlan, and the like The polysaccharide derivative includes cellulose derivatives such as carboxymethyl cellulose sodium, hydroxyethyl cellulose, hydroxypropyl cellulose, methyl cellulose, ethyl cellulose, and nitrocellulose, carboxymethyl starch sodium, hydroxyethyl starch, hydroxypropyl starch, sodium alginate, propylene glycol alginate esters, ester gum, and crystalline cellulose, and the like.

The polyamino acid-based compound includes proteins, such as casein, albumin, collagen, and gelatin. The synthetic polymer substance includes polyvinyl alcohols, polyvinyl pyrrolidone, sodium polyacrylate, carboxyvinyl polymers, polyvinyl methyl ethers, polyamide resins, polyethyleneimines, and those polymer substances containing silicon, including cyclic polysiloxanes, such as dimethyl polysiloxane, methylphenyl polysiloxane, methyl hydrogenpolysiloxane, decamethyl polysiloxane, dodecamethyl polysiloxane, tetramethyl tetrahydrogenpolysiloxane; and polysiloxane resins forming a three-dimensional network structure.

These film forming materials may be used alone, or in a combination of two or more kinds. In addition, the polymeric compound that can be used as a film forming material is not limited to these polymeric compounds exemplified.

In addition, the covering material for a wound of this embodiment may contain, besides the film forming material comprising the polymeric compound mentioned above, an adhesive material which prevents the above-mentioned imparting agent from being detached from the surface of a wound. As this adhesive, those of which safety against a human body has been established is used in the same manner as the above-mentioned film forming material.

Specific examples of the adhesive material include fats and oils such as avocado oil, almond oil, olive oil, cacao oil, beef tallow, sesame oil, wheat germ oil, safflower oil, shea butter, turtle oil, camellia oil, apricot (or peach) kernel oil, castor oil, grape seed oil, macadamia nut oil, mink oil, egg yolk oil, vegetable wax, palm oil, rose hip oil (rosa canina fruit oil), and hydrogenated oil; waxes such as orange roughy oil, carnauba wax, candelilla wax, spermaceti wax, jojoba wax, montan wax, beeswax, lanoline, and lanoline derivatives; hydrocarbons such as liquid paraffins, Vaseline, paraffins, sericin, microcrystalline wax, and squalane; higher fatty acids such as lauric acid, myristic acid, palmitic acid, stearic acid, oleic acid, behenic acid, undecylenic acid, hydroxystearic acid, linoleic acid, lanoline fatty acid, and synthetic fatty acids; higher alcohols such as lauryl alcohol, cetyl alcohol, cetostearyl alcohol, stearyl alcohol, oleyl alcohol, behenyl alcohol, lanoline alcohol, hydrogenated lanoline alcohol, octyl dodecanol, and isostearyl alcohol; sterols such as cholesterol, dihydrocholesterol, and phytosterol; fatty acid esters such as linoleic acid esters, isopropyl myristate, isopropyl lanoline fatty acids, hexyl laurate, myristyl myristate, cetyl myristate, octyldodecyl myristate, decyl oleate, octyldodecyl oleate, hexyldecyl dimethyloctanoate, cetyl isooctanoate, cetyl palmitate, glycerol trimyristate, glycerol tri(caprylate/caprate), propylene glycol dioleate, glycerol triisostearate, glycerol triisooctanoate, cetyl lactate, myristyl lactate, and diisostearyl malate; the polyhydric alcohol including, for example, dihydric alcohols such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol, trihydric alcohols such as glycerol, trimethylolpropane, and 1,2,6-hexanetriol, tetrahydric alcohols such as pentaerythritol, pentahydric alcohols such as xylitol, hexahydric alcohols such as sorbitol and mannitol; polyhydric alcohol polymers such as diethylene glycol, dipropylene glycol, triethylene glycol, polypropylene glycol, tetraethylene glycol, diglycerol, polyethylene glycol, triglycerol, tetraglycerol, and polyglycerol; divalent alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-hexylmethyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenylethyl acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers such as xylyl alcohol, selachyl alcohol and batyl alcohol; sugar alcohols such as sorbitol, maltitol, maltotriose, mannitol, sucrose, erythritol, glucose, fructose, amylolytic sugar, maltose, xylitose, and amylolytic sugar-reducing alcohol; glyceride, tetrahydrofurfuryl alcohol, POE tetrahydrofurfuryl alcohol, POP butyl ether, POP-POE butyl ether, tripolyoxypropylene glycerol ether, POP glycerol ether, POP glycerol ether phosphate, POP-POE pentaerythritol ether, and the like.

Further, the adhesive material includes sodium dl-pyrrolidonecarboxylate, sodium lactate, sorbitol, sodium hyaluronate, and the like. Moreover, the polymeric compounds shown as the previously mentioned film forming material can also be used as an adhesive material. In addition, these adhesive materials can be formulated in a combination of two or more kinds. Both the film forming material and the adhesive material may be used in a combination of two or more kinds.

The wound covering material may be further formulated with a surfactant such as an anionic surfactant, a lipophilic or hydrophilic nonionic surfactant, a cationic surfactant, or an amphoteric surfactant.

The lipophilic nonionic surfactant includes, for example, sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexanoate, and diglycerol sorbitan tetra-2-ethylhexanoate; glycerol (or polyglycerol) fatty acid esters such as glycerol monocottonseed oil fatty acid esters, glycerol monoerucate, glycerol sesquioleate, glycerol monostearate, glycerol $\alpha,\alpha'$-oleate pyroglutamate, and glycerol malate monostearate; propylene glycol fatty acid esters such as propylene glycol monostearate; hydrogenated castor oil derivatives; glycerol alkyl ethers; and the like.

The hydrophilic nonionic surfactant includes, for example, POE sorbitan fatty acid esters such as POE sorbitan monooleate, POE-sorbitan monostearate, POE-sorbitan monooleate, and POE-sorbitan tetraoleate; POE sorbitol fatty acid esters such as POE-sorbitol monolaurate, POE-sorbitol monooleate, POE-sorbitol pentaoleate, and POE-sorbitol monostearate; POE glycerol fatty acid esters such as POE-glycerol monostearate, POE-glycerol monoisostearate, and POE-glycerol triisostearate; POE fatty acid esters such as POE monooleate, POE distearate, POE mono-dioleate, ethylene glycol distearate; POE alkyl ethers such as POE lauryl ether, POE oleyl ether, POE-stearyl ether, POE behenyl ether, POE 2-octyl dodecyl ether, and POE cholestanol ether; POE alkylphenyl ethers such as POE octylphenyl ether, POE nonylphenyl ether, and POE dinonylphenyl ether; POE-POP alkyl ethers such as POE-POP cetyl ether, POE-POP 2-decyl tetradecyl ether, POE-POP monobutyl ether, POE-POP hydrogenated lanoline, and POE-POP glycerol ether; POE-POP ethylenediamine condensates; POE castor oil (or hydrogenated castor oil) and derivatives, such as POE castor oil, POE hydrogenated castor oil, POE hydrogenated castor oil monoisostearate, POE hydrogenated castor oil triisostearate, POE hydrogenated castor oil monopyroglutamate monoisostearate diester, POE hydrogenated castor oil maleate; POE beeswax lanoline derivatives such as POE sorbitol beeswax; alkanolamides such as palm oil fatty acid ester diethanolamide, laurate monoethanolamide, and isopropanolamide of fatty acids; POE propylene glycol fatty acid esters, POE alkyl amines, POE fatty acid amides, sucrose fatty acid esters, POE nonylphenyl formamide condensates, alkylethoxydimethylamine oxide, trioleylphosphate, and the like.

The anionic surfactant includes, for example, fatty acid soaps such as base materials for soaps, sodium laurate, and sodium palmitate; higher alkyl sulfuric esters such as sodium lauryl sulfate and potassium(K) lauryl sulfate; salts of alkyl ether sulfuric esters such as POE lauryl sulfate triethanolamine and sodium POE lauryl sulfate; N-acyl sarcosines such as lauroyl sarcocine sodium; higher fatty acid amide sulfonates such as sodium N-myristoyl-N-methyl taurate, sodium palm oil fatty acid methyl tauride, and sodium lauryl methyl tauride; phosphate esters such as sodium POE oleyl ether phosphate and POE stearyl ether phosphate; sulfosuccinates such as sodium di-2-ethylhexyl sulfosuccinate, sodium monolauroyl monoethanolamide polyoxyethylene sulfosuccinate, and sodium lauryl polypropylene glycol sulfosuccinate; alkylbenzenesulfonates such as sodium linear dodecylbenzenesulfonate, linear dodecylbenzenesulfonate triethanolamine, and linear dodecylbenzenesulfonic acid; N-acyl glutamate such as monosodium N-lauroyl glutamate, disodium N-stearoyl glutamate, monosodium N-myristoyl-L-glutamate; sulfuric esters of higher fatty acid esters such as sulfated sodium glycerol hydrogenated palm oil fatty acid ester; sulfated oils such as Turkey red oil; POE alkyl ether carboxylates, $\alpha$-olefinsulfonates, salts of sulfonic acids of higher fatty acid esters, salts of secondary alcohol sulfuric esters, sulfuric esters of higher fatty acid alkylolamides, sodium lauroyl monoethanolamide succinate, N-palmitoyl aspartate di-triethanolamine, sodium caseinate, and the like.

The cationic surfactant includes, for example, alkyl trimethylammonium salts such as stearyl trimethylammonium chloride and lauryl trimethylammonium chloride; dialkyl dimethyl ammonium salts such as distearyl dimethylammonium chloride; alkylpyridinium salts such as poly(N,N-dimethyl-3,5-methylenepiperidinium) chloride and cetylpyridinium chloride; alkyl quaternary ammonium salts, alkyl dimethylbenzylammonium group, alkyl isoquinolinium salts, dialkyl morpholinium salts, POE alkylamines, alkylamine salts, polyamine fatty acid derivatives, amyl alcohol fatty acid ester derivatives, benzalkonium chloride, benzethonium chloride, acrylic acid-$\beta$-N—N-dimethyl-N-ethylammonioethyl acid vinyl pyrrolidone copolymers, cationic polymer derivatives, and the like.

The amphoteric surfactant includes, for example, imidazoline-based amphoteric surfactants such as 2-undecyl-N,N,N-(hydroxyethyl carboxymethyl)-2-imidazoline sodium, 2-cocoyl-2-imidazolinium hydroxide-1-carboxyethyloxy disodium salts; betaine-based surfactants such as 2-heptadecyl-N-carboxymethyl-N-hydroxyethyl imidazolinium betaine, lauryl dimethyl aminoacetate betaine, alkylbetaine, amide betaine, and sulfobetaine; and the like. Other surfactants include glycerol fatty acid esters, polyglycerol fatty acid esters, sucrose fatty acid esters, sorbitan fatty acid esters, propylene glycol fatty acid esters, lecithin, enzymatically decomposed lecithin, and the like.

The wound covering material may be further formulated with, as powder component, an inorganic powder of talc, kaolin, mica, sericite, muscovite, phlogopite, synthetic mica, lepidolite, biotite, lithia mica, vermiculite, magnesium carbonate, calcium carbonate, aluminum silicate, barium silicate, barium sulfate, magnesium sulfate, calcium silicate, aluminum silicate, barium silicate, barium sulfate, strontium silicate, metal salts of tungstate, silica, zeolite, barium sulfate, baked calcium sulfate (baked gypsum), calcium phosphate, fluorine apatite, hydroxyapatite, ceramic powder, metal soaps (zinc myristate, calcium palmitate, aluminum stearate), boron nitride, cerium oxide, magnesium metasilicoaluminate, magnesium silicoaluminate, aluminum hydroxychloride, aluminum chloride, aluminum sulfate, aluminum citrate, aluminum acetate, basic aluminum chloride, aluminum phenolsulfonate, aluminum β-naphtholdisulfonate, sodium perborate, aluminum zirconium octachloro hydrate, aluminum zirconium pentachloro hydrate, aluminum zirconium tetrachloro hydrate, aluminum zirconium trichloro hydrate, zirconium hydrate or the like; and an organic powder such as a polyamide resin powder (nylon powder), a polyethylene powder, a methyl polymethacrylate powder, a polystyrene power, a copolymer resin powder of styrene and acrylic acid, a poly(ethylene tetrafluoride) powder. polypropylene, chitin, chitosan, or a cellulose powder; the like.

In addition, the wound covering material can be formulated with an inorganic white pigment such as titanium dioxide, zinc oxide, or zirconium oxide; an inorganic red pigment such as iron oxide (red iron oxide) or iron titanate; an inorganic brown pigment such as γ-iron oxide; an inorganic yellow pigment such as yellow iron oxide or ocher; an inorganic black pigment such as black iron oxide, carbon black, or titanium oxide having a low oxidation state; an inorganic purple pigment such as mango violet or cobalt violet; an inorganic green pigment such as chromium oxide, chromium hydroxide, or cobalt titanate; an inorganic blue pigment such as ultramarine blue or Prussian blue; a pearl pigment such as titanium oxide-coated mica, bismuth oxychloride, titanium oxide-coated bismuth oxychloride, titanium oxide-coated talc, colored titanium oxide-coated mica, or dew pearl; a metal powder pigment such as an aluminum powder or a copper powder; an organic pigment such as Red 201, Red 202, Red 204, Red 205, Red 220, Red 226, Red 228, Red 405, Orange 203, Orange 204, Yellow 205, Yellow 401, or Blue 404; zirconium, barium or aluminum lake pigment, such as Red 3, Red 104, Red 106, Red 227, Red 230, Red 401, Red 505, Orange 205, Yellow 4, Yellow 5, Yellow 202, Yellow 203, Green 3 and Blue 1; or a natural pigment such as chlorophyll or β-carotene.

Further, a drug or an additive, such as a drug for preventing purulence, a disinfectant, a local anesthetic, a sedative, a dermatoplastic accelerator, an adrenocortical hormone agent, an antibiotic, a zinc oxide powder, a sulfur powder, a titanium oxide powder, talc, kaolin, mica, calcium carbonate, magnesium carbonate, a moisturizer, a lower alcohol, a perfume, a preservative, an anti-bacterial agent, an antioxidant, a dermal astriction agent, a vitamin agent, a placenta extract, elastin, collagen, an aloe extract, a peach leaf extract, water containing *Hamamelis virginiana*, water containing *Luffa cylindrica*, a chamomile extract, or a glycyrrhiza extract can be formulated in a proper amount according to its purpose.

The wound covering material of this embodiment can be obtained by properly mixing the above-mentioned imparting agent, the film forming material, and various kinds of formulation components used as occasion demands according to a known method. The method of mixing is not particularly limited, and for example, a kneader, a mixer, an impeller agitator or the like can be used.

In the wound covering material of this embodiment, it is preferable that the above imparting agent is contained in an amount of from 0.1 to 30% by weight of the wound covering material. If the content of the above-mentioned imparting agent is 0.1% by weight or more, it is preferable because an effect of adding the imparting agent is exhibited, and if the content is 30% by weight or less, it is preferable because the wound covering material would not become too thick and are less likely to be peeled away, so that damp feel of the wound is less likely to be caused.

The wound covering material of this embodiment can be prepared as a covering material for spray-type coating using an aerosol. The covering material for spray-type coating is not particularly limited, as long as the covering material can be used by spraying to the surface of a wound. In addition, besides the particles of a metal salt of polyvalent alginate, a liquefied petroleum gas, silicic acid anhydride, a polyvinyl alcohol, a polyoxyethylene sorbitan monooleate, or the like can be formulated.

In addition, the wound covering material of this embodiment can be used by preparing the covering material in the form of an emulsion, a suspension, a cream or the like depending upon its use embodiment, and applying the covering material on the wound surface using fingers or equipments.

In both of the cases, a film containing the above-mentioned imparting agent is formed to cover and protect the wound. The formed film covering the wound quickly absorbs a body fluid oozing from an opening of a wound, and dissipates moisture, so that the wound surface is quickly dried, so that curing of the wound can be accomplished. Here, the thickness of the film formed on a wound surface by the wound covering material of this embodiment is usually from 10 to 1000 μm or so.

Embodiment 7

Insulation Substrate or Coating Material for Semiconductor Device

The insulation substrate or the coating material for a semiconductor device of the present invention contains the above-mentioned imparting agent.

The insulation substrate in this embodiment refers to a part having a dent portion for housing a semiconductor element in a premolding-type semiconductor device, and a coating material refers to a part coating a semiconductor element, a substrate and an external lead terminal in a molding type semiconductor device.

The porous silica used in this embodiment has pores having an average pore size of preferably from 0.8 to 10 nm, from the viewpoint of amount of water adsorbed and adsorption sustainability.

The porous silica used in this embodiment has a pore volume of preferably from 0.2 to 2.0 cm$^3$/g, and more preferably from 0.3 to 1.5 cm$^3$/g, from the viewpoint of amount of adsorption of water to the porous silica.

The porous silica used in this embodiment has a specific surface area of preferably from 600 to 2000 m$^2$/g, more preferably from 800 to 2000 m$^2$/g, and even more preferably from 900 to 1500 m$^2$/g, from the viewpoint of amount of water adsorption.

The porous silica used in this embodiment has an average particle size of preferably from 50 nm to 50 μm, more preferably from 300 nm to 30 μm, and even more preferably from 500 nm to 10 μm.

The content of the above-mentioned imparting agent in the insulation substrate or the coating material for a semiconductor device of this embodiment is preferably from 5 to 80% by weight, and more preferably from 10 to 70% by weight from the viewpoint of improving moisture tolerance and flexural strength of the insulation substrate or the coating material.

The insulation substrate or the coating material for a semiconductor device of this embodiment contains, besides the above-mentioned imparting agent, a resin such as an epoxy resin or a phenolic resin, various additives and the like.

The additive includes, for example, 2-ethyl-4-methylimidazole, carnauba wax, a silane coupling agent, antimony trioxide, and the like.

The insulation substrate or the coating material for a semiconductor device of this embodiment can be produced by, for example, mixing the above-mentioned components.

The insulation substrate of this embodiment can be produced by, for example, injecting the above-mentioned mixture in a given mold, and thereafter thermosetting the mixture at 150° to 200° C.

The coating material in the present invention can be produced by, for example, injecting the above-mentioned mixture into a jig mounted with a semiconductor device, a substrate, an external lead terminal or the like, and thereafter thermosetting the mixture at a temperature of 180° C. or so under a pressure of 100 kgf/mm$^2$ or so.

The insulation substrate and the coating material produced in the manner as described above can be used for a premolding-type semiconductor device and a molding-type semiconductor device, respectively.

Embodiment 8

Cosmetics

The cosmetics of the present invention contain the above-mentioned imparting agent.

The cosmetics in this embodiment include, for example, make-up cosmetics such as an antiperspirant, a powder foundation, an oily foundation, an emulsion foundation, cheek blusher, white powder, eyebrow, eye shadow, eye liner, mascara, lipstick, and nail color; body cosmetics such as body powder; and skin-care cosmetics such as cream, milky lotion, lotion, and sunscreen cosmetics. When the cosmetics are an antiperspirant, the form of the antiperspirant includes aerosol, stick, roll-on or the like, among which aerosol is preferable.

The porous silica used in this embodiment has pores having an average pore size of preferably from 0.8 to 10 nm, more preferably from 0.8 to 5 nm, and even more preferably from 0.8 to 4 nm, from the viewpoint of water breathability.

The porous silica used in this embodiment has a pore volume of preferably from 0.2 to 3.0 cm$^3$/g, and more preferably from 0.5 to 3.0 cm$^3$/g, from the viewpoint of water breathability.

The porous silica used in this embodiment has a specific surface 2 area of preferably from 600 to 2000 m$^2$/g, more preferably from 800 to 2000 m$^2$/g, and even more preferably from 900 to 2000 m$^2$/g, from the viewpoint of water breathability.

The porous silica used in this embodiment has an average particle size of preferably from 50 nm to 50 μm, more preferably from 50 nm to 30 μm, even more preferably from 50 nm to 5 μm, even still more preferably from 50 nm to 3 μm, even still more preferably from 50 nm to 1 μm, and even still more preferably from 50 to 500 nm.

Since the porous silica used in this embodiment has the above-mentioned feature, the porous silica has excellent water breathability wherein the moisture is quickly adsorbed under high humidity conditions, and the moisture is quickly desorbed under low humidity conditions.

The content of the above-mentioned imparting agent in the cosmetics of this embodiment is preferably from 0.1 to 70% by weight, more preferably from 1 to 60% by weight, even more preferably from 1 to 30% by weight, even still more preferably from 1 to 20% by weight, and even still more preferably from 1 to 10% by weight, from the viewpoint of water breathability.

The cosmetics of this embodiment contain, besides the above-mentioned imparting agent, an additive, a preservative, a perfume or the like that is ordinarily used in the preparation of cosmetics. The additive includes, for example, chlorohydroxyaluminum, talc, isopropyl myristate, dimethyl ether, mica, titanium oxide, red iron oxide, yellow iron oxide, black iron oxide, methylphenyl polysiloxane, glycerol trioctanoate, squalane, Vaseline, and the like.

The cosmetics of this embodiment can be prepared, for example, by a known method in the field of art. For example, in the case of an aerosol-type antiperspirant, the cosmetics can be prepared by mixing the above-mentioned imparting agent and the additive, and filling into a pressure-withstanding vessel. In the case of a powder foundation, the cosmetics can be prepared by mixing the above-mentioned imparting agent and the additive, pulverizing the mixture and sieving the pulverized product, and subjecting the pulverized product to compression molding in a mold.

Embodiment 9

Inkjet Recording Medium

The coating composition for an inkjet recording medium (hereinafter also simply referred to as a coating composition) of the present invention contains the above-mentioned imparting agent.

The porous silica used in this embodiment has pores having an average pore size of preferably from 0.8 to 10 nm, more preferably from 0.8 to 5 nm, and even more preferably from 0.8 to 4 nm, from the viewpoint of curling-controlling property.

The porous silica used in this embodiment has a pore volume of preferably from 0.2 to 3.0 cm$^3$/g, and more preferably from 0.5 to 3.0 cm$^3$/g, from the viewpoint of curling-controlling property.

The porous silica used in this embodiment has a specific surface area of preferably from 600 to 2000 m$^2$/g, more preferably from 800 to 2000 m$^2$/g, and even more preferably from 900 to 2000 m$^2$/g, from the viewpoint of curling-controlling property.

The porous silica used in this embodiment has an average particle size of preferably from 50 nm to 50 μm, more preferably from 50 nm to 30 μm, even more preferably from 50 nm to 10 µm, even still more preferably from 50 nm to 5 µm, even still more preferably from 50 nm to 3 µm, even still more preferably from 50 nm to 1 µm, and even still more preferably from 50 to 500 nm.

Since the porous silica used in this embodiment has the above-mentioned feature, the porous silica has excellent water breathability wherein the moisture is quickly adsorbed under high humidity conditions, and the moisture is quickly desorbed under low humidity conditions.

The content of the above-mentioned imparting agent in the inkjet recording medium of this embodiment is preferably from 0.1 to 70% by weight, more preferably from 1 to 60% by weight, and even more preferably from 1 to 30% by weight, from the viewpoint of curling-controlling property.

The inkjet recording medium of this embodiment can be prepared by applying a coating composition containing the above-mentioned imparting agent to a support.

The support includes, for example, paper, polymer sheets, polymer films, cloths, and the like.

The coating composition to be applied to a support contains, besides the above-mentioned imparting agent, a film-hardening agent, a dye fixing agent, a colored dye, a colored pigment, a dispersant, a thickening agent, a pH adjustment agent, a lubricant, a fluidity fluctuating agent, an antistatic agent, a defoaming agent, a penetrant, a fluorescent brightening agent, an ultraviolet absorbent, an antioxidant, or the like. The composition can be prepared by mixing the above-mentioned imparting agent and other chemical agents.

The content of the above-mentioned imparting agent in the coating composition is preferably from 1 to 99% by weight, from the viewpoint of improving curling-controlling property, ink absorbability, light fastness, and water resistance.

The application of the coating composition to a support is not particularly limited, and the application can be carried out by employing a conventionally known coating method, for example, a spin-coating method, a roll-coating method, a blade-coating method, an air knife-coating method, a gate roll-coating method, a bar coating method, a size pressing method, a spray-coating method, a gravure coating method, a curtain coating method, a rod blade-coating method, a lip coating method, a slit dye coating method, or the like.

The coating composition of this embodiment can be prepared by, for example, mixing the above-mentioned imparting agent and other chemical agents.

Embodiment 10

Composition Containing Synthetic Fibers

The composition containing synthetic fibers of the present invention contains the above-mentioned imparting agent.

The synthetic fibers in this embodiment include, for example, fibers made of a polyester such as polyethylene terephthalate, polytrimethylene terephthalate, polybutylene terephthalate, or polylactic acid; a polyamide such as nylon 6 or nylon 66, fibers composed of acryl, polyethylene, polypropylene, polyurethane, or the like, copolymers thereof, and blends thereof. The polyester and the polyamide are preferable, from the viewpoint of their wide uses.

The porous silica used in this embodiment has pores having an average pore size of preferably from 0.8 to 10 nm, more preferably from 0.8 to 5 nm, and even more preferably from 0.8 to 4 nm, from the viewpoint of water breathability. If the porous silica has an average pore size of 0.8 nm or more, the adsorption of water vapor is less likely to be saturated in a low-humidity range, and sufficient hygroscopic property can be exhibited in a high-humidity range. On the other hand, if the porous silica has an average pore size of 10 nm or less, the relative humidity at which capillary condensation takes place would not become too high, so that sufficient hygroscopic property can be exhibited.

The porous silica used in this embodiment has a pore volume of preferably from 0.2 to 3.0 $cm^3/g$, and more preferably from 0.5 to 3.0 $cm^3/g$, from the viewpoint of water breathability.

The porous silica used in this embodiment has a specific surface area of preferably from 600 to 2000 $m^2/g$, more preferably from 800 to 2000 $m^2/g$, and even more preferably from 900 to 2000 $m^2/g$, from the viewpoint of amount of water adsorption.

The porous silica used in this embodiment has an average particle size of preferably from 50 nm to 50 µm, more preferably from 50 nm to 30 µm, even more preferably from 50 nm to 10 µm, even still more preferably from 50 nm to 5 µm, even still more preferably from 50 nm to 3 µm, even still more preferably from 50 nm to 1 µm, and even still more preferably from 50 to 500 nm.

Since the porous silica used in this embodiment has the above-mentioned feature, the porous silica has excellent water breathability wherein the moisture is quickly adsorbed under high humidity conditions, and the moisture is quickly desorbed under low humidity conditions.

The content of the above-mentioned imparting agent in the composition containing synthetic fibers of this embodiment is preferably from 0.1 to 70% by weight, more preferably from 1 to 60% by weight, even more preferably from 1 to 30% by weight, and even still more preferably from 1 to 10% by weight, from the viewpoint of water breathability.

The composition containing synthetic fibers of this embodiment can be prepared by, for example, a known method in the field of art. For example, the composition can be prepared by kneading the above-mentioned imparting agent and synthetic fibers. Also, the prepared composition can be subjected to melt-spinning or stretching, and the prepared composition is further used as warp and welt to produce a plain fabric. Thereafter, the resulting plain fabric is subjected to a treatment as scouring, intermediate setting, and an alkali reduction in accordance with the method to be prepared into a form that is suitable for each application.

The composition containing synthetic fibers prepared in the manner as described above can be used for general clothes, such as shirts, pants, jackets, suits, blouses, sweaters, blousons, inner wears, socks, and stockings; sportswears such as windbreakers; a work uniform, a uniform, gloves, and inner cups, as well as industrial, domestic or leisure materials, such as filters, car seats, sheets for walls, tents, bags (carryalls), and sports bags, and wigs, hairpieces, hats, and wallets.

EXAMPLES

The present invention will be specifically described hereinbelow by the Examples, without intending to limit the scope of the present invention thereto.

The form of pores was determined with a fully automatic X-ray diffractometer (RINT ULTIMA II, manufactured by Rigaku Denki K.K.). The average pore size, pore volume and specific surface area were calculated from the nitrogen adsorption isotherm determined according to a known BET method. The average particle size was determined with a laser diffraction particle size distribution analyzer (manufactured by HELOS & RODOS SYMPATEC). The d value was determined with a fully automatic X-ray diffractometer (RINT ULTIMA II, manufactured by Rigaku Denki K.K.). In addition, the state of the primary particles was observed with a transmission electron microscope (JEM-200CX, manufactured by JEOL). Further, the amount of chlorophyll adsorption of the porous silica was determined as follows.

Test for Amount of Chlorophyll Adsorption

One gram of a porous silica was placed in 100 mL of a 0.1% NaOH ethanol solution, and the mixture was stirred at room temperature for 5 minutes. Thereafter, the porous silica was taken out from the solution, and washed with ethanol in order to remove an alkali, and the washed porous silica was dried, to give an alkali-treated porous silica. One-hundred milligrams of the alkali-treated porous silica was added to 2 mL of a benzene solution of chlorophyll a (chlorophyll concentration: 20 mM), and the mixture was shaken at 25° C. for 30 minutes. Thereafter, the mixture was centrifuged at 7000 rpm for 20 minutes, and its supernatant was collected. The amount of chlorophyll a in the supernatant was determined using a spectrophotometer (HITACHI Spectrometer U-2000). The amount of chlorophyll a in the supernatant was subtracted from the amount of chlorophyll a before addition of the porous silica, which was defined as the amount of chlorophyll adsorption of the porous silica.

Preparation Example 1-1 of Porous Silica

Fifty grams of powder sodium silicate ($SiO_2/Na_2O=2.00$) manufactured by Nippon Chemical Industrial Co., LTD. was dispersed in 1000 mL of a 0.1 M aqueous solution of octadecyltrimethylammonium chloride [$C_{18}H_{37}N(CH_3)_3Cl$], a surfactant, and the dispersion was heated at 70° C. for 3 hours while stirring. Thereafter, while heating the mixture at 70° C. and stirring, a 2 N hydrochloric acid was added to the dispersion, to lower its pH to 8.5, and the mixture was further heated at 70° C. for 3 hours while stirring. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica A-1.

It was confirmed by X-ray diffraction that pores having a hexagonal structure were formed in the resulting porous silica A-1. In addition, the porous silica A-1 had an average pore size of 2.7 nm, as determined by a BJH method, a pore volume of 1.13 cm$^3$/g, as determined by a BJH method, an average particle size of 380 nm, and a specific surface area of 941 m$^2$/g, as determined by a BET method. In addition, 60% or more of the pores fell within the range of ±40% of the pores showing a maximum peak in the pore size distribution curve.

Preparation Example 1-2 of Porous Silica

Powder sodium silicate ($SiO_2/Na_2O=2.00$) manufactured by Nippon Chemical Industrial Co., LTD. was baked in air at 700° C. for 6 hours to give crystals of $\delta$-$Na_2Si_2O_5$. Fifty grams of the crystals obtained were dispersed in 500 mL of ion-exchanged water, and the dispersion was stirred at 25° C. for 3 hours. Thereafter, a solid content was collected by filtration to give 50 g (on a dry basis) of wet kanemite, a layered silicate. This kanemite, without being dried, was dispersed in 1000 mL of a 0.1 M aqueous solution of sodium oleylsulfate, a surfactant, and the dispersion was heated at 70° C. for 3 hours while stirring. Thereafter, a 2 N hydrochloric acid was added to the dispersion while heating at 70° C. and stirring to lower its pH to 8.5, and the mixture was further heated at 70° C. for 3 hours while stirring. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. A dried solid product was heated in nitrogen gas at 450° C. for 3 hours, and thereafter the heated solid product was baked in air at 550° C. for 6 hours to give a porous silica B-1.

It was confirmed by X-ray diffraction that pores having a hexagonal structure were formed in the resulting porous silica B-1. In addition, the porous silica B-1 had an average pore size of 2.9 nm, as determined by a BJH method, a pore volume of 1.09 cm$^3$/g, as determined by a BJH method, an average particle size of 350 nm, and a specific surface area of 932 m$^2$/g, as determined by a BET method.

Preparation Example 1-3 of Porous Silica

Two grams of polyethylene glycol, 15 g of ion-exchanged water and 60 mL of a 2 N hydrochloric acid were dispersed at 80° C. while stirring. Thereafter, 4.25 g of tetraethoxysilane (TEOS) was added to the dispersion, and the mixture was stirred at 80° C. for 12 hours. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica C-1.

It was confirmed by X-ray diffraction that pores having a hexagonal structure were formed in the resulting porous silica C-1. In addition, the porous silica C-1 had an average pore size of 2.8 nm, a pore volume of 1.02 cm$^3$/g, an average particle size of 300 nm, and a specific surface area of 928 m$^2$/g.

Preparation Example 1-4 of Porous Silica

One-hundred grams of a cetyltrimethyl hydroxide (CTMA) solution prepared by contacting a 29% by weight solution of N,N,N-trimethyl-1-hexadecylammonium chloride with a hydroxide-halide exchange resin was mixed with 100 g of an aqueous solution of tetramethylammonium (TMA) silicate (silica 10%) while stirring. Thereto was added 25 g of HiSil, a sedimentary hydrated silica containing about 6% by weight of free water and about 4.5% by weight of hydrated bound water and having a cut particle size of about 0.02 μm. The mixture obtained was reacted at 90° C. for 1 day. The resulting solid product was collected by filtration, and the residue was dried at 40° C. Next, the product was baked in nitrogen at 540° C. for 1 hour, and then in air for 6 hours to give a porous silica D-1.

It was confirmed by X-ray diffraction that pores having a hexagonal structure were formed in the resulting porous silica D-1. In addition, the porous silica D-1 had an average pore size of 3.9 nm, as determined by a BJH method, a pore volume of 1.15 cm$^3$/g, as determined by a BJH method, an average particle size of 1.1 μm, and a specific surface area of 945 m$^2$/g, as determined by a BET method. In addition, 60% or more of the pores fell within the range of ±40% of the pores showing a maximum peak in the pore size distribution curve.

Preparation Example 1-5 of Porous Silica

Two grams of sodium laurylaminopropionate, 15 g of ion-exchanged water and 60 mL of a 2 N hydrochloric acid were dispersed at 80° C. while stirring. Thereafter, 4.25 g of tetraethoxysilane (TEOS) was added to the dispersion, and the mixture was stirred at 80° C. for 12 hours. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica E-1.

It was confirmed by X-ray diffraction that pores having a hexagonal structure were formed in the resulting porous silica E-1. In addition, the porous silica E-1 had an average pore size of 3.9 nm, as determined by a BJH method, a pore volume of 1.15 cm$^3$/g, as determined by a BJH method, an average particle size of 5.1 μm, and a specific surface area of 945 m$^2$/g, as determined by a BET method.

Preparation Example 1-6 of Porous Silica

Two grams of a polyethylene fatty acid ester, 15 g of ion-exchanged water and 60 mL of a 2 N hydrochloric acid were dispersed at 80° C. while stirring. Thereafter, 4.25 g of tetraethoxysilane (TEOS) was added to the dispersion, and the mixture was stirred at 80° C. for 12 hours. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica F-1.

It was confirmed by X-ray diffraction that pores having a hexagonal structure were formed in the resulting porous silica F-1. In addition, the porous silica F-1 had an average pore size of 2.8 nm, as determined by a BJH method, a pore volume of 1.02 cm$^3$/g, as determined by a BJH method, an average particle size of 5.3 μm, and a specific surface area of 928 m$^2$/g, as determined by a BET method.

Preparation Example 1-7 of Porous Silica

Two grams of polyglycerol, 15 g of ion-exchanged water and 60 mL of a 2 N hydrochloric acid were dispersed at 80° C. while stirring. Thereafter, 4.25 g of tetraethoxysilane (TEOS) was added to the dispersion, and the mixture was stirred at 80° C. for 12 hours. A solid product was temporarily filtered and re-dispersed in 1000 mL of ion-exchanged water while stirring. The procedures of filtration and dispersion-stirring were repeated 5 times, and thereafter the residue obtained was dried at 40° C. for 24 hours. A dried solid product was heated in nitrogen gas at 450° C. for 3 hours, and thereafter the heated product was baked in air at 550° C. for 6 hours to give a porous silica G-1.

It was confirmed by X-ray diffraction that pores having a hexagonal structure were formed in the resulting porous silica G-1. In addition, the porous silica G-1 had an average pore size of 2.6 nm, as determined by a BJH method, a pore volume of 0.99 cm$^3$/g, as determined by a BJH method, an average particle size of 5.8 μm, and a specific surface area of 913 m$^2$/g, as determined by a BET method.

Preparation Example 1-8 of Porous Silica

Fifty grams of powder sodium silicate (SiO$_2$/Na$_2$O=2.00) manufactured by Nippon Chemical Industrial Co., LTD. was dispersed in 1000 mL of a 0.1 M aqueous solution of behenyltrimethylammonium chloride [C$_{22}$H$_{45}$N(CH$_3$)$_3$Cl], a surfactant, and the dispersion was heated at 70° C. for 3 hours while stirring. Thereafter, while heating the mixture at 70° C. and stirring, a 2 N hydrochloric acid was added to the dispersion to lower its pH to 8.5, and then further heated while stirring at 70° C. for 3 hours. A solid product was temporarily filtered and re-dispersed in 1000 mL of ion-exchanged water while stirring. The procedures of filtration and dispersion-stirring were repeated 5 times, and thereafter the residue obtained was dried at 40° C. for 24 hours. The dried solid product was heated in nitrogen gas at 450° C. for 3 hours, and thereafter the heated solid product was baked in air at 550° C. for 6 hours to give a porous silica H-1.

It was confirmed by X-ray diffraction that pores having a hexagonal structure were formed in the resulting porous silica H-1. In addition, the porous silica H-1 had an average pore size of 4.0 nm, as determined by a BJH method, a pore volume of 1.15 cm$^3$/g, as determined by a BJH method, an average particle size of 3.1 μm, and a specific surface area of 1041 m$^2$/g, as determined by a BET method. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 4.9 nm, and there was no peak observed with a relative intensity of greater than 50% that of this intensive peak at a diffraction angle corresponding to a d value of less than 1.0 mm. Furthermore, in the porous silica H-1, primary particles having sizes of from 200 to 500 nm were aggregated. The porous silica H-1 had an amount of chlorophyll adsorption of 23.1 mg.

Preparation Example 1-9 of Porous Silica

The amount 10.5 g of behenyltrimethylammonium chloride [C$_{22}$H$_{45}$N(CH$_3$)$_3$Cl] was dispersed in 500 mL of ion-exchanged water, and separately, 4.1 g of Aerosil (300CF-5, manufactured by AEROSIL) and 25.4 g of NaOH were dispersed in 500 mL of ion-exchanged water, and then the temperature of each dispersion was raised to 70° C. Subsequently, both dispersions were mixed while stirring at 70° C. for 3 hours. Thereafter, a 2 N hydrochloric acid was added to the dispersion to lower its pH to 8.5, and then further heated while stirring at 70° C. for 3 hours. A solid product was temporarily filtered and re-dispersed in 1000 mL of ion-exchanged water while stirring. The procedures of filtration and dispersion-stirring were repeated 5 times, and thereafter the residue obtained was dried at 40° C. for 4 days. The dried solid product was heated in nitrogen gas at 450° C. for 3 hours, and thereafter the heated solid product was baked in air at 570° C. for 6 hours to give a porous silica I-1.

It was confirmed by X-ray diffraction that pores having a hexagonal structure were formed in the resulting porous silica I-1. In addition, the porous silica I-1 had an average pore size of 4.5 nm, as determined by a BJH method, a pore volume of 1.14 cm$^3$/g, as determined by a BJH method, an average particle size of 510 nm, and a specific surface area of 1052 m$^2$/g, as determined by a BET method. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 5.0 nm, and there was no peak observed with a relative intensity of greater than 50% that of the intensive peak at a diffraction angle corresponding to a d value of less than 1.0 nm. Furthermore, in the porous silica I-1, primary particles having sizes of 50 nm or so were aggregated. The porous silica I-1 had an amount of chlorophyll adsorption of 27.8 mg.

Preparation Example 1-10 of Porous Silica

One-hundred grams of a 0.1 M aqueous solution of behenyltrimethylammonium chloride [$C_{22}H_{45}N(CH_3)_3Cl$] was mixed with 100 g of a 25% aqueous solution of tetramethylammonium (TMA) while stirring. Thereto was added 25 g of HiSil, a sedimentary hydrated silica containing about 6% by weight of free water and about 4.5% by weight of hydrated bound water and having a cut particle size of about 0.02 μm. The mixture obtained was reacted in a stationary autoclave at 150° C. for 24 hours. The resulting solid product was collected by filtration, and the residue was dried at 40° C. for 24 hours. Next, the product was baked in nitrogen at 450° C. for 3 hours, and then in air for at 550° C. for 6 hours to give a porous silica J-1.

It was confirmed by X-ray diffraction that pores having a hexagonal structure were formed in the resulting porous silica J-1. In addition, the porous silica J-1 had an average pore size of 4.1 nm, as determined by a BJH method, a pore volume of 1.01 cm$^3$/g, as determined by a BJH method, an average particle size of 4.9 μm, and a specific surface area of 876 m$^2$/g. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 5.1 nm, and there was no peak observed with a relative intensity of greater than 50% that of the intensive peak at a diffraction angle corresponding to a d value of less than 1.0 nm. Further, in the porous silica J-1, primary particles having sizes of from 200 to 500 nm were aggregated. The porous silica J-1 had an amount of chlorophyll adsorption of 7.5 mg.

Preparation Example 1-11 of Porous Silica

One gram of a polyglycerol fatty acid ester (average degree of polymerization of the polyglycerol: 3 or more, a polyglycerol fatty acid ester prepared by esterifying a condensate prepared by esterifying two molecules of fatty acids each having 18 carbon atoms, with a polyglycerol, manufactured by Taiyo Kagaku Co., Ltd.) as an emulsifying agent was added to 20 g of each of the porous silicas A-1, H-1, I-1 and J-1 obtained in Preparation Examples 1-1 and 1-8 to 1-10 while mixing, to give 21 g of each of porous silicas K-1, L-1, M-1 and N-1 containing an emulsifying agent.

Preparation Example 1-12 of Porous Silica

The amount 0.7 g of a polyglycerol fatty acid ester (average degree of polymerization of the polyglycerol: 3 or more, a polyglycerol fatty acid ester prepared by esterifying a condensate prepared by esterifying two molecules of fatty acids each having 18 carbon atoms, with a polyglycerol, manufactured by Taiyo Kagaku Co., Ltd.) as an emulsifying agent and 0.3 g of an enzymatically decomposed lecithin (manufactured by Taiyo Kagaku Co., Ltd., SUNLECITHIN A-1) were added to 20 g of each of the porous silicas A-1, H-1, I-1 and J-1 obtained in Preparation Examples 1-1 and 1-8 to 1-10 while mixing, to give 21 g of each of porous silicas O-1, P-1, Q-1 and R-1 containing an emulsifying agent.

Preparation Example 2-1 of Porous Silica

Fifty grams of powder sodium silicate (SiO$_2$/Na$_2$O=2.00) manufactured by Nippon Chemical Industrial Co., LTD. was dispersed in 1000 mL of a 0.1 M aqueous solution of octadecyltrimethylammonium chloride [$C_{18}H_{37}N(CH_3)_3Cl$], a surfactant, and the dispersion was heated at 70° C. for 3 hours while stirring. Thereafter, while heating the mixture at 70° C. and stirring, a 2 N hydrochloric acid was added to the dispersion to lower its pH to 8.5, and the mixture was further heated at 70° C. for 3 hours while stirring. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica A-2.

It was confirmed by X-ray diffraction that pores having a hexagonal structure were formed in the resulting porous silica A-2. In addition, the porous silica A-2 had an average pore size of 2.7 nm, as determined by a BJH method, a pore volume of 1.05 cm$^3$/g, as determined by a BJH method, an average particle size of 380 nm, and a specific surface area of 941 m$^2$/g, as determined by a BET method. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 3.7 nm, and there was no peak observed with a relative intensity of greater than 50% that of the intensive peak at a diffraction angle corresponding to a d value of less than 1.0 nm.

Preparation Example 2-2 of Porous Silica

Powder sodium silicate (SiO$_2$/Na$_2$O=2.00) manufactured by Nippon Chemical Industrial Co., LTD. was baked in air at 700° C. for 6 hours to give crystals of δ-Na$_2$Si$_2$O$_5$. Fifty grams of the crystals obtained were dispersed in 500 mL of ion-exchanged water, and the dispersion was stirred at 25° C. for 3 hours. Thereafter, a solid content was collected by filtration to give 50 g (on a dry basis) of wet kanemite, a layered silicate. This kanemite, without being dried, was dispersed in 1000 mL of a 0.1 M aqueous solution of sodium oleylsulfate, a surfactant, and the dispersion was heated at 70° C. for 3 hours while stirring. Thereafter, a 2 N hydrochloric acid was added to the dispersion while heating at 70° C. and stirring to lower its pH to 8.5, and the mixture was further heated at 70° C. for 3 hours while stirring. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. A dried solid product was heated in nitrogen gas at 450° C. for 3 hours, and thereafter the heated solid product was baked in air at 550° C. for 6 hours to give a porous silica B-2.

It was confirmed by X-ray diffraction that pores having a hexagonal structure were formed in the resulting porous silica B-2. In addition, the porous silica B-2 had an average pore size of 2.9 nm, as determined by a BJH method, a pore volume of 1.07 cm$^3$/g, as determined by a BJH method, an average particle size of 350 nm, and a specific surface area of 932 m$^2$/g, as determined by a BET method. Moreover, by X-ray diffraction, a single intensive peak was confirmed at a diffraction angle corresponding to a d value of 3.8 nm, and there was no peak observed with a relative intensity of greater than 50% of that of the intensive peak at a diffraction angle corresponding to a d value of less than 1.0 nm.

Preparation Example 2-3 of Porous Silica

Two grams of polyethylene glycol, 15 g of ion-exchanged water and 60 mL of a 2 N hydrochloric acid were dispersed at 80° C. while stirring. Thereafter, 4.25 g of tetraethoxysilane (TEOS) was added to the dispersion, and the mixture was stirred at 80° C. for 12 hours. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica C-2.

It was confirmed by X-ray diffraction that pores having a hexagonal structure were formed in the resulting porous silica C-2. In addition, the porous silica C-2 had an average pore size of 2.8 nm, as determined by a BJH method, a pore volume of 1.03 cm$^3$/g, as determined by a BJH method, an average particle size of 300 nm, and a specific surface area of 928 m$^2$/g, as determined by a BET method. Moreover, by X-ray diffraction, a single intensive peak was confirmed at a diffraction angle corresponding to a d value of 3.6 nm, and there was no peak observed with a relative intensity of greater than 50% of that of the intensive peak at a diffraction angle corresponding to a d value of less than 1.0 nm.

Preparation Example 2-4 of Porous Silica

One-hundred grams of a cetyltrimethyl hydroxide (CTMA) solution prepared by contacting a 29% by weight solution of N,N,N-trimethyl-1-hexadecylammonium chloride with a hydroxide-halide exchange resin was mixed with 100 g of an aqueous solution of tetramethylammonium (TMA) silicate (silica 10%) while stirring. Thereto was added 25 g of HiSil, a sedimentary hydrated silica containing about 6% by weight of free water and about 4.5% by weight of hydrated bound water and having a cut particle size of about 0.02 μm. The mixture obtained was reacted at 90° C. for 1 day. The resulting solid product was collected by filtration, and the residue was dried at 40° C. Next, the product was baked in nitrogen at 540° C. for 1 hour, and then in air for 6 hours to give a porous silica D-2.

It was confirmed by X-ray diffraction that pores having a hexagonal structure were formed in the resulting porous silica D-2. In addition, the porous silica D-2 had an average pore size of 3.9 nm, as determined by a BJH method, a pore volume of 1.05 cm$^3$/g, as determined by a BJH method, an average particle size of 1.1 μm, and a specific surface area of 945 m$^2$/g, as determined by a BET method. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 4.9 nm, and there was no peak observed with a relative intensity of greater than 50% that of the intensive peak at a diffraction angle corresponding to a d value of less than 1.0 nm.

Preparation Example 2-5 of Porous Silica

Two grams of sodium laurylaminopropionate, 15 g of ion-exchanged water and 60 mL of a 2 N hydrochloric acid were dispersed at 80° C. while stirring. Thereafter, 4.25 g of tetraethoxysilane (TEOS) was added to the dispersion, and the mixture was stirred at 80° C. for 12 hours. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica E-2.

It was confirmed by X-ray diffraction that pores having a hexagonal structure were formed in the resulting porous silica E-2. In addition, the porous silica E-2 had an average pore size of 3.9 nm, as determined by a BJH method, a pore volume of 1.07 cm$^3$/g, as determined by a BJH method, an average particle size of 5.1 μm, and a specific surface area of 945 m$^2$/g, as determined by a BET method. Moreover, by X-ray diffraction, a single intensive peak was confirmed at a diffraction angle corresponding to a d value of 5.0 nm, and there was no peak observed with a relative intensity of greater than 50% that of the intensive peak at a diffraction angle corresponding to a d value of less than 1.0 nm.

Preparation Example 2-6 of Porous Silica

The same procedures as in Preparation Example 1-8 were carried out to give a porous silica F-2. The resulting porous silica F-2 has the same physical properties as those of the porous silica H-1.

Preparation Example 2-7 of Porous Silica

The same procedures as in Preparation Example 1-9 were carried out to give a porous silica G-2. The resulting porous silica G-2 has the same physical properties as those of the porous silica I-1.

Preparation Example 2-8 of Porous Silica

The same procedures as in Preparation Example 1-10 were carried out to give a porous silica H-2. The resulting porous silica H-2 has the same physical properties as those of the porous silica J-1.

Preparation Example 2-9 of Porous Silica

One gram of a polyglycerol fatty acid ester (average degree of polymerization of the polyglycerol: 3 or more, a polyglycerol fatty acid ester prepared by esterifying a condensate prepared by esterifying two molecules of fatty acids each having 18 carbon atoms, with a polyglycerol, manufactured by Taiyo Kagaku Co., Ltd.) as an emulsifying agent was added to 20 g of each of the porous silicas A-2, F-2, G-2 and H-2 obtained in Preparation Examples 2-1 and 2-6 to 2-8 while mixing, to give 21 g of each of porous silicas I-2, J-2, K-2 and L-2 containing an emulsifying agent.

Preparation Example 2-10 of Porous Silica

The amount 0.7 g of a polyglycerol fatty acid ester (average degree of polymerization of the polyglycerol: 3 or more, a polyglycerol fatty acid ester prepared by esterifying a condensate prepared by esterifying two molecules of fatty acids each having 18 carbon atoms, with a polyglycerol, manufactured by Taiyo Kagaku Co., Ltd.) as an emulsifying agent and 0.3 g of an enzymatically decomposed lecithin (manufactured by Taiyo Kagaku Co., Ltd., SUNLECITHIN A-1) were added to 20 g of each of the porous silicas A-2, F-2, G-2 and H-2 obtained in Preparation Examples 2-1 and 2-6 to 2-8 while mixing, to give 21 g of each of porous silicas M-2, N-2, O-2 and P-2 containing an emulsifying agent.

Preparation Example 3-1 of Porous Silica

The same procedures as in Preparation Example 1-8 were carried out to give a porous silica A-3. The resulting porous silica A-3 has the same physical properties as those of the porous silica H-1.

Preparation Example 3-2 of Porous Silica

The same procedures as in Preparation Example 1-9 were carried out to give a porous silica B-3. The resulting porous silica B-3 has the same physical properties as those of the porous silica I-1.

Preparation Example 3-3 of Porous Silica

Fifty grams of powder sodium silicate ($SiO_2/Na_2O=2.00$) manufactured by Nippon Chemical Industrial Co., LTD. was dispersed in 1000 mL of a 0.1 M aqueous solution of cetyltrimethylammonium chloride [$C_{16}H_{33}N(CH_3)_3Cl$], a surfactant, and the dispersion was heated at 70° C. for 3 hours while stirring. Thereafter, while heating the mixture at 70° C. and stirring, a 2 N hydrochloric acid was added to the dispersion to lower its pH to 8.5, and the mixture was further heated at 70° C. for 3 hours while stirring. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica C-3.

It was confirmed by X-ray diffraction that pores having a hexagonal structure were formed in the resulting porous silica C-3. In addition, the porous silica C-3 had an average pore size of 2.7 nm, as determined by a BJH method, a pore volume of 0.94 cm$^3$/g, as determined by a BJH method, an average particle size of 2.9 µm, and a specific surface area of 941 m$^2$/g, as determined by a BET method. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 3.7 nm, and there was no peak observed with a relative intensity of greater than 50% that of the intensive peak at a diffraction angle corresponding to a d value of less than 1.0 nm. Furthermore, in the porous silica C-3, primary particles having sizes of from 200 to 500 nm were aggregated. The porous silica C-3 had an amount of chlorophyll adsorption of 20.8 mg.

Preparation Example 3-4 of Porous Silica

Fifty grams of powder sodium silicate ($SiO_2/Na_2O=2.00$) manufactured by Nippon Chemical Industrial Co., LTD. was dispersed in 1000 mL of a 0.1 M aqueous solution of n-decyltrimethylammonium chloride [$C_{10}H_{21}N(CH_3)_3Cl$], a surfactant, and the dispersion was heated at 70° C. for 3 hours while stirring. Thereafter, while heating the mixture at 70° C. and stirring, a 2 N hydrochloric acid was added to the dispersion to lower its pH to 8.5, and the mixture was further heated at 70° C. for 3 hours while stirring. A solid product was temporarily filtered and re-dispersed in 1000 mL of ion-exchanged water while stirring. The procedures of filtration and dispersion-stirring were repeated 5 times, and thereafter the residue was dried at 40° C. for 24 hours. The dried solid product was heated in nitrogen gas at 450° C. for 3 hours, and thereafter the heated solid product was baked in air at 550° C. for 6 hours to give a porous silica D-3.

It was confirmed by transmission electron microscopy that pores having a hexagonal structure were formed in the resulting porous silica D-3. In addition, the porous silica D-3 had an average pore size of 1.7 nm, as determined by a BJH method, a pore volume of 0.50 cm$^3$/g, as determined by a BJH method, an average particle size of 2.8 µm, and a specific surface area of 943 m$^2$/g, as determined by a BET method. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 3.2 nm, and there was no peak observed with a relative intensity of greater than 50% that of the intensive peak at a diffraction angle corresponding to a d value of less than 1.0 nm. Furthermore, in the porous silica D-3, primary particles having sizes of from 200 to 500 nm were aggregated.

Preparation Example 3-5 of Porous Silica

One-hundred grams of a cetyltrimethyl hydroxide (CTMA) solution prepared by contacting a 29% by weight solution of N,N,N-trimethyl-1-hexadecylammonium chloride with a hydroxide-halide exchange resin was mixed with 100 g of an aqueous solution of tetramethylammonium (TMA) silicate (silica 10%) while stirring. Thereto was added 25 g of HiSil, a sedimentary hydrated silica containing about 6% by weight of free water and about 4.5% by weight of hydrated bound water and having a cut particle size of about 0.02 µm. The mixture obtained was reacted at 90° C. for 1 day. The resulting solid product was collected by filtration, and the residue was dried at 40° C. Next, the product was baked in nitrogen at 540° C. for 1 hour, and then in air for 6 hours to give a porous silica E-3.

It was confirmed by X-ray diffraction that pores having a hexagonal structure were formed in the resulting porous silica E-3. In addition, the porous silica E-3 had an average pore size of 2.7 nm, as determined by a BJH method, a pore volume of 0.93 cm$^3$/g, as determined by a BJH method, an average particle size of 3.9 µm, and a specific surface area of 881 m$^2$/g, as determined by a BET method. In addition, 60% or more of the pores fell within the range of ±40% of the pores showing a maximum peak in the pore size distribution curve. Moreover, by X-ray diffraction, a single intensive peak was confirmed at a diffraction angle corresponding to a d value of 3.8 nm, and there was no peak observed with a relative intensity of greater than 50% that of the intensive peak at a diffraction angle corresponding to a d value of less than 1.0 mm. Furthermore, in the porous silica E-3, primary particles having sizes of from 200 to 500 nm were aggregated. The porous silica E-3 had an amount of chlorophyll adsorption of 6.1 mg.

Preparation Example 3-6 of Porous Silica

The same procedures as in Preparation Example 1-10 were carried out to give a porous silica F-3. The resulting porous silica F-3 has the same physical properties as those of the porous silica J-1.

Preparation Example 3-7 of Porous Silica

A solution prepared by dissolving 1 g of a polyglycerol fatty acid ester (average degree of polymerization of the polyglycerol: 3 or more, a polyglycerol fatty acid ester prepared by esterifying a condensate prepared by esterifying two molecules of fatty acids each having 18 carbon atoms, with a polyglycerol, manufactured by Taiyo Kagaku Co., Ltd.) as an emulsifying agent in 10 g of ethanol was added to 20 g of each of the porous silicas A-3, B-3, C-3, D-3, E-3 and F-3 obtained in Preparation Examples 3-1 to 3-6 while mixing. Subsequently, the solvent (ethanol) was removed by concentration with a rotary evaporator, to give 21 g of each of porous silicas G-3, H-3, I-3, J-3, K-3 and L-3 containing an emulsifying agent.

Preparation Example 3-8 of Porous Silica

One gram of a polyglycerol fatty acid ester (average degree of polymerization of the polyglycerol: 3 or more, a polyglycerol fatty acid ester prepared by esterifying a condensate prepared by esterifying two molecules of fatty acids each having 18 carbon atoms, with a polyglycerol, manufactured by Taiyo Kagaku Co., Ltd.) as an emulsifying agent was added to 20 g of each of the porous silicas A-3 and B-3 obtained in Preparation Examples 3-1 and 3-2 while mixing, to give 21 g of each of porous silicas M-3 and N-3 containing an emulsifying agent.

Preparation Example 3-9 of Porous Silica

The amount 0.7 g of a polyglycerol fatty acid ester (average degree of polymerization of the polyglycerol: 3 or more, a polyglycerol fatty acid ester prepared by esterifying a condensate prepared by esterifying two molecules of fatty acids each having 18 carbon atoms, with a polyglycerol, manufactured by Taiyo Kagaku Co., Ltd.) as an emulsifying agent and 0.3 g of an enzymatically decomposed lecithin (manufactured by Taiyo Kagaku Co., Ltd., SUNLECITHIN A-1) were added to 20 g of each of the porous silicas A-3 and B-3 obtained in Preparation Examples 3-1 and 3-2 while mixing, to give 21 g of each of porous silicas O-3 and P-3 containing an emulsifying agent.

Preparation Example 3-10 of Porous Silica

The same procedures as in Preparation Example 3-8 were carried out except that a sucrose fatty acid ester (bound fatty acid 70%, a monoester of a fatty acid having 18 carbon atoms 20%, di-, tri-, poly-esters of a fatty acid having 18 carbon atoms 80%, HLB: 3, manufactured by Mitsubishi-Kagaku Foods Corporation) was used in place of the polyglycerol fatty acid ester, to give 21 g of each of porous silicas Q-3 and R-3 containing an emulsifying agent.

Example 1-1

Air-Permeable Sheet

Five percent by weight of the porous silica A-1 obtained in Preparation Example 1-1 mentioned above and 5 parts by weight of kaolin ($SiO_2$: 52% by weight, $Al_2O_3$: 42% by weight, $TiO_2$: 2% by weight, and others: 4% by weight) as a silicon dioxide-based clay mineral were added to 100 parts by weight of a composition composed of 45% by weight of a linear, low-density polyethylene and 55% by weight of calcium carbonate surface-treated with stearic acid, to prepare a polyethylene resin composition (polyolefin resin composition). This polyethylene resin composition was melted and formed into a film, and the film was and then stretched, to give an air-permeable sheet made of a polyethylene resin, having innumerable fine continuous pores.

Example 1-2

Absorbent Sheet

An absorbent sheet was produced using the porous silica A-1 obtained in Preparation Example 1-1 mentioned above. A nonwoven fabric made of pulp fiber, having a basis weight of 45 $g/m^2$ as an air-permeable substrate was subjected to immersion coating with a coating liquid prepared by mixing 85 g of the porous silica A-1 with 15 g of a binder composed of an emulsion of a styrene-acrylic copolymer resin while stirring, so as to contain the coating liquid in an amount of 30 $g/m^2$ on a dry basis, and the coated substrate was then dried to give an absorbent sheet.

Example 1-3

Liquid-Permeable Sheet

A liquid-permeable sheet was produced using the porous silica A-1 obtained in Preparation Example 1-1 mentioned above. A nonwoven fabric made of polyester-fiber, having a basis weight of 45 $g/m^2$ as an air-permeable substrate was subjected to immersion coating with a coating liquid prepared by mixing 85 g of the porous silica A-1 with 15 g of a binder composed of an emulsion of a styrene-acrylic copolymer resin while stirring, so as to contain the coating liquid in an amount of 30 $g/m^2$ on a dry basis, and the coated substrate was then dried to give an absorbent[sic] sheet.

Example 1-4

Sheet for Food Wrapping

The sheets obtained in Examples 1-1 to 1-3 mentioned above were laminated into a single sheet, to give a sheet for food wrapping.

Example 1-5

Wrapping Material for Food

A sheet for food wrapping obtained in Preparation Example 1-4 was worked into the form of a sac, to give a wrapping material for food of the present invention. One-hundred grams of freshly fried potatoes were placed into this sac, the open end of which was tightened, and the sac was heated in a microwave oven for 3 minutes. As a result, no dew condensation or no oil adhesion was found on the inner surface of the sac. Therefore, the palatability of the fried potatoes was crispy. Also, the heating test was carried out in the same manner using frozen shao-mai as the contents in the sac. As a result, the shao-mai was steamed without stickiness on its surface.

Example 1-6

Wrapping Material for Food

In Examples 1-1 to 1-4, the porous silicas H-1, I-1, J-1, L-1, M-1, N-1, P-1, Q-1 or R-1, or silicic acid anhydride (average particle size: 30 μm, average pore size: 6.5 nm, specific surface area: 450 $m^2$/g, amount of chlorophyll adsorption: 0.1 mg) was used in place of the porous silica A-1, to give an air-permeable sheet, an absorbent sheet and a liquid-permeable sheet, and each was formed into a sheet for food wrapping. A wrapping material for food was produced in the same manner as in Example 1-5, and a heating test was carried out in the same manner as above using shao-mai as the contents. The surface of the shao-mai was evaluated for extent of stickiness in 10 ranks of scores 10 to 1 (beginning from the least sticky), and the average of the scores of fifty pieces was determined. The results are shown in Table 1.

[Table 1]

TABLE 1

|  | Extent of Stickiness |
|---|---|
| Porous Silica H-1 | 7.4 |
| Porous Silica I-1 | 8.7 |
| Porous Silica J-1 | 5.2 |
| Porous Silica L-1 | 7.9 |
| Porous Silica M-1 | 9.3 |
| Porous Silica N-1 | 5.3 |
| Porous Silica P-1 | 8.3 |
| Porous Silica Q-1 | 9.5 |
| Porous Silica R-1 | 5.6 |
| Silicic Acid Anhydride | 1.2 |

Test Example 2-1

As the evaluation of the properties as the filtration aids of the porous silicas obtained in Preparation Examples mentioned above, protein adsorbability and other components by filtration in a commercially available beer were evaluated. The properties of the filtration aids of the present invention were compared with those of commercially available silica gel and activated charcoal in accordance with the following methods.

(1) Pretreatment of Commercially Available Beer and Filtration Aid

The filtration aid of the present invention, a commercially available activated charcoal (trade name: F-SH50; manufactured by FUJISAWA KASEI CO., LTD.), and a commercially available silica gel (CARPLEX BS-304; manufactured by Shionogi & Co., Ltd.) were heated at 120° C. for 1 hour to activate the mixture. The commercially available beer was degassed at room temperature for 1 hour, and 50 g of the activated filtration aid was added to 1 liter of the mixture, while stirring the mixture for 1 hour. The mixture was filtrated with a filter.

(2) Protein Adsorbability According to SASPL (Saturated Ammonium Sulfate Precipitation Limit) Value A 50% saturated ammonium sulfate was added dropwise to 50 mL of the filtrated commercially available beer at room temperature while stirring, and turbidity was determined at 660 nm. The dropping amount of ammonium sulfate at a point where the turbidity dramatically increases was defined as an SASPL value. It is shown that the larger the SASPL value, the smaller the causative protein for turbidity, i.e. the higher the ability of removing adsorption of the filtration aid to this component.

(3) Comparison of Foamability

Twenty milliliters of a commercially available beer that was filtered was stirred at room temperature for 1 hour, and a foam layer formed on a beer liquid surface was measured with a ruler. It is shown that the thicker the foam layer, the larger the amount of the foamable protein, i.e. the lower the ability of removing a filtration aid adsorbed to this component.

(4) Comparison of Tastiness

Thirty-five milliliters of a commercially available beer that was filtered was evaluated for tastiness with a taste sensor (trade name: taste sensing system SA402B; manufactured by Intelligent Sensor Technology, Inc. (INSENT)). It is shown that the higher the tastiness, the larger the amount of the bitterness component derived from *Humulus lupulus*, i.e. the lower the ability of removing a filtration aid adsorbed to this component.

[Table 2]

TABLE 2

| Filtration Aid | SASPL Value | Foamability (mm) | Tastiness (Bitterness (%)) |
|---|---|---|---|
| No Addition | 11-14 | 10.0 | 100 |
| Porous Silica A-1 | 30-34 | 9.0 | 72 |
| Porous Silica B-1 | 25-28 | 8.0 | 70 |
| Commercial Available Activated Charcoal | 18-20 | 5.0 | 69 |
| Commercial Available Silica Gel | 15-17 | 7.0 | 63 |

It could be seen from the above results that the porous silica of the present invention has excellent properties as a filtration aid.

Test Example 2-2

A test was conducted in the same manner as in Test Example 2-1 using the porous silicas H-1, I-1, J-1, L-1, M-1, N-1, P-1, Q-1 or R-1. The results are shown in Table 3.

[Table 3]

TABLE 3

| Filter Aid | SASPL Value | Foamability (mm) | Tastiness (Bitterness (%)) |
|---|---|---|---|
| Porous Silica H-1 | 35-38 | 9.1 | 75 |
| Porous Silica I-1 | 50-52 | 9.7 | 77 |
| Porous Silica J-1 | 26-28 | 7.8 | 70 |
| Porous Silica L-1 | 38-40 | 9.1 | 74 |
| Porous Silica M-1 | 54-56 | 9.7 | 76 |
| Porous Silica N-1 | 28-30 | 7.9 | 69 |
| Porous Silica P-1 | 40-42 | 9.2 | 74 |
| Porous Silica Q-1 | 56-58 | 9.7 | 76 |
| Porous Silica R-1 | 29-31 | 8.1 | 68 |

Example 3-1

Fifty grams of the porous silica A-1 and 50 g of kaolin ($SiO_2$: 52% by weight, $Al_2O_3$: 42% by weight, $TiO_2$: 2% by weight, and others: 4% by weight) as a silicon dioxide-based clay mineral were added to 1 kg of a composition composed of 45% by weight of a linear, low-density polyethylene and 55% by weight of calcium carbonate surface-treated with stearic acid, to give a polyethylene resin composition. This polyethylene resin composition was melted and formed into a film, and the film was then stretched, to produce a film made of polyethylene resin, having innumerable fine continuous pores.

Example 3-2

A sanitary napkin having a constitution as shown in FIG. 1 was produced in which the above film made of polyethylene resin was used as an air-permeable back sheet, a mesh film made of polyolefin resin was used as a liquid-permeable top sheet, and a pulp was used as an absorbent component.

Example 3-3

The same procedures as in Example 3-2 were carried out except that the amount of the porous silica A-1 was changed to 100 g, to produce a sanitary napkin.

Comparative Example 3-1

The same procedures as in Example 3-1 were carried out except that 50 g of a silica (CARPLEX, manufactured by Shionogi & Co., Ltd.) was used in place of the porous silica A-1, to produce a film made of a polyethylene resin. A sanitary napkin was produced in the same manner as in Example 3-2.

Comparative Example 3-2

The same procedures as in Example 3-1 were carried out except that 50 g of an activated charcoal was used in place of the porous silica A-1, to prepare a film made of polyethylene resin. A sanitary napkin was produced in the same manner as in Example 3-2.

Test Example 3-1

Female individuals having their menstrual periods were asked to actually put on the napkins to compare feel of use. Awareness survey was previously conducted, and 25 female individuals who were sensitive to odor during the menstrual periods were selected as monitors. Each monitor was asked to use the sanitary napkins obtained in Examples 3-2 and 3-3 and Comparative Examples 3-1 and 3-2, 4 pieces each. Of the 4 pieces of sanitary napkins, 2 pieces were used on days with larger menstrual blood losses (first to third days), and the remaining 2 pieces were used on days with smaller menstrual blood loss (fourth or subsequent days). Each sanitary napkin was put on for 2 or more hours. Thereafter, in the following situations, the individuals were asked to evaluate on how they felt on odor and damp feel in accordance with the following criteria. Here, the test was conducted without informing the materials of the napkins used and the like.

<Days with Larger Menstrual Blood Losses>
(a) Odor while putting on the napkin after one or more hours passed from putting on the napkin
(b) Odor when taking off the napkin <Days with Smaller Menstrual Blood Losses>
(c) Odor while putting on the napkin after one or more hours passed from putting on the napkin
(d) Odor when taking off the napkin Evaluation Criteria (Odor)

| Score 1 | no odor being generated |
| Score 2 | slight odor being generated but not irritable |
| Score 3 | somewhat unpleasant odor being generated |
| Score 4 | unpleasant odor being generated |

Evaluation Criteria (Damp Feel)

| Score 1 | no damp feel being generated |
| Score 2 | slight damp feel being generated but not irritable |
| Score 3 | some unpleasant damp feel being generated |
| Score 4 | unpleasant damp feel being generated |

[Table 4]

TABLE 4

| Item | Evaluation Time | | Ex. 3-2 | Ex. 3-3 | Comp. Ex. 3-1 | Comp. Ex. 3-2 |
|---|---|---|---|---|---|---|
| Odor | Days with Larger Losses | (a) While Putting on | 1.6 | 1.5 | 3.1 | 2.8 |
| | | (b) When Taking off | 2.0 | 1.8 | 3.5 | 3.2 |
| | Days with Smaller Losses | (c) While Putting on | 1.4 | 1.4 | 3.6 | 3.2 |
| | | (d) When Taking off | 1.6 | 1.5 | 3.8 | 3.5 |
| Damp Feel | Days with Larger Losses | (a) While Putting on | 1.8 | 1.6 | 3.0 | 2.9 |
| | | (b) When Taking off | 2.0 | 1.8 | 3.5 | 3.3 |
| | Days with Smaller Losses | (c) While Putting on | 1.4 | 1.3 | 3.5 | 3.5 |
| | | (d) When Taking off | 1.5 | 1.4 | 3.7 | 3.8 |

As is clear from the results shown in Table 4, the sanitary napkins of Examples 3-2 and 3-3 (products of the present invention) have a high odor-controlling effect, in which the odor was controlled to a level that no odor is generated or the odor is not irritable, and the damp feel was lowered to a level that damp feel is not irritable, as compared to the sanitary napkins of the comparative examples.

Test Example 3-2

Sanitary napkins were produced in the same manner as in Example 3-3, except that the porous silica H-1, I-1, J-1, L-1, M-1, N-1, P-1, Q-1 or R-1, and a test was conducted in the same manner as in Test Example 3-1. The results are shown in Table 5.

[Table 5]

TABLE 5

| Item | Evaluation Time | | Porous Silica | | | | | | | | |
|---|---|---|---|---|---|---|---|---|---|---|---|
| | | | H-1 | I-1 | J-1 | L-1 | M-1 | N-1 | P-1 | Q-1 | R-1 |
| Odor | Days with Larger Losses | (a) While Putting on | 1.4 | 1.1 | 2.5 | 1.3 | 1.1 | 2.3 | 1.3 | 1.0 | 2.2 |
| | | (b) When Taking off | 1.8 | 1.2 | 2.8 | 1.7 | 1.1 | 2.5 | 1.6 | 1.0 | 2.3 |
| | Days with Smaller Losses | (c) While Putting on | 1.3 | 1.2 | 2.3 | 1.3 | 1.2 | 2.2 | 1.3 | 1.0 | 2.1 |
| | | (d) When Taking off | 1.4 | 1.2 | 2.2 | 1.3 | 1.2 | 2.1 | 1.3 | 1.0 | 2.0 |
| Damp Feel | Days with Larger Losses | (a) While Putting on | 1.5 | 1.1 | 2.6 | 1.4 | 1.1 | 2.5 | 1.3 | 1.0 | 2.3 |
| | | (b) When | 1.8 | 1.2 | 2.8 | 1.6 | 1.1 | 2.7 | 1.5 | 1.0 | 2.6 |

TABLE 5-continued

| | | Porous Silica | | | | | | | | |
|---|---|---|---|---|---|---|---|---|---|---|
| Item | Evaluation Time | H-1 | I-1 | J-1 | L-1 | M-1 | N-1 | P-1 | Q-1 | R-1 |
| Losses Days with Smaller Losses | Taking off (c) While Putting on | 1.2 | 1.1 | 2.3 | 1.2 | 1.1 | 2.1 | 1.2 | 1.0 | 2.0 |
| | (d) When Taking off | 1.3 | 1.2 | 2.5 | 1.2 | 1.1 | 2.3 | 1.2 | 1.0 | 2.1 |

Example 3-4

The film made of polyethylene resin obtained in Example 3-1 was used as an air-permeable back sheet, a mesh film made of polyolefin resin was used as a liquid-permeable top sheet, and a pulp was used as an absorbent component, to produce a disposable diaper.

The method for evaluating moisture breathability in the following Examples and Comparative Examples is as follows.

[Method for Testing Moisture Breathability]

A test piece having a size of 20 mm×20 mm was cut out from the sheet-like products obtained in Examples described below, and allowed to stand in an atmosphere having a relative humidity of 20% for 100 hours to prepare an experimental sample. This experimental sample was allowed to stand in an atmosphere having a relative humidity of 95%, to determine the moisture content relative to the empty weight (95% RH). The experimental sample was further allowed to stand in an atmosphere having a relative humidity of 95% and thereafter allowed to stand in an atmosphere having a relative humidity of 20% for 100 hours, to determine the moisture content relative to the empty weight (20% RH).

Examples 4-1 to 4-3

Application to Polyvinyl Chloride Resin

The porous silica A-1 prepared above was added in an amount as shown in Table 6 to a composition composed of 100 parts by weight of a polyvinyl chloride (PVC; average degree of polymerization=1,020) as a synthetic resin for preparing a sheet made of polyvinyl chloride resin, 50 parts by weight of DOP (di(2-ethylhexyl)phthalate) as a plasticizer, 1.5 parts by weight of azodicarbonamide as a bubble forming agent (blowing agent), and 3 parts by weight of a Ba—Zn complex stabilizer (a mixture of fatty acid salts of Ba and Zn with an epoxy compound).

The above composition was thoroughly kneaded at room temperature to give a paste-like product. The paste-like product was pre-heated (at 130° C. for 30 minutes) by means of a hot press, thereafter heated at 220° C. for 1 minute, and molded into a sheet having a size of 150 mm×150 mm×1 mm. A test piece having a size of 20 mm×20 mm×1 mm was cut out from the sheet obtained to give a sample, and its moisture breathability was evaluated. The evaluation results are shown in Table 6.

Comparative Examples 4-1 and 4-2

The same procedures and evaluation as in Examples 4-1 to 4-3 were carried out except that the porous silica was not added (Comparative Example 4-1). Also, the same procedures and evaluation as in Examples 4-1 to 4-3 were carried out except that a collagen (collagen particles for synthetic leather, average particle size: 7 μm) was used in an amount as shown in Table 6 in place of the porous silica (Comparative Example 4-2). The evaluation results are shown in Table 6.

Examples 4-4 to 4-6

Examples of Application to Polyurethane Resin

The porous silica A-1 obtained in Preparation Example 1-1 was added in an amount as shown in Table 6 to a composition composed of 100 parts by weight of a polyether polyol (average molecular weight: 3,000), 40 parts by weight of diphenylmethane diisocyanate (pure MDI), 3 parts by weight of water, 0.2 parts by weight of a tertiary amine, and 0.2 parts by weight of tin octylate as a stabilizer.

The above composition was thoroughly mixed, and the mixture was pre-heated (at 130° C. for 30 minutes) by means of a hot press, thereafter heated at 180° C. for 15 minutes, and molded into a sheet having a size of 150 mm×150 mm×1 mm. A test piece having a size of 20 mm×20 mm×1 mm was cut out from the resulting polyurethane (PU) sheet to give a sample, and its moisture breathability was evaluated. The evaluation results are shown in Table 6.

Comparative Examples 4-3 and 4-4

The same procedures and evaluation as in Examples 4-4 to 4-6 were carried out except that the porous silica was not added (Comparative Example 4-3), or that the collagen was added in an amount as shown in Table 6 in place of the porous silica (Comparative Example 4-4), as in Comparative Examples 4-1 and 4-2. The evaluation results are shown in Table 6.

Examples 4-7 and 4-8

Examples of Application to Polyolefin Resin

The amount 0.5 parts by weight of an aliphatic monocarboxylic acid condensate (trade name: CHIRABAZOL H-40, manufactured by Taiyo Kagaku Co., Ltd.) as a viscosity-lowering agent, and the porous silica A-1 obtained in Preparation Example 1-1 in an amount as shown in Table 6 were added to 100 parts by weight of a powdery low-density polyethylene (LPDE [sic]; average degree of polymerization=1, 300, average particle size: about 40 μm). The resulting mixture was melt-kneaded at 140° C., and the melt-kneaded product was extruded at 180° C. from a T dies using an extruder (manufactured by TOSHIBA MACHINE CO., LTD.), to give a film having a width of 50 mm and a thickness of 1 mm. A test piece having a size of 20 mm×20 mm was cut out from the film to give a sample, and its moisture breathability was evaluated. The evaluation results are shown in Table 6.

Comparative Examples 4-5 and 4-6

The same procedures and evaluation as in Examples 4-7 and 4-8 were carried out except that the porous silica was not added (Comparative Example 4-5), or that the collagen was added in place of the porous silica (Comparative Example 4-6), as in Comparative Examples 4-1 and 4-2. The evaluation results are shown in Table 6.

Examples 4-9 and 4-10

Examples of Application to Polyamino Acid Resin

The porous silica A-1 obtained in Preparation Example 1-1 was added in an amount as shown in Table 6 to a dimethylformamide solution of a polyamino acid resin (PAA; average degree of polymerization=2,000) (solid content: 10%). The above composition was thoroughly mixed, and thereafter cast on a glass plate. A test piece having a size of 20 mm×20 mm×1 mm was cut out from the cast glass plate to give a sample, and its moisture breathability was evaluated. The evaluation results are shown in Table 6.

Comparative Examples 4-7 and 4-8

The same procedures and evaluation as in Examples 4-9 and 4-10 were carried out except that the porous silica was not added (Comparative Example 4-7), and that the collagen was used in place of the porous silica (Comparative Example 4-8). The evaluation results are shown in Table 6.

Examples 4-11 and 4-12

Examples of Application to Polyacrylic Acid-Based Resin

One-hundred parts by weight of powder of a polyacrylonitrile resin (PAN; average molecular weight: 50,000) was dissolved in 1,000 parts by weight of dimethylformamide. The porous silica A-1 obtained in Preparation Example 1-1 was added to this solution in an amount as shown in Table 6 while stirring, and the mixture was homogenously kneaded.

This solution was spread over a Teflon (registered trademark) plate using a knife coater (doctor knife coater). The plate was dried at 60° C. for 8 hours and then at 80° C. under a reduced pressure for 8 hours, to give a film having a thickness of 1 mm. A piece having a size of 20 mm×20 mm was cut out from the film to give a sample, and its moisture breathability was evaluated. The evaluation results are shown in Table 6.

Comparative Examples 4-9 and 4-10

The same procedures and evaluation as in Examples 4-11 and 4-12 were carried out except that the porous silica was not added (Comparative Example 4-9), or that the collagen was added in place of the porous silica (Comparative Example 4-10). The evaluation results are shown in Table 6.

Examples 4-13 and 4-14

Examples of Application to Polyacrylic Acid-based Resin

Thirty grams of an acrylic resin varnish (solid contents: 50%) (PA; trade name: HITALOID 1206, manufactured by Hitachi Chemical Co., Ltd.) was mixed with 10 g of ethyl acetate, 10 g of methyl isobutyl ketone, 10 g of isopropyl alcohol, 5 g of butylated Cellosolve, 30 g of toluene and 5 g of dioctyl phthalate. The porous silica A-1 obtained in Preparation Example 1-1 in an amount as shown in Table 6 was added to this liquid mixture, and the mixture was mixed homogenously.

This solution was spread over a copper plate using a knife coater (doctor knife coater), and the copper plate was dried at 60° C. The thickness of the coating film was 100 μm. The coating film adhered to the copper plate was cut into pieces together with the copper plate, each having a size of 20 mm×20 mm to give a sample, and its moisture breathability was evaluated. The evaluation results are shown in Table 6.

Comparative Examples 4-11 and 4-12

The same procedures and evaluation as in Examples 4-13 and 4-14 were carried out except that the porous silica was not added (Comparative Example 4-11), or that the collagen was added in place of the porous silica (Comparative Example 4-12). The evaluation results are shown in Table 6.

[Table 6]

TABLE 6

| | Added | | | Moisture Content | |
|---|---|---|---|---|---|
| | | Component | | 95% | 25% |
| | Resin | Kind | Amount | RH | RH |
| Ex. 4-1 | PVC | Porous Silica | 0.1 | 2.5 | 2.0 |
| Ex. 4-2 | PVC | Porous Silica | 2.0 | 5.5 | 1.5 |
| Ex. 4-3 | PVC | Porous Silica | 10.0 | 7.5 | 2.0 |
| Comp. Ex. 4-1 | PVC | None | 0.0 | 2.0 | 1.0 |
| Comp. Ex. 4-2 | PVC | Collagen | 2.0 | 4.5 | 1.5 |
| Ex. 4-4 | PU | Porous Silica | 0.1 | 10.5 | 10.0 |
| Ex. 4-5 | PU | Porous Silica | 2.0 | 12.5 | 7.0 |
| Ex. 4-6 | PU | Porous Silica | 10.0 | 15.5 | 10.0 |
| Comp. Ex. 4-3 | PU | None | 0.0 | 9.5 | 8.0 |
| Comp. Ex. 4-4 | PU | Collagen | 2.0 | 11.0 | 8.0 |
| Ex. 4-7 | LPDE | Porous Silica | 10.0 | 5.0 | 1.0 |
| Ex. 4-8 | LPDE | Porous Silica | 50.0 | 25.0 | 5.0 |
| Comp. Ex. 4-5 | LPDE | None | 0.0 | 0.1 | 0.1 |
| Comp. Ex. 4-6 | LPDE | Collagen | 10.0 | 3.0 | 1.0 |
| Ex. 4-9 | PAA | Porous Silica | 10.0 | 13.0 | 3.0 |
| Ex. 4-10 | PAA | Porous Silica | 50.0 | 35.0 | 7.0 |
| Comp. Ex. 4-7 | PAA | None | 0.0 | 8.0 | 2.0 |
| Comp. Ex. 4-8 | PAA | Collagen | 10.0 | 10.0 | 3.5 |
| Ex. 4-11 | PAN | Porous Silica | 10.0 | 8.0 | 1.0 |
| Ex. 4-12 | PAN | Porous Silica | 50.0 | 27.0 | 5.5 |
| Comp. Ex. 4-9 | PAN | None | 0.0 | 2.3 | 0.5 |
| Comp. Ex. 4-10 | PAN | Collagen | 10.0 | 6.0 | 1.5 |
| Ex. 4-13 | PA | Porous Silica | 10.0 | 7.5 | 1.0 |
| Ex. 4-14 | PA | Porous Silica | 50.0 | 28.0 | 6.5 |
| Comp. Ex. 4-11 | PA | None | 0.0 | 2.0 | 0.2 |
| Comp. Ex. 4-12 | PA | Collagen | 10.0 | 5.0 | 2.0 |

(Note 1)
PVC: Polyvinyl Chloride Resin
PU: Polyurethane Resin
LDPE: Low-Density Polyethylene Resin
PAA: Polyamino Acid Resin
PAN: Polyacrylonitrile Resin
PA: Acrylic Resin
(Note 2)
The amount of the improver
PVC: An amount based on 100 parts by weight of PVC Resin
PU: An amount based on 100 parts by weight of Polyol/MDI mixture
LDPE: An amount based on 100 parts by weight of LDPE
PAA: An amount based on 100 parts by weight of PAA
PAN: An amount based on 100 parts by weight of PAN
PA: An amount based on 100 parts by weight of PA Examples 4-15 to 4-23 and Comparative Examples 4-13 and 4-14

A polyvinyl chloride resin was applied in the same manner as in Example 4-3, except that H-1, I-1, J-1, L-1, M-1, N-1, P-1, Q-1 or R-1 (Examples 4-15 to 4-23) was used as a porous silica, or that silicic acid anhydride (average particle size: 30 μm, average pore size: 6.5 nm, specific surface area: 450 m²/g) was used in place of the porous silica (Comparative Example 4-13), or that a zeolite (average particle size: 0.6 nm, specific surface area: 380 m²/g) was used in place of the porous silica (Comparative Example 4-14). The evaluation results are shown in Table 7.

[Table 7]

TABLE 7

| | Resin | Component Added Kind | Amount | Moisture Content 95% RH | 25% RH |
|---|---|---|---|---|---|
| Ex. 4-15 | PVC | Porous Silica H-1 | 10.0 | 8.1 | 2.5 |
| Ex. 4-16 | | Porous Silica I-1 | | 10.1 | 3.1 |
| Ex. 4-17 | | Porous Silica J-1 | | 5.1 | 2.2 |
| Ex. 4-18 | | Porous Silica L-1 | | 8.5 | 2.6 |
| Ex. 4-19 | | Porous Silica M-1 | | 10.7 | 3.3 |
| Ex. 4-20 | | Porous Silica N-1 | | 5.3 | 2.3 |
| Ex. 4-21 | | Porous Silica P-1 | | 8.8 | 2.8 |
| Ex. 4-22 | | Porous Silica Q-1 | | 10.9 | 3.4 |
| Ex. 4-23 | | Porous Silica R-1 | | 5.4 | 2.4 |
| Comp. Ex. 4-13 | | Silicic Acid Anhydride | | 3.2 | 1.2 |
| Comp. Ex. 4-14 | | Zeolite | | 3.5 | 1.3 |

Example 5-1

Preparation of Moisture-Controlled Material

The porous silica A-1 obtained in Preparation Example 1-1 was used as a moisture-controlled material. Its moisture breathability was evaluated, and the results are shown in FIG. 2. The figure is a graph showing the results obtained by placing a sample, which had been previously dried in an atmosphere having a relative humidity of 20%, in an atmosphere having a relative humidity of 95%, recording a change in weight, transferring the sample back in an atmosphere having a relative humidity of 20% at a point of reaching an equilibrium state (100 hours after placing the sample in an atmosphere having a relative humidity of 95%), and recording a change in weight. For the sake of comparison, the moisture content of each of a silica gel and a zeolite, ordinarily used as granular filler, is shown together. It can be seen that the porous silica has higher moisture breathability than the silica gel and the zeolite.

Example 5-2

Preparation of Moisture-Controlled Paper

A mixture of an NBKP pulp, a NBSP pulp, and the moisture-controlled material obtained in Example 5-1 (porous silica A-1) in a ratio (NBKP pulp:an NBSP pulp:the moisture-controlled material) of 1:1:1 (weight ratio), a proper amount of water, and as binders a polyacrylamide 0.5% by weight and PVA 5% by weight were placed in a pulp mill, and the mixture was mixed and dispersed, to give a slurry. The slurry suspension was subjected to wet papermaking, to give a paper, and the paper was dried, to give a moisture-controlled paper of 60 g/m².

Example 5-3

Production of Wallpaper

A resin prepared by kneading 300 g of the moisture-controlled material (porous silica A-1) obtained in Example 5-1, 300 g of a polyvinyl chloride, 150 g of a plasticizer (dioctyl phthalate), 30 g of a blowing agent (azodicarbonamide) and 60 g of titanium oxide was applied to a base paper (support) of 75 g/m² with a lip coater so as to have a coating amount after drying of 300 g/m², to produce a wallpaper according to the present invention.

Test Example 5-1

Adsorption Test for Ammonia and Acetaldehyde

A 5-liter teddler pack was charged with 3 liters of a gas, and 0.1 g of the moisture-controlled material obtained in Preparation Example 1-1 (porous silica A-1), or a sample produced by cutting the moisture-controlled paper obtained in Example 5-2 or the wallpaper obtained in Example 5-3 into a size of 10 cm×10 cm was placed in the gas-charged teddler pack. Thereafter, each of ammonia and acetaldehyde was injected. The concentrations of both the components were determined with a gas detecting tube (No. 3L and 92M, manufactured by GASTEC CORPORATION). As a result, the concentration of ammonia was 60 ppm, and that of acetaldehyde was 70 ppm. Subsequently, while stirring the air in the tightly sealed vessel at 23° C. by rotating the agitating fan, the concentrations (ppm) of ammonia and acetaldehyde in the vessel were determined at 10 minutes passed and at 30 minutes passed after the injection with the gas detecting tube described above. The results are shown in Table 8 together with the results of a case where 0.1 g of a commercially available zeolite was placed in the tightly sealed vessel, and a case of a control where a moisture-controlling material, the sample, was not placed in the tightly sealed vessel, for the sake of comparison.

[Table 8]

TABLE 8

| | | Ammonia (ppm) | | Acetaldehyde (ppm) | |
|---|---|---|---|---|---|
| | | After 10 min. | After 30 min. | After 10 min. | After 30 min. |
| Ex. 5-1 | Moisture-Controlled Material | 15 | 5 | 25 | 15 |
| Ex. 5-2 | Moisture-Controlled Paper | 15 | 10 | 30 | 25 |
| Ex. 5-3 | Wallpaper | 15 | 10 | 30 | 25 |
| Comp. Ex. | Zeolite | 50 | 45 | 65 | 60 |
| Control Ex. | Without Sample | 60 | 60 | 70 | 70 |

It could be seen from the test results that the moisture-controlled material and an article using the material according to the present invention shows excellent adsorbability for ammonia, which was a causative of foul odor, and for acetaldehyde, which was a causative of sick house syndrome.

Test Example 5-2

Wallpaper was produced in the same manner as in Example 5-3 except that the porous silica H-1, I-1, J-1, L-1, M-1, N-1, P-1, Q-1 or R-1 or a zeolite (average particle size: 0.6 nm, specific surface area 380 m²/g) was used in place of the porous silica. A test was conducted in the same manner as in Test Example 5-1 for each of the wallpapers obtained. The results are shown in Table 9.

TABLE 9

| | Ammonia (ppm) | | Acetaldehyde (ppm) | |
|---|---|---|---|---|
| | After 10 min. | After 30 min. | After 10 min. | After 30 min. |
| Porous Silica H-1 | 13 | 8 | 23 | 13 |
| Porous Silica I-1 | 9 | 6 | 18 | 9 |
| Porous Silica J-1 | 28 | 18 | 51 | 45 |
| Porous Silica L-1 | 11 | 7 | 21 | 12 |
| Porous Silica M-1 | 8 | 5 | 15 | 8 |
| Porous Silica N-1 | 26 | 21 | 48 | 41 |
| Porous Silica P-1 | 10 | 6 | 19 | 10 |
| Porous Silica Q-1 | 6 | 5 | 13 | 6 |
| Porous Silica R-1 | 24 | 19 | 45 | 38 |
| Zeolite | 45 | 42 | 61 | 52 |

Example 6-1

Application Example of Cream-Type Wound Covering Material

Each of the formulation components having a composition as shown in the following Table 10 were mixed using a homo-mixer with rotational blades, to give a cream-type wound covering material. This wound covering material was applied to an abrasion. As a result, hardly any bleeding and effusion were found, showing recovery.

TABLE 10

| Formulated Components | Weight (g) |
|---|---|
| Porous Silica of Preparation Example 1-1 | 20 |
| Propylene Glycol | 8 |
| Glycerol | 1 |
| Purified Water | 51 |

Example 6-2

Application Example of Cream-Type Wound Covering Material

Each of the formulation components having a composition as shown in the following Table 11 were mixed in the same manner as in Example 6-1, to give a cream-type wound covering material. This wound covering material was applied to an abrasion. As a result, hardly any bleeding and effusion were found, showing recovery.

TABLE 11

| Formulated Components | Weight (g) |
|---|---|
| Porous Silica of Preparation Example 1-1 | 20 |
| Polyvinyl Alcohol (35-45 cps) | 3 |
| Ethanol | 20 |
| Propylene Glycol | 3 |
| Glycerol | 1 |
| Purified Water | 53 |

Example 6-3

Application Example of Cream-Type Wound Covering Material

Each of the formulation components having a composition as shown in the following Table 12 were mixed in the same manner as in Example 6-1, to give a cream-type wound covering material. This wound covering material was applied to an abrasion. As a result, hardly any bleeding and effusion were found, showing recovery.

TABLE 12

| Formulated Components | Weight (g) |
|---|---|
| Porous Silica of Preparation Example 1-1 | 20 |
| Sulfated Cellulose (Degree of Sulfation DS-0.07) | 10 |
| Sodium Carboxymethyl Cellulose (Degree of Polymerization: about 250) | 0.5 |
| Polyvinyl Alcohol (35-45 cps) | 10 |
| Ethanol | 20 |
| Propylene Glycol | 3 |
| Glycerol | 1 |
| Purified Water | 35.5 |

Example 6-4

Application Example of Aerosol-Type (Powder Spray) Wound Covering Material

Each of the formulation components, except a liquefied petroleum gas, having a composition as shown in the following Table 13 was mixed in the same manner as in Example 6-1, and the mixture was filled in a spray can. Subsequently, the liquefied petroleum gas was filled in the can, to give an aerosol-type (powder spray) wound covering material. This wound covering material was sprayed over an abrasion. As a result, hardly any bleeding and effusion were found, showing recovery.

TABLE 13

| Formulated Component | Weight (g) |
|---|---|
| Porous Silica of Preparation Example 1-1 | 12 |
| Polyvinyl Alcohol (35-45 cps) | 0.5 |
| Polyoxyethylene Sorbitan Monooleate | 0.1 |
| Silicic Acid Anhydride | 0.5 |
| Liquefied Petroleum Gas | 86.9 |

Example 6-5

Application Example of Aerosol-Type (Powder Spray) Wound Covering Material

Each of the formulation components having a composition as shown in the following Table 14 were mixed in the same manner as in Example 6-4, and the mixture was filled in a spray can, to give an aerosol-type (powder spray) wound covering material. This wound covering material was sprayed over an abrasion. As a result, hardly any bleeding and effusion were found, showing recovery.

[Table 14]

TABLE 14

| Formulated Component | Weight (g) |
|---|---|
| Porous Silica of Preparation Example 1-1 | 7 |
| Polydimethyl siloxane | 0.1 |
| Isopropyl Myristate | 0.5 |
| Polyvinyl Alcohol (35-45 cps) | 0.5 |
| Polyoxyethylene Sorbitan Monooleate | 0.1 |
| Silicic Acid Anhydride | 0.5 |
| Liquefied Petroleum Gas | 91.3 |

Example 6-6

Application Example of Aerosol-Type (Powder Spray) Wound Covering Material

Each of the formulation components having a composition as shown in the following Table 15 were mixed in the same manner as in Example 6-4, and the mixture was filled in a spray can, to give an aerosol-type (powder spray) wound covering material. This wound covering material was sprayed over an abrasion. As a result, hardly any bleeding and effusion were found, showing recovery.

[Table 15]

TABLE 15

| Formulated Component | Weight (g) |
|---|---|
| Porous Silica of Preparation Example 1-1 | 8 |
| Poly(dimethyl siloxane) | 0.1 |
| Isopropyl Myristate | 0.5 |
| Polyvinyl Alcohol (35-45 cps) | 0.5 |
| Polyoxyethylene Sorbitan Monooleate | 0.1 |
| Silicic Acid Anhydride | 0.1 |
| Acrinol | 0.2 |
| Allantoin | 0.7 |
| d-Camphor | 0.5 |
| Liquefied Petroleum Gas | 89.3 |

Comparative Example 6-1

Application Example of Cream-Type Wound Covering Material

Each of the formulation components having a composition as shown in the following Table 16 were mixed in the same manner as in Example 6-1, to give a cream-type wound covering material. This cream-type wound covering material was applied to an abrasion. As a result, hardly any effects of stopping the bleeding and absorbing effusion could be found.

[Table 16]

TABLE 16

| Formulated Components | Weight (g) |
|---|---|
| Ethanol | 20 |
| Propylene Glycol | 8 |
| Glycerol | 1 |
| Purified Water | 51 |

Comparative Example 6-2

Application Example of Aerosol-Type (Powder Spray) Wound Covering Material

Each of the formulation components having a composition as shown in the following Table 17 were mixed in the same manner as in Example 6-4, and the mixture was filled in a spray can, to give an aerosol-type (powder spray) wound covering material. This wound covering material was sprayed over an abrasion. As a result, no effect of applying the wound covering material could be found.

[Table 17]

TABLE 17

| Formulated Component | Weight (g) |
|---|---|
| Poly(dimethyl siloxane) | 0.1 |
| Isopropyl Myristate | 0.5 |
| Polyvinyl Alcohol (35-45 cps) | 0.5 |
| Polyoxyethylene Sorbitan Monooleate | 0.1 |
| Silicic Acid Anhydride | 0.5 |
| Liquefied Petroleum Gas | 98.3 |

Examples 6-17 to 6-18 and Comparative Examples 6-3

Cream-Type Wound Covering Material

Each of the components having a composition as shown in the following Table 18 were mixed using a homomixer, to give a cream-type wound covering material. A total of 10 kinds of the wound covering materials obtained and a wound covering material produced for use in comparison were applied to abrasions of 50 male subjects in their twenties and thirties, and the questionnaire survey was conducted on the subjects. The feel of the covering effect was evaluated with 10 ranks in scores 10 to 1 (starting from that in which its covering effect was felt), and an average of the 50 subjects was obtained. The results are shown in Table 18.

[Table 18]

TABLE 18

| | | Ex. | | | | | | | | | | | Comp. Ex. |
|---|---|---|---|---|---|---|---|---|---|---|---|---|---|
| | | 6-7 | 6-8 | 6-9 | 6-10 | 6-11 | 6-12 | 6-13 | 6-14 | 6-15 | 6-16 | 6-17 | 6-18 | 6-3 |
| Porous Silica (g) | A-1 | 20 | — | — | — | — | — | — | — | — | — | — | — | — |
| | H-1 | — | — | — | 20 | — | — | — | — | — | — | — | — | — |
| | I-1 | — | — | — | — | — | — | 20 | — | — | — | — | — | — |
| | J-1 | — | — | — | — | — | — | — | — | — | 20 | — | — | — |
| | K-1 | — | 20 | — | — | — | — | — | — | — | — | — | — | — |
| | L-1 | — | — | — | — | 20 | — | — | — | — | — | — | — | — |
| | M-1 | — | — | — | — | — | — | — | 20 | — | — | — | — | — |
| | N-1 | — | — | — | — | — | — | — | — | — | — | 20 | — | — |
| | O-1 | — | — | 20 | — | — | — | — | — | — | — | — | — | — |
| | P-1 | — | — | — | — | — | 20 | — | — | — | — | — | — | — |

TABLE 18-continued

|  | Ex. | | | | | | | | | | | | Comp. Ex. |
|---|---|---|---|---|---|---|---|---|---|---|---|---|---|
|  | 6-7 | 6-8 | 6-9 | 6-10 | 6-11 | 6-12 | 6-13 | 6-14 | 6-15 | 6-16 | 6-17 | 6-18 | 6-3 |
| Q-1 | — | — | — | — | — | — | — | — | 20 | — | — | — | — |
| R-1 | — | — | — | — | — | — | — | — | — | — | — | 20 | — |
| Silicic Acid Anhydride (g) | — | — | — | — | — | — | — | — | — | — | — | — | 20 |
| Propylene Glycol (g) | 8 | 8 | 8 | 8 | 8 | 8 | 8 | 8 | 8 | 8 | 8 | 8 | 8 |
| Glycerol (g) | 1 | 1 | 1 | 1 | 1 | 1 | 1 | 1 | 1 | 1 | 1 | 1 | 1 |
| Purified Water (g) | 51 | 51 | 51 | 51 | 51 | 51 | 51 | 51 | 51 | 51 | 51 | 51 | 51 |
| Evaluation | 6.3 | 6.5 | 6.8 | 6.9 | 7.5 | 8.1 | 8.3 | 8.9 | 9.2 | 4.3 | 4.5 | 4.6 | 1.2 |

Examples 6-19 to 6-26 and Comparative Example 6-4

(Powder Spray) Wound Covering Material

Each of the formulation components, except a liquefied petroleum gas, having a composition as shown in Table 19 was mixed using a homomixer, and the mixture was filled in a spray can. Subsequently, the liquefied petroleum gas was filled in the can, to give an aerosol-type (powder spray) wound covering material. A total of 10 kinds of the wound covering materials and a wound covering material for use in comparison were applied to abrasions of 50 male subjects in their twenties and thirties, and the questionnaire survey was conducted on the subjects. The feel of the covering effect was evaluated with 10 ranks in scores 10 to 1 (starting from that in which its covering effect was felt), and an average from the 50 subjects was obtained. The results are shown in Table 19.

[Table 19]

Examples 7-1 to 7-3 and Comparative Examples 7-1 to 7-3

A cresol-novolak type epoxy resin as an epoxy resin (YDCN-702S, manufactured by Tohto Kasei Co., Ltd.), a phenol-novolak resin as a phenol resin (H-1, manufactured by MEIWA PLASTIC INDUSTRIES, LTD.), 2-ethyl-4-methylimidazole, carnauba wax (manufactured by CERARICA NODA Co., Ltd, purified carnauba wax No. 1), γ-glycidoxypropyl trimethoxysilane (KBM403, manufactured by Shin-Etsu Chemical Co., Ltd.) as a silane coupling agent, antimony trioxide, the porous silica A-2 prepared in Preparation Example 2-1 or a fused silica (3K, manufactured by TATSUMORI), SUNSOFT No. 818H (manufactured by Taiyo Kagaku Co., Ltd.) as a polyglycerol fatty acid ester obtained by esterifying a polyglycerol having an average degree of polymerization of 3 or more with a fatty acid, and SUNLECITHIN A (manufactured by Taiyo Kagaku Co., Ltd.) as a

TABLE 19

|  |  | Ex. | | | | | | | | Comp. Ex. |
|---|---|---|---|---|---|---|---|---|---|---|
|  |  | 6-19 | 6-20 | 6-21 | 6-22 | 6-23 | 6-24 | 6-25 | 6-26 | 6-4 |
| Porous Silica (g) | A-1 | 12 | — | — | — | — | — | — | — | — |
|  | H-1 | — | — | 12 | — | — | — | — | — | — |
|  | I-1 | — | — | — | — | 12 | — | — | — | — |
|  | J-1 | — | — | — | — | — | — | 12 | — | — |
|  | K-1 | — | 12 | — | — | — | — | — | — | — |
|  | L-1 | — | — | — | 12 | — | — | — | — | — |
|  | M-1 | — | — | — | — | — | 12 | — | — | — |
|  | N-1 | — | — | — | — | — | — | — | 12 | — |
| Silicic Acid Anhydride (g) |  | — | — | — | — | — | — | — | — | 12 |
| Polyvinyl Alcohol (35-45 cps) |  | 0.5 | 0.5 | 0.5 | 0.5 | 0.5 | 0.5 | 0.5 | 0.5 | 0.5 |
| Polyoxyethylene Sorbitan Monooleate |  | 0.1 | 0.1 | 0.1 | 0.1 | 0.1 | 0.1 | 0.1 | 0.1 | 0.1 |
| Liquefied Petroleum Gas (g) |  | 87.4 | 87.4 | 87.4 | 87.4 | 87.4 | 87.4 | 87.4 | 87.4 | 87.4 |
| Evaluation |  | 6.4 | 6.6 | 7.4 | 7.9 | 8.7 | 9.3 | 5.3 | 5.5 | 1.5 | lecithin were mixed in a composition as shown in Table 20, to give a composition for an insulating substrate or coating material. Incidentally, the expressions "%" in the table all mean "% by weight."

The resulting compositions were subjected to a determination for the flexural strength according to a method as prescribed in JIS K-6911, and flexural modulus was evaluated.

[Table 20]

TABLE 20

|  | Ex. | | | Comp. Ex. | | |
| --- | --- | --- | --- | --- | --- | --- |
|  | 7-1 | 7-2 | 7-3 | 7-1 | 7-2 | 7-3 |
| Epoxy Resin | 12 | 12 | 12 | 12 | 12 | 12 |
| Phenol Resin | 6.5 | 6.5 | 6.5 | 6.5 | 6.5 | 6.5 |
| 2-Ethyl 4-methylimidazole | 0.2 | 0.2 | 0.2 | 0.2 | 0.2 | 0.2 |
| Carnauba Wax | 0.2 | 0.2 | 0.2 | 0.2 | 0.2 | 0.2 |
| Silane Coupling Agent | 0.2 | 0.2 | 0.2 | 0.2 | 0.2 | 0.2 |
| Antimony Trioxide | 0.9 | 0.9 | 0.9 | 0.9 | 0.9 | 0.9 |
| Porous Silica | 80 | 70 | 70 | — | — | — |
| Fused Silica | — | — | — | 80 | 70 | 70 |
| Polyglycerol Fatty Acid Ester | — | 10 | 5 | — | 10 | 5 |
| Lecithin | — | — | 5 | — | — | 5 |
| Flexural Modulus (GPa) | 20 | 21 | 22 | 14 | 13 | 10 |

Examples 7-4 to 7-9 and Comparative Examples 7-4 to 7-9

First, a premolding type semiconductor device was produced as follows (Examples 7-4 to 7-6, and Comparative Examples 7-4 to 7-6), and each semiconductor device was evaluated for the items mentioned below. Each of the compositions prepared in Examples 7-1 to 7-3 or Comparative Examples 7-1 to 7-3 was injected into a given die to which an external lead was set, and the composition was allowed to be thermally cured at a temperature of from 150° to 200° C., to produce a package for housing a semiconductor. Next, semiconductor elements were mounted on the package for housing a semiconductor using a bonding machine, and the semiconductor elements and an external lead terminal were electrically connected with a wire holder. Thereafter, a glass lid member was bonded to the package for housing a semiconductor with a bisphenol A type epoxy encapsulating agent. Here, the composition used in each of Examples and Comparative Examples is shown in Table 21.

Next, a molding type semiconductor device was produced as follows (Examples 7-7 to 7-9 and Comparative Examples 7-7 to 7-9), and each semiconductor device was evaluated for the items mentioned below. Semiconductor elements were mounted and fixed on a substrate, and the semiconductor elements were electrically connected to an external lead terminal with a bonding wire. Thereafter, the semiconductor elements-mounted substrate was set in a jig, and each of the compositions prepared in Examples 7-1 to 7-3 or Comparative Examples 7-1 to 7-3 was injected into the jig. The composition was allowed to thermally cured at 180° C. while applying a pressure of 100 kgf/mm$^2$, to produce a molding type semiconductor device. Here, the composition used in each of Examples and Comparative Examples is shown in Table 21.

[Table 21]

TABLE 21

| | Type of Semiconductor Device | Composition Used |
| --- | --- | --- |
| Ex. 7-4 | Premolding | Ex. 7-1 |
| Ex. 7-5 | Premolding | Ex. 7-2 |
| Ex. 7-6 | Premolding | Ex. 7-3 |
| Ex. 7-7 | Molding | Ex. 7-1 |
| Ex. 7-8 | Molding | Ex. 7-2 |
| Ex. 7-9 | Molding | Ex. 7-3 |
| Comp. Ex. 7-4 | Premolding | Comp. Ex. 7-1 |
| Comp. Ex. 7-5 | Premolding | Comp. Ex. 7-2 |
| Comp. Ex. 7-6 | Premolding | Comp. Ex. 7-3 |
| Comp. Ex. 7-7 | Molding | Comp. Ex. 7-1 |
| Comp. Ex. 7-8 | Molding | Comp. Ex. 7-2 |
| Comp. Ex. 7-9 | Molding | Comp. Ex. 7-3 |

<Amount of Deflection>

The amount of deflection was determined by a point deflection under load when a point load of 58.8 N was applied with a rigid sphere having a diameter of 4 mm to the central portion of a back side of the semiconductor device produced above.

<Connection Reliability>

Ten semiconductors produced above were allowed to stand in an environment of 85° C. and a relative humidity of 85% for 1,000 hours, and thereafter the conductivity resistance between the leads was determined with a digital multimeter (TR6847, manufactured by ADVANTEST) for each of the semiconductor devices, to detect the presence or absence of the indication of the resistance. Those not indicating the resistance were counted as connection failure, and the connection reliability was evaluated.

<Moisture Tolerance>

Each of the resulting semiconductor devices was subjected to a pressure cooker test (hereinafter also referred to as PCT) in a saturated steam at 121° C. and 2.1×10$^5$ Pa. The moisture tolerance was evaluated by a time period until dew condensation was generated on the inner surface of the lid for the premolding type semiconductor devices, and evaluated by a PCT introduction time until moisture tolerance failure was generated when the semiconductor device was soaked in a solder layer at 260° C. for 5 seconds after subjecting the semiconductor device to a PCT for the molding type semiconductor devices.

[Table 22]

TABLE 22

| | Amount of Deflection (μm) | Connection Reliability | Moisture Tolerance (hr) |
| --- | --- | --- | --- |
| Ex. 7-4 | 42 | 0/10 | 54 |
| Ex. 7-5 | 40 | 0/10 | 55 |
| Ex. 7-6 | 38 | 0/10 | 55 |
| Ex. 7-7 | 37 | 0/10 | 57 |
| Ex. 7-8 | 36 | 0/10 | 57 |
| Ex. 7-9 | 34 | 0/10 | 58 |
| Comp. Ex. 7-4 | >50 | 7/10 | 25 |
| Comp. Ex. 7-5 | >50 | 8/10 | 23 |
| Comp. Ex. 7-6 | >50 | 8/10 | 22 |

TABLE 22-continued

| | Amount of Deflection (μm) | Connection Reliability | Moisture Tolerance (hr) |
|---|---|---|---|
| Comp. Ex. 7-7 | >50 | 4/10 | 26 |
| Comp. Ex. 7-8 | >50 | 5/10 | 24 |
| Comp. Ex. 7-9 | >50 | 5/10 | 23 |

It can be seen from Tables 20 and 22 that in Comparative Examples 7-4 and 7-7, flexural moduli of the cured products of the compositions were as low as 15 GPa or less, so that the amounts of deflection were as large as 50 μm, and 40% or more failure was generated in connection reliability. Also, in the semiconductors using the composition containing a polyglycerol fatty acid ester (Comparative Examples 7-5 and 7-8), or the composition containing a polyglycerol fatty acid ester and a lecithin (Comparative Examples 7-6 and 7-9), flexural moduli of the cured products of the compositions were as low as 15 GPa or less, so that the amounts of deflection were as large as 50 μm.

On the other hand, in the cases of Examples 7-4 and 7-7, flexural moduli of the cured products of the compositions were as high as 20 GPa, so that the amounts of deflection were as small as 37 to 42 μm, and that no failure was generated in connection reliability. Further, in the semiconductor devices using the compositions containing a polyglycerol fatty acid ester (Examples 7-5 and 7-8), flexural moduli of the cured products of the compositions were as high as 21 GPa, so that the amounts of deflection were as small as 36 to 40 μm, in the semiconductor devices using the compositions containing a polyglycerol fatty acid ester and a lecithin (Examples 7-6 and 7-9), flexural moduli of the cured products of the compositions were even as high as 22 GPa, so that the amounts of deflection were as small as 34 to 38 μm.

Examples 7-10 to 7-31

The same procedures as in Example 7-1 were carried out except that porous silica F-2, G-2, H-2, I-2, J-2, K-2, L-2, M-2, N-2, O-2 or P-2 was used, to prepare a composition, and premolding type semiconductor devices and molding type semiconductor devices were produced. A test was conducted in the same manner as in Examples mentioned above for the semiconductor devices obtained. The results are shown in Table 23.

[Table 23]

TABLE 23

| Ex. No. | Porous Silica | Type of Semiconductor | Amount of Deflection (μm) | Moisture Tolerance (hr) |
|---|---|---|---|---|
| 7-10 | F-2 | Premolding | 40 | 56 |
| 7-11 | G-2 | Premolding | 32 | 63 |
| 7-12 | H-2 | Premolding | 48 | 39 |
| 7-13 | I-2 | Premolding | 40 | 55 |
| 7-14 | J-2 | Premolding | 38 | 58 |
| 7-15 | K-2 | Premolding | 28 | 68 |
| 7-16 | L-2 | Premolding | 47 | 40 |
| 7-17 | M-2 | Premolding | 38 | 55 |
| 7-18 | N-2 | Premolding | 35 | 59 |
| 7-19 | O-2 | Premolding | 26 | 71 |
| 7-20 | P-2 | Premolding | 45 | 41 |
| 7-21 | F-2 | Molding | 35 | 59 |
| 7-22 | G-2 | Molding | 31 | 65 |

TABLE 23-continued

| Ex. No. | Porous Silica | Type of Semiconductor | Amount of Deflection (μm) | Moisture Tolerance (hr) |
|---|---|---|---|---|
| 7-23 | H-2 | Molding | 45 | 43 |
| 7-24 | I-2 | Molding | 36 | 57 |
| 7-25 | J-2 | Molding | 33 | 61 |
| 7-26 | K-2 | Molding | 29 | 67 |
| 7-27 | L-2 | Molding | 43 | 41 |
| 7-28 | M-2 | Molding | 34 | 58 |
| 7-29 | N-2 | Molding | 31 | 63 |
| 7-30 | O-2 | Molding | 27 | 69 |
| 7-31 | P-2 | Molding | 40 | 39 |

Test Example 8-1

The adsorption properties of the porous silicas A-3, B-3, C-3, E-3, and F-3 and silicic acid anhydride (average particle size: 30 μm, average pore size: 6.5 nm, specific surface area: 450m$^2$/g) obtained in Preparation Examples 3-1, 3-2, 3-3, 3-5, and 3-6 using an amount of chlorophyll adsorption as an index. The results are shown in Table 24.

[Table 24]

TABLE 24

| | Amount of Chlorophyll Adsorption (mg) |
|---|---|
| Porous Silica A-3 | 23.1 |
| Porous Silica B-3 | 27.8 |
| Porous Silica C-3 | 20.8 |
| Porous Silica E-3 | 6.1 |
| Porous Silica F-3 | 7.5 |
| Silicic Acid Anhydride | 0.1 |

It can be seen from Table 24 that the amounts of chlorophyll adsorbed to the porous silicas E-3 and F-3 are larger, and the amount adsorbed to the porous silicas A-3 and C-3 are even larger, and the amount adsorbed to the porous silica B-3 is even larger, as compared to that of silicic acid anhydride.

Examples 8-1 to 8-18 and Comparative Example 8-1

A transparent pressure-tight container having an inner diameter of 30 mm and an inner volume of 80 mL was charged with 100 mL of a suspension prepared by mixing chlorohydroxy aluminum, talc, isopropyl myristate, dimethyl ether, the porous silicas A-3 to F-3 obtained in Preparation Examples 3-1 to 3-6, the porous silicas G-3 to R-3 containing an emulsifying agent obtained in Preparation Examples 3-7 to 3-10, and silicic acid anhydride (average particle size: 30 μm, average pore size: 6.5 nm, and specific surface area: 450 m$^2$/g) in a composition as shown in Table 25, to give an aerosol-type antiperspirant.

[Table 25]

TABLE 25

| | Weight (mg) | | | | | | | | | |
|---|---|---|---|---|---|---|---|---|---|---|
| | Ex. | | | | | | | | | |
| | 8-1 | 8-2 | 8-3 | 8-4 | 8-5 | 8-6 | 8-7 | 8-8 | 8-9 | 8-10 |
| Chlorohydroxy Aluminum | 1.32 | 1.32 | 1.32 | 1.32 | 1.32 | 1.32 | 1.32 | 1.32 | 1.32 | 1.32 |
| Talc | 0.99 | 0.99 | 0.99 | 0.99 | 0.99 | 0.99 | 0.99 | 0.99 | 0.99 | 0.99 |
| Isopropyl Myristate | 0.99 | 0.99 | 0.99 | 0.99 | 0.99 | 0.99 | 0.99 | 0.99 | 0.99 | 0.99 |
| Dimethyl Ether | 95 | 95 | 95 | 95 | 95 | 95 | 95 | 95 | 95 | 95 |
| Silicic Acid Anhydride | — | — | — | — | — | — | — | — | — | — |
| Porous Silica A-3 | 1.7 | — | — | — | — | — | — | — | — | — |
| Porous Silica B-3 | — | 1.7 | — | — | — | — | — | — | — | — |
| Porous Silica C-3 | — | — | 1.7 | — | — | — | — | — | — | — |
| Porous Silica D-3 | — | — | — | 1.7 | — | — | — | — | — | — |
| Porous Silica E-3 | — | — | — | — | 1.7 | — | — | — | — | — |
| Porous Silica F-3 | — | — | — | — | — | 1.7 | — | — | — | — |
| Porous Silica G-3 | — | — | — | — | — | — | 1.7 | — | — | — |
| Porous Silica H-3 | — | — | — | — | — | — | — | 1.7 | — | — |
| Porous Silica I-3 | — | — | — | — | — | — | — | — | 1.7 | — |
| Porous Silica J-3 | — | — | — | — | — | — | — | — | — | 1.7 |

| | Ex. | | | | | | | | Comp. Ex. |
|---|---|---|---|---|---|---|---|---|---|
| | 8-11 | 8-12 | 8-13 | 8-14 | 8-15 | 8-16 | 8-17 | 8-18 | 8-1 |
| Chlorohydroxy Aluminum | 1.32 | 1.32 | 1.32 | 1.32 | 1.32 | 1.32 | 1.32 | 1.32 | 1.32 |
| Talc | 0.99 | 0.99 | 0.99 | 0.99 | 0.99 | 0.99 | 0.99 | 0.99 | 0.99 |
| Isopropyl Myristate | 0.99 | 0.99 | 0.99 | 0.99 | 0.99 | 0.99 | 0.99 | 0.99 | 0.99 |
| Dimethyl Ether | 95 | 95 | 95 | 95 | 95 | 95 | 95 | 95 | 95 |
| Silicic Acid Anhydride | — | — | — | — | — | — | — | — | 1.7 |
| Porous Silica K-3 | 1.7 | — | — | — | — | — | — | — | — |
| Porous Silica L-3 | — | 1.7 | — | — | — | — | — | — | — |
| Porous Silica M-3 | — | — | 1.7 | — | — | — | — | — | — |
| Porous Silica N-3 | — | — | — | 1.7 | — | — | — | — | — |
| Porous Silica O-3 | — | — | — | — | 1.7 | — | — | — | — |
| Porous Silica P-3 | — | — | — | — | — | 1.7 | — | — | — |
| Porous Silica Q-3 | — | — | — | — | — | — | 1.7 | — | — |
| Porous Silica R-3 | — | — | — | — | — | — | — | 1.7 | — |

[Table 26]

Questionnaire survey was conducted on 15 males and 15 females as subjects, whose ages range from 20 to 30 years old, for dry and smooth feel, and extent of outstandingness of whiteness after use, after the subjects were asked to use each of the antiperspirants of Examples 8-1 to 8-18 and Comparative Examples 8-1 after sweating indoors at 30° C. and a humidity of 70% for 1 hour. The dry and smooth feel was evaluated with 10 ranks in scores 10 to 1, starting from that having the most excellent dry and smooth feel after use, and the extent of outstandingness of whiteness after use was evaluated with 10 ranks in scores 10 to 1, starting from that that is least outstanding, and an average from the 30 subjects was calculated. The results are shown in Table 26.

[Table 27]

TABLE 26

| | Dry and Smooth Feel After Use | Extent of Outstandingness of Whiteness After Use |
|---|---|---|
| Ex. 8-1 | 6.1 | 6.5 |
| Ex. 8-2 | 7.3 | 8.1 |
| Ex. 8-3 | 6.2 | 6.3 |
| Ex. 8-4 | 6.4 | 6.2 |
| Ex. 8-5 | 4.5 | 5.9 |
| Ex. 8-6 | 4.6 | 5.5 |
| Ex. 8-7 | 7.3 | 7.5 |
| Ex. 8-8 | 8.6 | 9.3 |
| Ex. 8-9 | 6.4 | 7.2 |
| Ex. 8-10 | 6.5 | 7.0 |
| Ex. 8-11 | 4.6 | 5.9 |
| Ex. 8-12 | 4.8 | 6.1 |
| Ex. 8-13 | 7.3 | 7.5 |
| Ex. 8-14 | 8.6 | 9.3 |
| Ex. 8-15 | 7.9 | 7.9 |
| Ex. 8-16 | 9.2 | 9.7 |
| Ex. 8-17 | 6.2 | 6.6 |
| Ex. 8-18 | 7.2 | 8.2 |
| Comp. Ex. 8-1 | 2.9 | 1.9 |

It can be seen from Table 26 that the antiperspirants containing the porous silicas A-3 to F-3 of Examples 8-1 to 8-6 are more excellent in dry and smooth feel and have smaller extent of outstandingness of whiteness after use, as compared to those of the antiperspirant containing silicic acid anhydride of Comparative Example 8-1. Also, it can be seen that the antiperspirants containing the porous silicas G-3 to R-3 of Examples 8-7 to 8-18 containing an emulsifying agent are even more excellent in dry and smooth feel and have smaller extent of outstandingness of whiteness after use, Examples 8-19 to 8-36 and Comparative Example 8-2

Talc, mica, titanium oxide, red iron oxide, yellow iron oxide, black iron oxide, methylphenyl polysiloxane, glycerol trioctanate, squalane, a preservative, a flavor, and one of the porous silicas A-3 to F-3 obtained in Preparation Examples 3-1 to 3-6, the porous silicas G-3 to R-3 containing an emulsifying agent obtained in Preparation Examples 3-7 to 3-10, and silicic acid anhydride were mixed in a composition as shown in Table 27, and the mixture was pulverized and sieved. The resulting product was subjected to a compression molding on a metal plate, to give a powder foundation.

[Table 28]

TABLE 27

Weight (mg)

| | Ex. | | | | | | | | | | |
|---|---|---|---|---|---|---|---|---|---|---|---|
| | 8-19 | 8-20 | 8-21 | 8-22 | 8-23 | 8-24 | 8-25 | 8-26 | 8-27 | 8-28 | 8-29 |
| Talc | 30 | 30 | 30 | 30 | 30 | 30 | 30 | 30 | 30 | 30 | 30 |
| Mica | 33.2 | 33.2 | 33.2 | 33.2 | 33.2 | 33.2 | 33.2 | 33.2 | 33.2 | 33.2 | 33.2 |
| Titanium Oxide | 10 | 10 | 10 | 10 | 10 | 10 | 10 | 10 | 10 | 10 | 10 |
| Red Iron Oxide | 1.0 | 1.0 | 1.0 | 1.0 | 1.0 | 1.0 | 1.0 | 1.0 | 1.0 | 1.0 | 1.0 |
| Yellow Iron Oxide | 3.0 | 3.0 | 3.0 | 3.0 | 3.0 | 3.0 | 3.0 | 3.0 | 3.0 | 3.0 | 3.0 |
| Black Iron Oxide | 0.4 | 0.4 | 0.4 | 0.4 | 0.4 | 0.4 | 0.4 | 0.4 | 0.4 | 0.4 | 0.4 |
| Polymethyl Sil(sesqui)oxane | 5.0 | 5.0 | 5.0 | 5.0 | 5.0 | 5.0 | 5.0 | 5.0 | 5.0 | 5.0 | 5.0 |
| Methylphenyl Polysiloxane | 5.0 | 5.0 | 5.0 | 5.0 | 5.0 | 5.0 | 5.0 | 5.0 | 5.0 | 5.0 | 5.0 |
| Glycerol Trioctanate | 2.0 | 2.0 | 2.0 | 2.0 | 2.0 | 2.0 | 2.0 | 2.0 | 2.0 | 2.0 | 2.0 |
| Squalane | 5.0 | 5.0 | 5.0 | 5.0 | 5.0 | 5.0 | 5.0 | 5.0 | 5.0 | 5.0 | 5.0 |
| Preservative | 0.2 | 0.2 | 0.2 | 0.2 | 0.2 | 0.2 | 0.2 | 0.2 | 0.2 | 0.2 | 0.2 |
| Flavor | 0.2 | 0.2 | 0.2 | 0.2 | 0.2 | 0.2 | 0.2 | 0.2 | 0.2 | 0.2 | 0.2 |
| Porous Silica A-3 | 5.0 | — | — | — | — | — | — | — | — | — | — |
| Porous Silica B-3 | — | 5.0 | — | — | — | — | — | — | — | — | — |
| Porous Silica C-3 | — | — | 5.0 | — | — | — | — | — | — | — | — |
| Porous Silica D-3 | — | — | — | 5.0 | — | — | — | — | — | — | — |
| Porous Silica E-3 | — | — | — | — | 5.0 | — | — | — | — | — | — |
| Porous Silica F-3 | — | — | — | — | — | 5.0 | — | — | — | — | — |
| Porous Silica G-3 | — | — | — | — | — | — | 5.0 | — | — | — | — |
| Porous Silica H-3 | — | — | — | — | — | — | — | 5.0 | — | — | — |
| Porous Silica I-3 | — | — | — | — | — | — | — | — | 5.0 | — | — |
| Porous Silica J-3 | — | — | — | — | — | — | — | — | — | 5.0 | — |
| Porous Silica K-3 | — | — | — | — | — | — | — | — | — | — | 5.0 |

| | Ex. | | | | | | | Comp. Ex. |
|---|---|---|---|---|---|---|---|---|
| | 8-30 | 8-31 | 8-32 | 8-33 | 8-34 | 8-35 | 8-36 | 8-2 |
| Talc | 30 | 30 | 30 | 30 | 30 | 30 | 30 | 30 |
| Mica | 33.2 | 33.2 | 33.2 | 33.2 | 33.2 | 33.2 | 33.2 | 33.2 |
| Titanium Oxide | 10 | 10 | 10 | 10 | 10 | 10 | 10 | 10 |
| Red Iron Oxide | 1.0 | 1.0 | 1.0 | 1.0 | 1.0 | 1.0 | 1.0 | 1.0 |
| Yellow Iron Oxide | 3.0 | 3.0 | 3.0 | 3.0 | 3.0 | 3.0 | 3.0 | 3.0 |
| Black Iron Oxide | 0.4 | 0.4 | 0.4 | 0.4 | 0.4 | 0.4 | 0.4 | 0.4 |
| Polymethyl Sil(sesqui)oxane | 5.0 | 5.0 | 5.0 | 5.0 | 5.0 | 5.0 | 5.0 | 5.0 |
| Methylphenyl Polysiloxane | 5.0 | 5.0 | 5.0 | 5.0 | 5.0 | 5.0 | 5.0 | 5.0 |
| Glycerol Trioctanate | 2.0 | 2.0 | 2.0 | 2.0 | 2.0 | 2.0 | 2.0 | 2.0 |
| Squalane | 5.0 | 5.0 | 5.0 | 5.0 | 5.0 | 5.0 | 5.0 | 5.0 |
| Preservative | 0.2 | 0.2 | 0.2 | 0.2 | 0.2 | 0.2 | 0.2 | 0.2 |
| Flavor | 0.2 | 0.2 | 0.2 | 0.2 | 0.2 | 0.2 | 0.2 | 0.2 |
| Porous Silica L-3 | 5.0 | — | — | — | — | — | — | — |

TABLE 27-continued

| | Weight (mg) | | | | | | | |
|---|---|---|---|---|---|---|---|---|
| Porous Silica M-3 | — | 5.0 | — | — | — | — | — | — |
| Porous Silica N-3 | — | — | 5.0 | — | — | — | — | — |
| Porous Silica O-3 | — | — | — | 5.0 | — | — | — | — |
| Porous Silica P-3 | — | — | — | — | 5.0 | — | — | — |
| Porous Silica Q-3 | — | — | — | — | — | 5.0 | — | — |
| Porous Silica R-3 | — | — | — | — | — | — | 5.0 | — |
| Silicic Acid Anhydride | — | — | — | — | — | — | — | 5.0 |

[Table 29]

Questionnaire survey was conducted on 30 females as subjects, whose ages range from 20 to 30 years old, for long-lastingness of cosmetics and feel of use such as texture, immediately after the subjects were asked to use each of the powder foundations of Examples 8-19 to 8-36 and Comparative Example 8-2 and 3 hours after the subjects were asked to use against sweat or the like. Each of feel of use and long-lastingness of cosmetics was evaluated with 10 ranks in scores 10 to 1, starting from that being most excellent in feel of use and long-lastingness of cosmetics, and an average from the 30 subjects was calculated. The results are shown in Table 28.

[Table 30]

TABLE 28

| | Long-Lastingness of Cosmetics | | Feel of Use | |
|---|---|---|---|---|
| | Upon Application | After 3 hours | Upon Application | After 3 hours |
| Ex. 8-19 | 6.6 | 6.2 | 6.8 | 6.3 |
| Ex. 8-20 | 8.1 | 8.0 | 8.2 | 8.1 |
| Ex. 8-21 | 6.7 | 6.1 | 6.9 | 6.2 |
| Ex. 8-22 | 6.9 | 6.0 | 7.1 | 6.2 |
| Ex. 8-23 | 5.1 | 4.1 | 5.1 | 4.2 |
| Ex. 8-24 | 5.2 | 4 | 5.2 | 4 |
| Ex. 8-25 | 7.3 | 7.0 | 7.5 | 7.2 |
| Ex. 8-26 | 9.1 | 9.0 | 8.9 | 8.7 |
| Ex. 8-27 | 7.5 | 7.1 | 7.7 | 7.2 |
| Ex. 8-28 | 7.8 | 7.1 | 7.8 | 7.1 |
| Ex. 8-29 | 5.5 | 4.2 | 5.8 | 4.7 |
| Ex. 8-30 | 5.6 | 4.1 | 5.9 | 4.4 |
| Ex. 8-31 | 7.3 | 7.0 | 7.5 | 7.2 |
| Ex. 8-32 | 9.1 | 9.0 | 8.9 | 8.7 |
| Ex. 8-33 | 7.4 | 7.1 | 7.6 | 7.3 |
| Ex. 8-34 | 9.2 | 9.1 | 9.0 | 9.0 |
| Ex. 8-35 | 6.8 | 6.3 | 6.9 | 6.5 |
| Ex. 8-36 | 8.2 | 8.1 | 8.3 | 8.2 |
| Comp. Ex. 8-2 | 3.4 | 1.3 | 3.1 | 1.1 |

It can be seen from Table 28 that the use of the powder foundations containing the porous silicas A-3 to F-3 obtained in Examples 8-19 to 8-24 is excellent in long-lastingness of cosmetics against sweating and feel of use, such as texture, and that the use of the powder foundations containing the porous silicas G-3 to R-3 containing an emulsifying agent obtained in Examples 8-25 to 8-36 is even more excellent in long-lastingness against sweating and feel of use, such as texture, as compared to the use of the powder foundation containing silicic acid anhydride of Comparative Example 8-2.

Examples 8-37 to 8-54 and Comparative Example 8-3

Mica, yellow iron oxide, a liquid paraffin, squalane, methylphenyl polysiloxane, Vaseline, and one of the porous silicas A-3 to F-3 obtained in Preparation Examples 3-1 to 3-6, the porous silicas G-3 to R-3 containing an emulsifying agent obtained in Preparation Examples 3-7 to 3-10, and silicic acid anhydride were used in a composition as shown in Table 29, and the same procedures as in Examples 8-19 to 8-36 and Comparative Example 8-2 were carried out, to give a powder eye shadow.

[Table 31]

TABLE 29

| | Weight (mg) | | | | | | | | | |
|---|---|---|---|---|---|---|---|---|---|---|
| | Ex. | | | | | | | | | |
| | 8-37 | 8-38 | 8-39 | 8-40 | 8-41 | 8-42 | 8-43 | 8-44 | 8-45 | 8-46 |
| Mica | 61.6 | 61.6 | 61.6 | 61.6 | 61.6 | 61.6 | 61.6 | 61.6 | 61.6 | 61.6 |
| Red Iron Oxide | 1 | 1 | 1 | 1 | 1 | 1 | 1 | 1 | 1 | 1 |
| Yellow Iron Oxide | 2 | 2 | 2 | 2 | 2 | 2 | 2 | 2 | 2 | 2 |
| Spherical Polystyrene | 15 | 15 | 15 | 15 | 15 | 15 | 15 | 15 | 15 | 15 |
| Methylphenyl Polysiloxane | 9 | 9 | 9 | 9 | 9 | 9 | 9 | 9 | 9 | 9 |
| Glycerol Trioctanate | 6 | 6 | 6 | 6 | 6 | 6 | 6 | 6 | 6 | 6 |
| Preservative | 0.2 | 0.2 | 0.2 | 0.2 | 0.2 | 0.2 | 0.2 | 0.2 | 0.2 | 0.2 |
| Flavor | 0.2 | 0.2 | 0.2 | 0.2 | 0.2 | 0.2 | 0.2 | 0.2 | 0.2 | 0.2 |

TABLE 29-continued

|  | Weight (mg) | | | | | | | | | |
|---|---|---|---|---|---|---|---|---|---|---|
| Porous Silica A-3 | 5 | — | — | — | — | — | — | — | — | — |
| Porous Silica B-3 | — | 5 | — | — | — | — | — | — | — | — |
| Porous Silica C-3 | — | — | 5 | — | — | — | — | — | — | — |
| Porous Silica D-3 | — | — | — | 5 | — | — | — | — | — | — |
| Porous Silica E-3 | — | — | — | — | 5 | — | — | — | — | — |
| Porous Silica F-3 | — | — | — | — | — | 5 | — | — | — | — |
| Porous Silica G-3 | — | — | — | — | — | — | 5 | — | — | — |
| Porous Silica H-3 | — | — | — | — | — | — | — | 5 | — | — |
| Porous Silica I-3 | — | — | — | — | — | — | — | — | 5 | — |
| Porous Silica J-3 | — | — | — | — | — | — | — | — | — | 5 |

|  | Ex. | | | | | | | | Comp. Ex. |
|---|---|---|---|---|---|---|---|---|---|
|  | 8-47 | 8-48 | 8-49 | 8-50 | 8-51 | 8-52 | 8-53 | 8-54 | 8-3 |
| Mica | 61.6 | 61.6 | 61.6 | 61.6 | 61.6 | 61.6 | 61.6 | 61.6 | 61.6 |
| Red Iron Oxide | 1 | 1 | 1 | 1 | 1 | 1 | 1 | 1 | 1 |
| Yellow Iron Oxide | 2 | 2 | 2 | 2 | 2 | 2 | 2 | 2 | 2 |
| Spherical Polystyrene | 15 | 15 | 15 | 15 | 15 | 15 | 15 | 15 | 15 |
| Methylphenyl Polysiloxane | 9 | 9 | 9 | 9 | 9 | 9 | 9 | 9 | 9 |
| Glycerol Trioctanate | 6 | 6 | 6 | 6 | 6 | 6 | 6 | 6 | 6 |
| Preservative | 0.2 | 0.2 | 0.2 | 0.2 | 0.2 | 0.2 | 0.2 | 0.2 | 0.2 |
| Flavor | 0.2 | 0.2 | 0.2 | 0.2 | 0.2 | 0.2 | 0.2 | 0.2 | 0.2 |
| Porous Silica K-3 | 5 | — | — | — | — | — | — | — | — |
| Porous Silica L-3 | — | 5 | — | — | — | — | — | — | — |
| Porous Silica M-3 | — | — | 5 | — | — | — | — | — | — |
| Porous Silica N-3 | — | — | — | 5 | — | — | — | — | — |
| Porous Silica O-3 | — | — | — | — | 5 | — | — | — | — |
| Porous Silica P-3 | — | — | — | — | — | 5 | — | — | — |
| Porous Silica Q-3 | — | — | — | — | — | — | 5 | — | — |
| Porous Silica R-3 | — | — | — | — | — | — | — | 5 | — |
| Silicic Acid Anhydride | — | — | — | — | — | — | — | — | 5 |

[Table 32]

Questionnaire survey was conducted on 30 females as subjects, whose ages range from 20 to 30 years old, for the long-lastingness against sweating immediately after the subjects were asked to use the powder eye shadows obtained in Examples 8-37 to 8-54 and Comparative Example 8-3 or 3 hours after the use, and feel of use, such as texture. Each of feel of use and long-lastingness of cosmetics was evaluated with 10 ranks in scores 10 to 1, starting from that being most excellent in feel of use and long-lastingness of cosmetics, and an average from the 30 subjects was calculated. The results are shown in Table 30.

[Table 33]

TABLE 30

|  | Long-Lastingness of Cosmetics | | Feel of Use | |
|---|---|---|---|---|
|  | Upon Application | After 3 hours | Upon Application | After 3 hours |
| Ex. 8-37 | 6.8 | 6.5 | 6.9 | 6.5 |
| Ex. 8-38 | 8.1 | 8.0 | 8.2 | 8.2 |
| Ex. 8-39 | 6.8 | 6.3 | 6.9 | 6.4 |

TABLE 30-continued

| | Long-Lastingness of Cosmetics | | Feel of Use | |
|---|---|---|---|---|
| | Upon Application | After 3 hours | Upon Application | After 3 hours |
| Ex. 8-40 | 6.9 | 6.3 | 6.9 | 6.3 |
| Ex. 8-41 | 5.4 | 4.9 | 5.5 | 4.6 |
| Ex. 8-42 | 5.4 | 4.7 | 5.5 | 4.7 |
| Ex. 8-43 | 7.4 | 7.1 | 7.5 | 7.1 |
| Ex. 8-44 | 9.0 | 8.9 | 8.9 | 8.8 |
| Ex. 8-45 | 7.5 | 7.1 | 7.6 | 7.1 |
| Ex. 8-46 | 7.6 | 7.0 | 7.7 | 7.0 |
| Ex. 8-47 | 5.8 | 5.1 | 5.9 | 5.3 |
| Ex. 8-48 | 5.8 | 5.1 | 5.8 | 5.2 |
| Ex. 8-49 | 7.4 | 7.1 | 7.5 | 7.1 |
| Ex. 8-50 | 9.0 | 8.9 | 8.9 | 8.8 |
| Ex. 8-51 | 7.5 | 7.3 | 7.7 | 7.4 |
| Ex. 8-52 | 9.1 | 9.0 | 9.0 | 8.8 |
| Ex. 8-53 | 6.9 | 6.6 | 6.9 | 6.6 |
| Ex. 8-54 | 8.2 | 8.1 | 8.2 | 8.2 |
| Comp. Ex. 8-3 | 3.2 | 1.8 | 3.5 | 1.9 |

It can be seen from Table 30 that the use of the powder eye shadows containing the porous silicas A-3 to F-3 obtained in Examples 8-37 to 8-42 is excellent in long-lastingness of cosmetics against sweating and feel of use, such as texture, and that the use of the eye shadows containing the porous silicas G-3 to R-3 containing an emulsifying agent obtained in Examples 8-43 to 8-54 are even more excellent in long-lastingness against sweating and feel of use, such as texture, as compared to the use of the eye shadow containing silicic acid anhydride of Comparative Example 8-3.

Examples 9-1 to 9-18 and Comparative Example 9-1

A polyvinyl alcohol (trade name: PVA217, manufactured by Kuraray Co., Ltd.) having a degree of saponification of 88% by mol and one of the porous silica A-3 to F-3 obtained in Preparation Examples 3-1 to 3-6, the porous silica G-3 to R-3 containing an emulsifying agent obtained in Preparation Examples 3-7 to 3-10, and silicic acid anhydride (average particle size 30 μm, average pore size: 6.5 nm, specific surface area: 450 $m^2/g$) were mixed so as to have a ratio of solid contents of 70:30. One-hundred parts by weight of this mixture slurry and 5 parts by weight of a melamine resin (trade name: BECKAMINE MA-S, solid content: 60%, manufactured by DAINIPPON INK AND CHEMICALS, INC.) were added together, and the mixture was sufficiently mixed while stirring, to give a coating liquid. The resulting coating liquid was applied to a polyethylene terephthalate film with a bar coater so as to have a thickness of a coating film of 15 μm on a dry basis, to give an inkjet recording sheet.

Curling property was evaluated using the inkjet recording sheet obtained. The inkjet recording sheet was allowed to stand for 5 hours under the conditions of 30° C. and 80% RH, or conditions of 15° C. and 10% RH in a state where the inkjet recording sheet was tightly sealed in a plastic bag. Thereafter, the inkjet recording sheet was taken out from the bag, and allowed to stand on a horizontal table for 1 hour, and the amount curled up at the four corners after 1 hour was determined. Further, the inkjet-recording sheet was turned upside-down, and the amount curled up at the four corners was determined in the same manner. The maximum value of the 8 points obtained was defined as a curling value (evaluated in absolute value), and an average of 50 inkjet recording sheets was obtained. The results are shown in Table 31.

[Table 34]

TABLE 31

| | Curling Property | Ink Absorb- Ability | Image Quality | Water Resist- ance 1 | Water Resist- ance 2 | Light Fastness |
|---|---|---|---|---|---|---|
| Ex. 9-1 | 4.1 mm | 3.4 | 3.6 | 3.4 | 3.5 | 3.2 |
| Ex. 9-2 | 3.1 mm | 4.1 | 4.2 | 4.1 | 4.1 | 4.1 |
| Ex. 9-3 | 4.1 mm | 3.3 | 3.3 | 3.3 | 3.3 | 3.1 |
| Ex. 9-4 | 3.8 mm | 3.1 | 3.0 | 3.2 | 3.0 | 3.0 |
| Ex. 9-5 | 5.1 mm | 2.0 | 2.2 | 2.8 | 2.7 | 2.2 |
| Ex. 9-6 | 4.8 mm | 2.1 | 2.6 | 3.0 | 3.0 | 2.1 |
| Ex. 9-7 | 3.8 mm | 3.9 | 3.9 | 3.7 | 3.8 | 3.6 |
| Ex. 9-8 | 2.1 mm | 4.6 | 4.5 | 4.6 | 4.5 | 4.4 |
| Ex. 9-9 | 3.6 mm | 3.6 | 3.5 | 3.6 | 3.5 | 3.4 |
| Ex. 9-10 | 3.7 mm | 3.3 | 3.3 | 3.3 | 3.1 | 3.3 |
| Ex. 9-11 | 4.6 mm | 2.7 | 2.8 | 3.0 | 2.9 | 2.9 |
| Ex. 9-12 | 4.4 mm | 2.8 | 3.0 | 3.1 | 3.1 | 2.7 |
| Ex. 9-13 | 3.8 mm | 3.9 | 3.9 | 3.7 | 3.8 | 3.6 |
| Ex. 9-14 | 2.1 mm | 4.6 | 4.5 | 4.6 | 4.5 | 4.4 |
| Ex. 9-15 | 3.5 mm | 4.0 | 4.0 | 3.8 | 3.9 | 3.8 |
| Ex. 9-16 | 2.0 mm | 4.8 | 4.8 | 4.7 | 4.6 | 4.8 |
| Ex. 9-17 | 4.4 mm | 3.5 | 3.7 | 3.5 | 3.6 | 3.3 |
| Ex. 9-18 | 3.0 mm | 4.2 | 4.3 | 4.2 | 4.2 | 4.2 |
| Comp. Ex. 9-1 | 41.1 mm | 1.0 | 1.0 | 1.0 | 1.0 | 1.0 |

It can be seen from Table 31 that the use of the inkjet recording sheets containing the porous silicas A-3 to F-3 obtained in Examples 9-1 to 9-6 is excellent in property of controlling curling, and that the use of the inkjet recording sheets containing the porous silicas G-3 to R-3 containing an emulsifying agent obtained in Examples 9-7 to 9-18 is even more excellent in property of controlling curling, as compared to the use of the inkjet recording sheet containing silicic acid anhydride of Comparative Example 9-1.

Using the inkjet recording sheets obtained, the printing properties (ink absorbability, image quality, water resistance) were evaluated as follows. The results are shown in Table 31. The printing properties were evaluated by carrying out solid printing of yellow, magenta, cyan, black, green, red and blue using a commercially available inkjet printer (PM-770C, manufactured by Seiko Epson Corporation).

(i) Ink Absorbability: Printed portions were pressed with a plain white paper immediately after printing, and the ink absorbability was evaluated in 5 ranks of scores 5 to 1, starting from that having a smaller degree of ink transfer, and an average of 50 inkjet recording sheets was obtained.

(ii) Image Quality: The recorded image (vividness of images, bleeding of boundary of two different colors, clarity of fine ruled lines) was visually observed, and the recorded image was evaluated in 5 ranks of scores 5 to 1, starting from that having the most excellent image, and an average of 50 inkjet recording sheets was obtained.

(iii) Water Resistance 1: After printing water drops were adhered to the recorded image, and one minute later, the water drops were wiped off with an absorbent cotton. Water resistance was evaluated in 5 ranks of scores 5 to 1, starting from that having the smallest degree in loss of the fixed image, and an average of 50 inkjet recording sheets was obtained.

(iv) Water Resistance 2: After printing water drops were adhered to the recorded image, and allowed to stand for 24 hours. Water resistance was evaluated in 5 ranks of scores 5 to 1, starting from that having the smallest degree of ink bleeding, and an average of 50 inkjet recording sheets was obtained.

It can be seen from Table 31 that the use of the inkjet recording-sheets containing the porous silicas A-3 to F-3 obtained in Examples 9-1 to 9-6 is excellent in printing properties, and that the use of the inkjet recording sheets containing the porous silicas G-3 to R-3 containing an emulsifying agent obtained in Examples 9-7 to 9-18 is even more excellent in printing properties, as compared to the use of the inkjet recording sheet containing silicic acid anhydride of Comparative Example 9-2.

Light Fastness: A printed recorded image was subjected to irradiation with a desktop type accelerated weathering exposure device SUNTEST CPS+ manufactured by Toyo Seiki Seisaku-Sho, Ltd., under the conditions of a black panel temperature of 60° C., installed with a wind glass filter, degree of irradiation of 765 W/m². Optical densities of black and magenta after being subjected to irradiation for 60 hours or so were determined, and light fastness was evaluated by a percentage of change of densities. The results are shown in Table 31. (5: a percentage of change: 10% or less, 4: a percentage of change: 10 to 20%, 3: a percentage of change: 20 to 30%, 2: a percentage of change 30 to 40%, 1: a percentage of change: 40% or more).

It can be seen from Table 31 that the use of the inkjet recording sheets containing the porous silicas A-3 to F-3 obtained in Examples 9-1 to 9-6 is excellent in light fastness, and that the use of the inkjet recording sheets containing the porous silicas G-3 to R-3 containing an emulsifying agent obtained in Examples 9-7 to 9-18 is even more excellent in light fastness, as compared to the use of the inkjet recording sheet containing silicic acid anhydride of Comparative Example 9-3.

Examples 10-1 to 10-18 and Comparative Example 10-1

One of the porous silica A-3 to F-3 obtained in Preparation Examples 3-1 to 3-6, the porous silica G-3 to R-3 containing an emulsifying agent obtained in Preparation Examples 3-7 to 3-10, and silicic acid anhydride (average particle size 30 μm, average pore size: 6.5 nm, specific surface area: 450 m²/g) and polyethylene terephthalate (PET) were kneaded using a vent-type twin-screw kneader-extruder at 300° C., to give a PET having a silica content of 10%.

Next, the PET obtained was dried under a reduced pressure at 150° C. for 12 hours, and the dried product was subjected to melt-spinning at a spinning temperature of 290° C. and a spinning rate of 2700 m/minute, and thereafter the yarn was stretched at a stretching temperature of 90° C. and a hot set temperature of 130° C., to give 24 filaments of 84 dtex at a degree of stretching of the yarn of 35%. A plain fabrics was produced using this yarn as a longitudinal yarn and a latitudinal yarn. The plain fabrics were subjected to scouring, intermediate setting, amount of 10% alkali reduction and dyeing, and the fabrics were produced into a shirt fitting the sizes of the subjects.

Questionnaire survey was conducted on 30 males as subjects, whose ages range from 20 to 30 years old, who were asked to wear the shirts of Examples 10-1 to 10-18 and Comparative Example 10-1 for damp feel after sweating indoors at 30° C. and a humidity of 70% for 1 hour. The damp feel was evaluated in 10 ranks of scores 10 to 1, starting from the least pleasant damp feel, and an average of 30 subjects was calculated. The results are shown in Table 32.

[Table 35]

TABLE 32

| | Damp Feel |
|---|---|
| Ex. 10-1 | 6.3 |
| Ex. 10-2 | 7.1 |
| Ex. 10-3 | 6.5 |
| Ex. 10-4 | 6.5 |
| Ex. 10-5 | 4.6 |
| Ex. 10-6 | 4.5 |
| Ex. 10-7 | 7.2 |
| Ex. 10-8 | 8.3 |
| Ex. 10-9 | 7.1 |
| Ex. 10-10 | 7.1 |
| Ex. 10-11 | 4.8 |
| Ex. 10-12 | 4.7 |
| Ex. 10-13 | 7.2 |
| Ex. 10-14 | 8.3 |
| Ex. 10-15 | 7.5 |
| Ex. 10-16 | 8.6 |
| Ex. 10-17 | 6.4 |
| Ex. 10-18 | 7.2 |
| Comp. Ex. 10-1 | 2.4 |

It can be seen from Table 32 that the shirts containing the porous silicas A-3 to F-3 obtained in Examples 10-1 to 10-6 have less damp feel, and that the shirts containing the porous silicas G-3 to R-3 containing an emulsifying agent obtained in Examples 10-7 to 10-18 are even more excellent in light fastness, as compared to that of the shirt containing silicic acid anhydride of Comparative Example 10-1.

INDUSTRIAL APPLICABILITY

The agent capable of giving an ability of adsorbing moisture or a protein of the present invention can give an ability of adsorbing moisture or a protein to various materials.

The invention claimed is:
1. A method for imparting adsorbability of moisture- or a protein to a material by adding a moisture- or protein-adsorbability imparting agent to a material selected from the group consisting of food wrapping materials, filtration aid agents, sanitary articles, covering materials for wounds, insulation substrates, coating materials for semiconductor devices, cosmetics, and compositions containing synthetic fibers, wherein
the moisture- or protein-adsorbability imparting agent comprises a porous silica having a hexagonal pore structure, an average pore size of from 0.8 to 5 nm, an average particle size of 50 nm to 100 μm, a specific surface area of from 400 to 2000 m²/g, and a pore volume of from 0.1 to 3.0 cm³/g and the moisture- or protein-absorbability imparting agent further comprises a polyglycerol fatty acid ester obtained by esterification of a polyglycerol having an average degree of polymerization of 3 or more, and a fatty acid.

2. The method of claim 1, wherein the porous silica of the moisture- or protein-adsorbability imparting agent shows an X-ray diffraction pattern having one or more peaks at a diffraction angle corresponding to a d value of greater than 2.0 nm, and wherein in the X-ray diffraction pattern there exist no peaks at a diffraction angle corresponding to a d value smaller than 1.0 nm that have a relative intensity of greater than 200% of the most intensive peak among said peaks.

3. The method of claim 1, wherein the porous silica of the moisture- or protein-adsorbability imparting agent has an amount of chlorophyll adsorption of 5 mg or more per 100 mg of the porous silica according to a test for chlorophyll adsorption.

4. The method of claim 1, wherein the porous silica of the moisture- or protein-adsorbability imparting agent has an average particle size of primary particles of from 30 to 500 nm.

5. The method of claim 1, wherein the moisture- or protein-adsorbability imparting agent is added in amount of 0.001 to 100% by weight.

6. A method for imparting adsorbability of moisture or a protein to a material by adding a moisture- or protein-adsorbability imparting agent to a material wherein the material is a sanitary article and the moisture- or protein-adsorbability imparting agent is added in an amount of 0.001 to 30% by weight, wherein the moisture- or protein-adsorbability imparting agent comprises a porous silica having a hexagonal pore structure, an average pore size of from 0.8 to 5 nm, an average particle size of 50 nm to 100 μm, a specific surface area of from 400 to 2000 $m^2/g$, and a pore volume of from 0.1 to 3.0 $cm^3/g$.

* * * * *